(12) United States Patent
Koblish et al.

(10) Patent No.: US 12,150,629 B2
(45) Date of Patent: Nov. 26, 2024

(54) LUNG ACCESS DEVICE

(71) Applicant: Verix Health, Inc., Santa Clara, CA (US)

(72) Inventors: Josef Koblish, Sunnyvale, CA (US); Chau Cao, San Jose, CA (US); Eza Koch, South Abington Township, PA (US); Benjamin E. Morris, Jeffersonville, IN (US)

(73) Assignee: Verix Health, Inc., Santa Clara, CA (US)

( * ) Notice: Subject to any disclaimer, the term of this patent is extended or adjusted under 35 U.S.C. 154(b) by 513 days.

(21) Appl. No.: 17/246,623

(22) Filed: May 1, 2021

(65) Prior Publication Data

US 2022/0000461 A1 Jan. 6, 2022

Related U.S. Application Data

(63) Continuation of application No. 16/997,154, filed on Aug. 19, 2020, now Pat. No. 11,020,099, which is a
(Continued)

(51) Int. Cl.
*A61B 10/04* (2006.01)
*A61B 1/00* (2006.01)
(Continued)

(52) U.S. Cl.
CPC .......... *A61B 10/04* (2013.01); *A61B 1/00105* (2013.01); *A61B 1/0052* (2013.01);
(Continued)

(58) Field of Classification Search
CPC . A61B 10/02; A61B 10/0233; A61B 10/0266; A61B 10/0275; A61B 10/0283;
(Continued)

(56) References Cited

U.S. PATENT DOCUMENTS

| 2008/0249436 A1 | 10/2008 | Darr |
| 2016/0331358 A1 | 11/2016 | Gordon |

(Continued)

FOREIGN PATENT DOCUMENTS

| CN | 111248947 | 6/2020 |

OTHER PUBLICATIONS

Invitation To Pay Additional Fees and, Where Applicable, Protest Fee, Form PCT/ISA/206, International Application No. PCT/US2021/040023, dated Nov. 4, 2021,(12 pages).
(Continued)

*Primary Examiner* — Wade Miles
(74) *Attorney, Agent, or Firm* — Michael J. Bolan; Vista IP Law Group, LLP

(57) ABSTRACT

A pulmonary access device comprises an elongated shaft having a proximal shaft section, a bendable shaft section, a distal shaft section, and a distal tip. The pulmonary access device further comprises an elongated sheath having a proximal sheath section, a malleable distal sheath section, and working channel. The working channel is configured for slidably receiving the elongated shaft. The pulmonary access device further comprises a handle assembly including a handle body. The handle body is affixed to a proximal end of the elongated shaft. The handle body is removably affixed to a proximal end of the elongated sheath.

8 Claims, 50 Drawing Sheets

Related U.S. Application Data continuation-in-part of application No. 16/919,099, filed on Jul. 1, 2020, now Pat. No. 11,033,298.

(51) Int. Cl.

| | | |
|---|---|---|
| *A61B 1/005* | (2006.01) | |
| *A61B 1/018* | (2006.01) | |
| *A61B 1/267* | (2006.01) | |
| *A61B 10/02* | (2006.01) | |
| *A61B 8/12* | (2006.01) | |
| *A61B 10/06* | (2006.01) | |

(52) U.S. Cl.
CPC ............ *A61B 1/018* (2013.01); *A61B 1/2676* (2013.01); *A61B 10/0233* (2013.01); *A61B 8/12* (2013.01); *A61B 2010/0208* (2013.01); *A61B 10/0283* (2013.01); *A61B 2010/045* (2013.01); *A61B 10/06* (2013.01)

(58) Field of Classification Search
CPC ..... A61B 10/04; A61B 10/06; A61B 17/3421; A61B 17/3423; A61B 2017/3425; A61B 2017/3427; A61B 2017/3429; A61B 2017/00809; A61B 2010/0208; A61B 2010/0225; A61B 2010/045

See application file for complete search history.

(56) References Cited

U.S. PATENT DOCUMENTS

| | | | |
|---|---|---|---|
| 2018/0289388 A1 | 10/2018 | Lenker et al. | |
| 2019/0090724 A1* | 3/2019 | Keast | ................... A61B 1/0051 |
| 2019/0142528 A1 | 5/2019 | Vertikov | |

OTHER PUBLICATIONS

PCT International Search Report and Written Opinion for International Appln. No. PCT/US2021/040023, Applicant Verix Health, Inc., dated Jan. 4, 2022, (18 pages).

\* cited by examiner

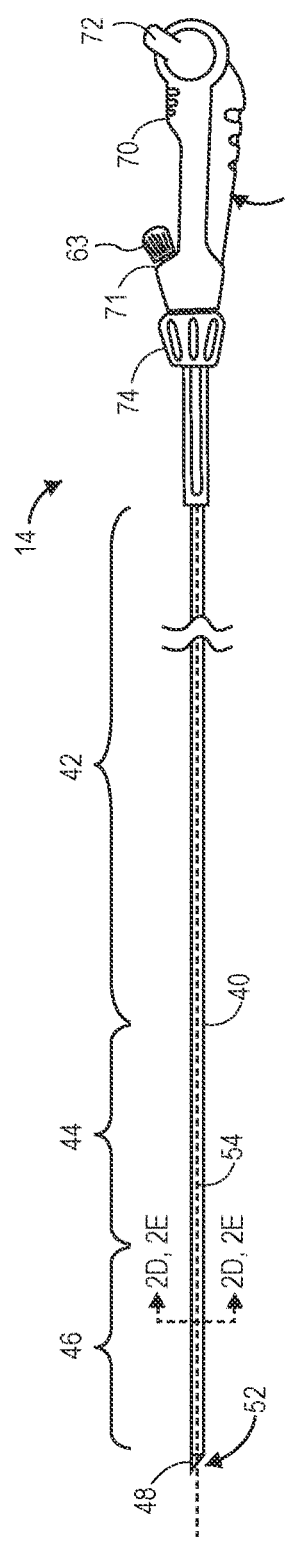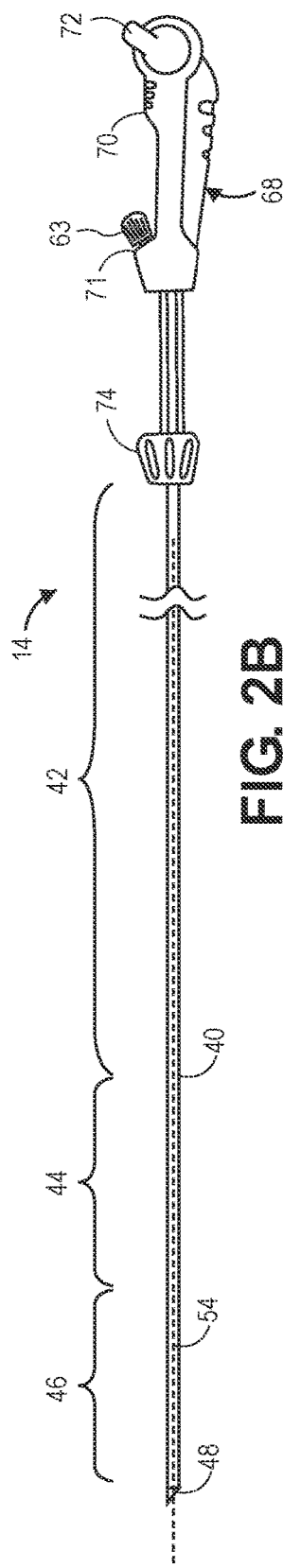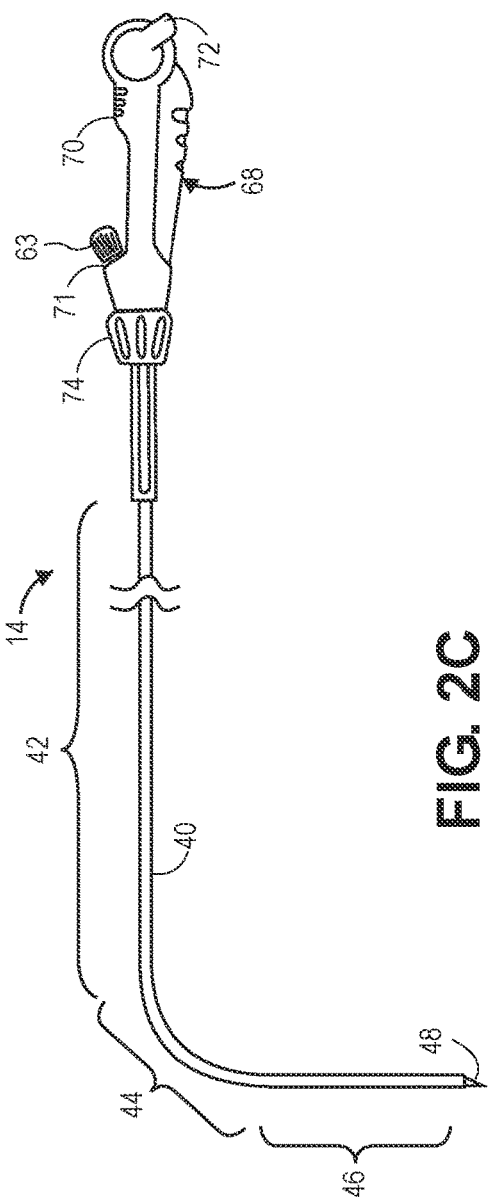

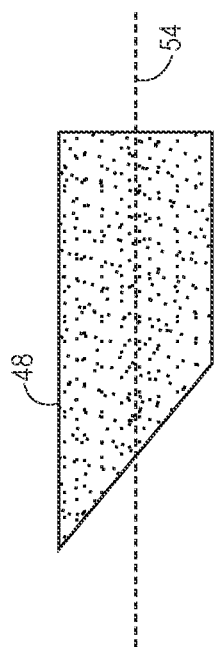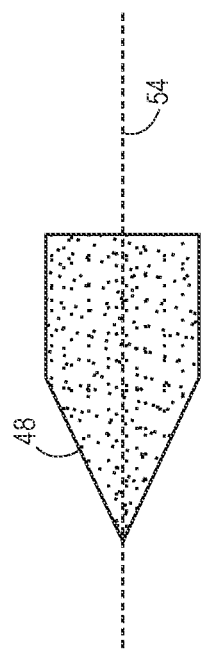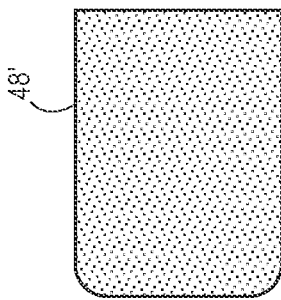

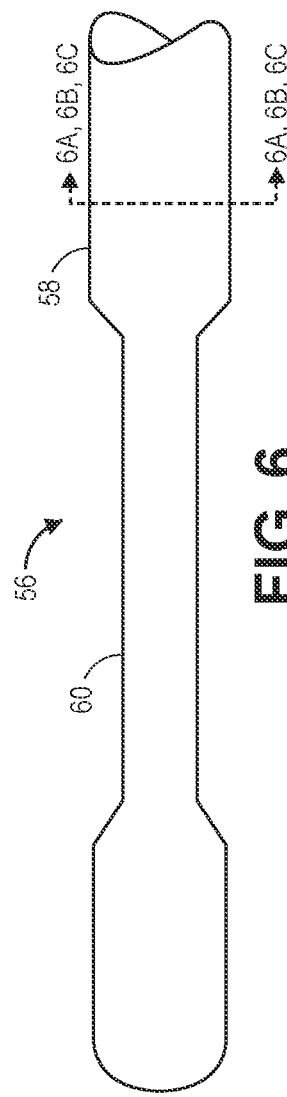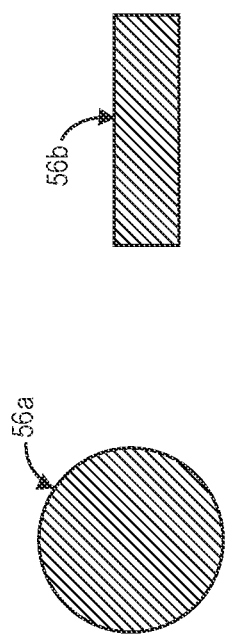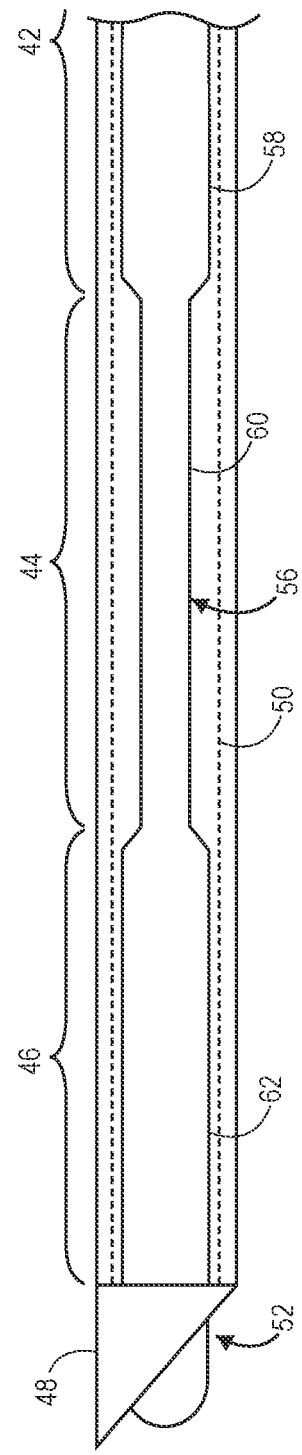

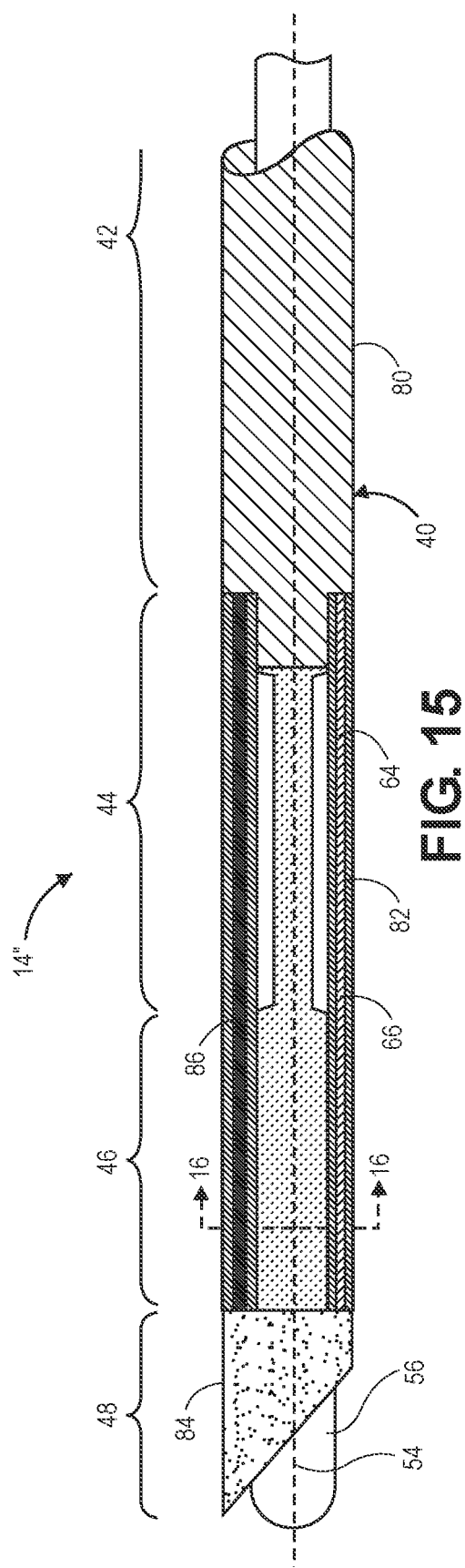
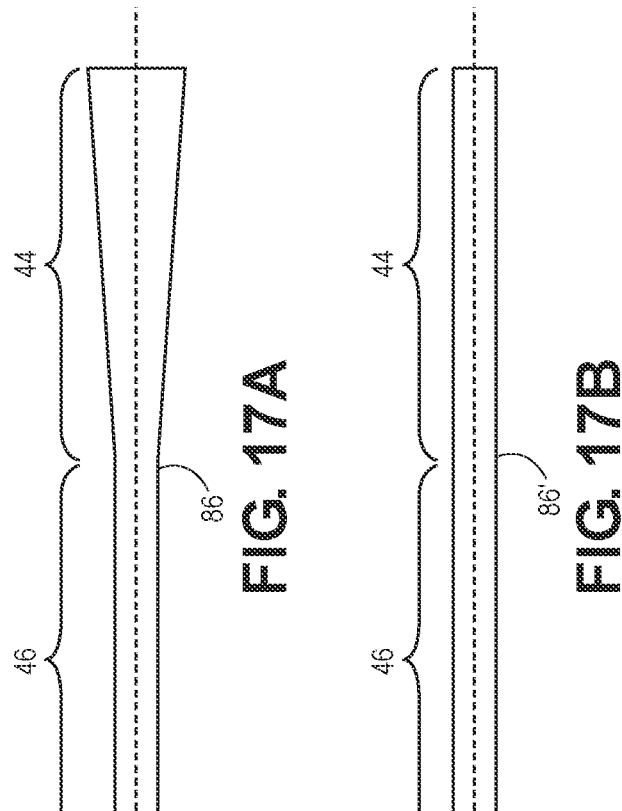
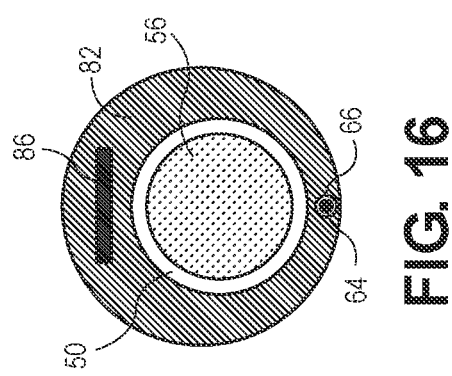
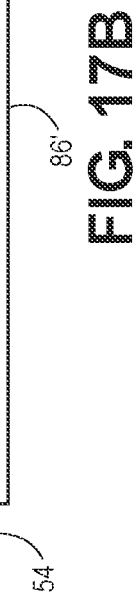

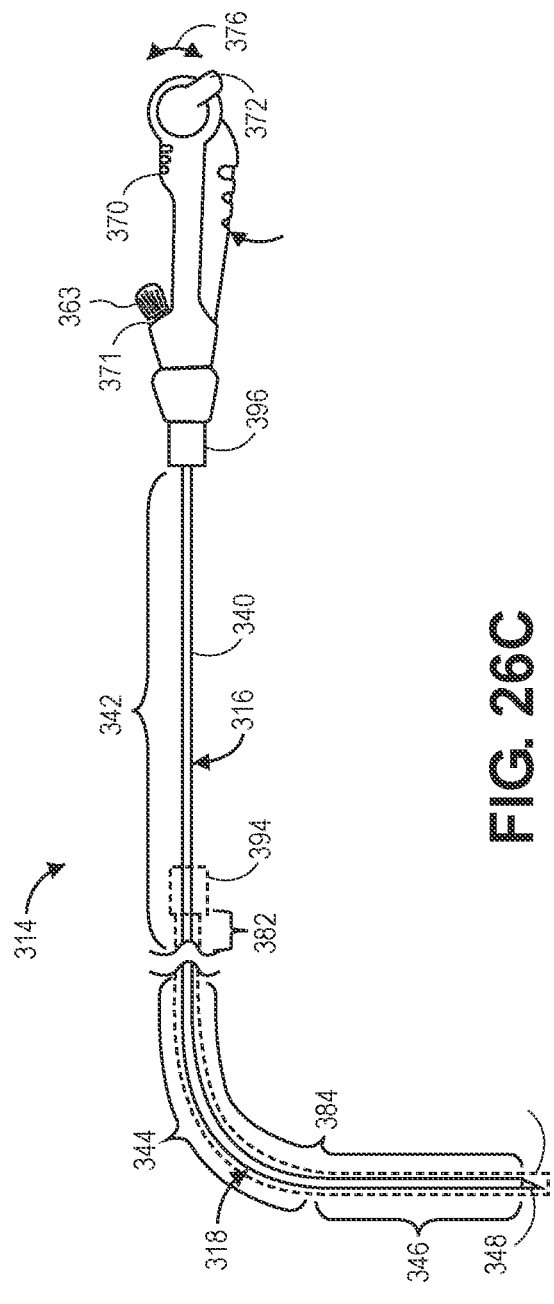
FIG. 26C
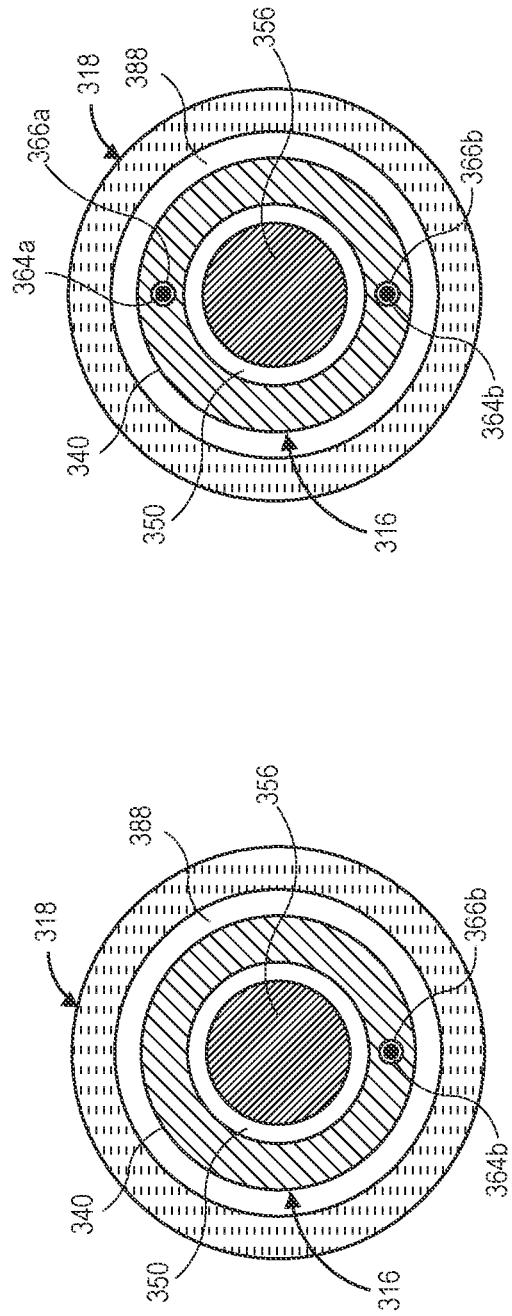
FIG. 26E
FIG. 26D

LUNG ACCESS DEVICE

RELATED APPLICATIONS

The present application is a continuation of U.S. patent application Ser. No. 16/997,154, filed Aug. 19, 2020, which is a continuation-in-part of U.S. patent application Ser. No. 16/919,099, filed Jul. 1, 2020, which are expressly incorporated herein by reference.

FIELD

The present disclosure relates generally to surgical devices, and more specifically, to methods, systems, and devices for navigating to and biopsy lung nodules.

BACKGROUND

Early diagnosis of potentially cancerous tissue is an important step in the treatment of cancer, because the sooner that cancerous tissue can be treated, the better the patient's chances are for survival. Typical diagnostic procedures involve biopsying tissue at a site of interest. Biopsies are a group of medical diagnostic tests used to determine the structure and composition of tissues or cells. In biopsy procedures, cells or tissues are sampled from an organ or other body part to permit their analysis, e.g., under microscope. Generally, if an abnormality is found through superficial examination, such as palpation or radiographic imaging, a biopsy can be performed to determine the nature of the suspected abnormality.

Biopsies can be performed on a number of organs, tissues, and body sites, both superficial and deep, and a variety of techniques may be utilized depending on the tissue or body part to be sampled, the location, size, shape, and other characteristics of the abnormality, the number of abnormalities, and patient preference. Fine needle aspiration (FNA) is typically performed to sample deep tissues using a fine gauge needle (22 or 25 gauge) inserted percutaneously or through an endoscope under ultrasound guidance (EUS-FNA). By contrast, surgical biopsy is generally performed as an open procedure and can be either excisional (removal of an entire lesion) or incisional (removal of a piece of a lesion).

Surgical biopsies generally permit removal of more tissue than fine needle biopsies, and thus, are less prone to misdiagnosis. However, open surgical procedures are significantly more expensive than needle biopsies, require more time for recuperation, require sutures, can leave a disfiguring scar, require anesthesia, carry a small risk of mortality, and can result in bleeding, infection, and wound healing problems.

In contrast, fine needle biopsies carry risks of their own. For example, the relatively small quantities of tissue sampled may not be representative of the region of interest from which it is taken, particularly when that region of interest is very small or very hard. As another example, fine gauge needles are typically stiffer, and less prone to deflection. Thus, while it may be possible to guide the needle to the region of interest, it may not be possible to accurately sample the site of interest if the needle is too stiff to navigate the same path through the tissue.

The global lung cancer epidemic, combined with the adoption of lung cancer screening, may result in an increasing number of suspicious solitary pulmonary nodules (SPNs) found on chest computed tomography (CT) scans or other scans. Suspicious SPNs, which typically exist in the periphery of lungs, may be difficult to access and diagnose using current bronchoscopic technologies designed primarily for the central airway. Peripheral lung nodules, or SPNs, may be rounded benign or malignant masses that may range in size between 5-25 mm. When an SPN is identified, it may need to be diagnosed with a biopsy. Typically, FNA may be utilized to access and obtain a biopsy from identified SPNs with a transbronchial approach through a bronchoscope inserted through a patient's mouth and throat into the bronchial airways of a lung, or with a transthoracic approach though a patient's thoracic cavity. Generally, the transbronchial approach may be favored over the transthoracic approach as access to the SPNs may be gained through existing airways of the lung without puncturing body tissue, and furthermore, puncturing the outer lining of a lung, which may lead to a pneumothorax.

Existing systems may be constrained by difficulties in accessing lung nodules via the transbronchial approach, especially in the smaller peripheral airways that may be too narrow to accommodate larger catheters and biopsy apparatuses. Furthermore, as SPNs are often located in the deep periphery of the lungs, and in particular, within the parenchyma of the lungs away from any airways, it may be difficult or impossible to reach such SPNs through airways of the lungs. Further, biopsy needles used in typical transbronchial approaches normally are straight and relatively inflexible. Thus, it may be difficult to navigate these biopsy needles along small and tortuous peripheral airways. In this case, a transthoracic approach accessing an SPN by puncturing through a patient's thoracic cavity may need to be used.

In some instances, the material of the needle may inelastically yield, and thus may sustain exceedingly high stresses when negotiating tight turns in these small and tortuous peripheral airways. Thus, it is not uncommon that a needle will yield or "kink" with a very acute irreversible bend that permanently alters the distal end of the needle, and therefore, their distal trajectories. Such an event renders the needle useless and creates a hazard to safely removing the needle from the body via the bronchoscope.

In addition, a straight needle trajectory is dictated by the position and orientation of the distal end of the bronchoscope. Most needles are not capable of making adjustments to deviate from this trajectory towards SPNs or otherwise away from anatomical obstacles. Thus, straight biopsy needles obtain samples along an axis of the needle through back and forth motion of the needle. As a result, obtaining multiple samples from different regions of a single SPN can be difficult and can require repeated repositioning of the bronchoscope.

There exist pre-shaped or pre-curved sheaths that can be advanced out the distal end of a bronchoscope to extend the bronchoscope channel through which biopsy tools can be introduced into the deep periphery of the lungs. However, the pre-shaped or pre-curved sheaths do not address the issue of acing SPNS that are in the parenchyma of the lung outside the airway. There also exist steerable lung biopsy needles that are capable of articulating to provide access to SPNs for biopsy that are deeper in the bronchial airways of a lung. These steerable lung biopsy needles are not capable of puncturing the wall of airway, and thus, are not capable of accessing SPNs that are in the parenchyma of the lung outside the airway. Also, because these steerable lung biopsy needles must accommodate steering functionality in the form of pull wires, to the extent that they are used as access devices for other biopsy tools, the size of the bronchoscope through one of these biopsy needles is to be introduced may need to be unduly increased, such that the working channel for the biopsy tools may be properly sized. There also exists a lung biopsy needle that is capable of puncturing a bronchial airway of a lung to access SPNs that are in the parenchyma of the lung. However, this lung biopsy needle is not capable of taking multiple samples from different regions of a single SPN in a controlled manner.

As a transthoracic approach may be viewed as more invasive than a transbronchial approach and may require more recovery time than a transbronchial approach, it is desirable to provide a lung biopsy needle that is capable of navigating the tortuous pathways of the deep or far periphery of the bronchial airways of the lungs, and taking multiple samples from different regions of an SPN located in the parenchyma of the lungs that could only be previously performed using a transthoracic approach. Furthermore, it is also desirable to provide a working channel having a relatively large working channel through which biopsy tools can be introduced without having to increase the size of the bronchoscope.

SUMMARY

In accordance with a first aspect of the present inventions, a pulmonary access device comprises an elongated shaft having a proximal shaft section, a bendable shaft section, a distal shaft section, and a distal tip. The pulmonary access device further comprises an elongated sheath having a proximal sheath section, a malleable distal sheath section, and a working channel. The working channel is configured for slidably receiving the elongated shaft.

The pulmonary access device further comprises a handle assembly including a handle body. A proximal end of the elongated shaft is affixed to the handle body, and a proximal end of the elongated sheath is removably affixed to the handle body. In one embodiment, the proximal end of the elongated sheath and the handle body have complementary connectors (e.g., luer connectors) configured for mating the elongated sheath and handle body together.

In another embodiment, the bendable shaft section distally extends from the malleable distal sheath section when the handle body is affixed to the proximal end of the elongated sheath. In still another embodiment, the handle assembly further comprises a deflection control actuator affixed to the handle body. The deflection control actuator is operably connected to the elongated shaft to bend the bendable shaft section.

In yet another embodiment, the elongated shaft further has a working channel, and the pulmonary access device further comprises a profiled stylet configured for being disposed in the working channel of the elongated shaft. The profiled stylet has a proximal stylet section with a first lateral stiffness profile, an intermediate stylet section having a second lateral stiffness profile less than the first lateral stiffness profile, and a distal stylet section. When the profiled stylet is disposed in the working channel of the elongated shaft, the intermediate stylet section axially aligns with the bendable shaft section. The pulmonary access device further comprises a pull wire affixed to the distal shaft section, such that, when the pull wire is tensioned, the bendable shaft section bends, thereby deflecting the distal shaft section relative to the proximal shaft section.

In accordance with a second aspect of the present inventions, a pulmonary biopsy system comprises the pulmonary access device described above and a bronchoscope having a working channel in which the pulmonary access device is disposed. The pulmonary biopsy system may further comprise a biopsy device, in which case, the profiled stylet and the biopsy device may be configured for being interchangeably disposed in the working channel of the pulmonary access device.

In accordance with a third aspect of the present inventions, a method of using the pulmonary access device described above to biopsy a solitary pulmonary nodule (SPN) located in a lung of a patient is provided. The method comprises navigating the pulmonary access device through a bronchial airway of the lung and actively deflecting the distal shaft section while the bendable shaft section distally extends from the malleable distal sheath section, thereby locating the distal tip of the elongated shaft adjacent a first site of the SPN. The method further comprises distally advancing the malleable distal sheath section over the bendable shaft section while the distal shaft section is actively deflected, such that the malleable distal sheath section assumes a curve of the bendable shaft section, proximally removing the elongated shaft from the working channel of the elongated sheath, distally advancing a biopsy tool through the working channel of the elongated sheath while the malleable distal sheath section assumes the curve of the bendable shaft section, and operating the biopsy tool to take a biopsy at the first site of the SPN In one method, the SPN is located in parenchyma of the patient, in which case, the method may further comprise puncturing the distal tip of the elongated shaft through a wall of the bronchial airway into the parenchyma, and tracking the distal tip of the elongated shaft through the parenchyma to the first site of the SPN by actively deflecting the distal shaft section while distally advancing the elongated shaft. The malleable distal sheath section is distally advanced through the parenchyma over the bendable shaft section while the distal shaft section is actively deflected. Another method further comprises repeating the navigating, actively deflecting, distally advancing of the malleable distal sheath section, proximally removing, distally advancing of the biopsy tool, and operating steps for a second site of the SPN different from the first site of the SPN. Still another method further comprises introducing a bronchoscope through the bronchial airway of the patient, in which case, navigating the pulmonary access device through the bronchial airway of the patient may comprise introducing the pulmonary access device through the bronchoscope into the bronchial airway of the patient. In yet another method, navigating the pulmonary access device through the bronchial airway of the lung comprises navigating the elongated shaft and the elongated sheath at the same time through the bronchial airway of the lung.

In accordance with a fourth aspect of the present inventions, a method of biopsying a solitary pulmonary nodule (SPN) located in a lung of a patient using a pulmonary access device comprising an elongated shaft and an elongated sheath disposed about the elongated shaft is provided. The method comprises navigating the pulmonary access device through a bronchial airway of the lung. The method further comprises actively bending a shaft section of the elongated shaft while the shaft section distally extends from a distal sheath section of the elongated sheath, thereby locating a distal tip of the elongated shaft adjacent a first site of the SPN. The method further comprises distally advancing the distal sheath section over the shaft section while the shaft section is actively bent, such that the distal sheath section assumes a curve of the bent shaft section. The method further comprises proximally removing the elongated shaft from the elongated sheath. The curve assumed by the shaft section remains after proximal removal of the elongated shaft from the elongated sheath. The method further comprises distally advancing a biopsy tool through the elongated sheath while the shaft section assumes the curve. The method further comprises operating the biopsy tool to take a biopsy at the first site of the SPN.

In one method, the SPN is located in parenchyma of the patient, in which case, the method may further comprise puncturing a distal tip of the elongated shaft through a wall of the bronchial airway into the parenchyma, and tracking the distal tip of the elongated shaft through the parenchyma to the first site of the SPN by actively bending the shaft section while distally advancing the elongated shaft, wherein the distal sheath section is distally advanced through the parenchyma over the bent shaft section. Another method further comprises repeating the navigating, actively deflecting, distally advancing of the distal sheath section, proximally removing, distally advancing of the biopsy tool, and operating steps for a second site of the SPN different from the first site of the SPN. Still another method further comprises introducing a bronchoscope through the bronchial airway of the patient, wherein navigating the pulmonary access device through the bronchial airway of the patient comprises introducing the pulmonary access device through the bronchoscope into the bronchial airway of the patient. In yet another method, navigating the pulmonary access device through the bronchial airway of the lung comprises navigating the elongated shaft and the elongated sheath at the same time through the bronchial airway of the lung.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of preferred embodiments of the present invention, in which similar elements are referred to by common reference numerals. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 2A is a plan view of a pulmonary access device used in the transbronchial pulmonary biopsy system of FIG. 1, particularly shown in a proximally retracted position;

FIG. 2B is a plan view of the pulmonary access device of FIG. 2A, particularly shown in a distally advanced position;

FIG. 2C is a plan view of the pulmonary access device of FIG. 2A, particularly shown in a deflected position;

FIG. 4A is a profile view of a tissue-penetrating distal tip of an elongated shaft of the pulmonary access device of FIG. 2A;

FIG. 4B is another profile view of a tissue-penetrating distal tip of an elongated shaft of the pulmonary access device of FIG. 2A;

FIG. 5 is a profile view of an atraumatic distal tip of an elongated shaft of the pulmonary access device of FIG. 2A;

FIG. 6 is a profile view of one embodiment of a profiled stylet used in the pulmonary access device of FIG. 2A;

FIG. 6A is a cross-sectional view of one variation of the profiled stylet of FIG. 6, taken along the line 6A-6A;

FIG. 6B is a cross-sectional view of another variation of the profiled stylet of FIG. 6, taken along the line 6B-6B;

FIG. 6C is a cross-sectional view of still another variation of the profiled stylet of FIG. 6, taken along the line 6C-6C;

FIG. 7 is a profile view of the pulmonary access device of FIG. 2A;

FIG. 15 is a partially-cutaway profile view of one specific embodiment of the pulmonary access device of FIG. 2A;

FIG. 16 is a cross-sectional view of the pulmonary access device of FIG. 15, taken along the line 16-16;

FIG. 17A is a plan view of one embodiment of a steering plate used in the pulmonary access device of FIG. 15;

FIG. 17B is a plan view of another embodiment of the steering plate used in the pulmonary access device of FIG. 15;

FIG. 26C is a plan view of the pulmonary access device of FIG. 26A, particularly shown in a deflected position;

FIG. 26D is a cross-sectional view of one variation of the pulmonary access device of FIG. 26B, taken along the line 26D-26D;

FIG. 26E is a cross-sectional view of another variation of the pulmonary access device of FIG. 26B, taken along the line 26E-26E;

DETAILED DESCRIPTION OF THE ILLUSTRATED EMBODIMENTS

Figure 1:
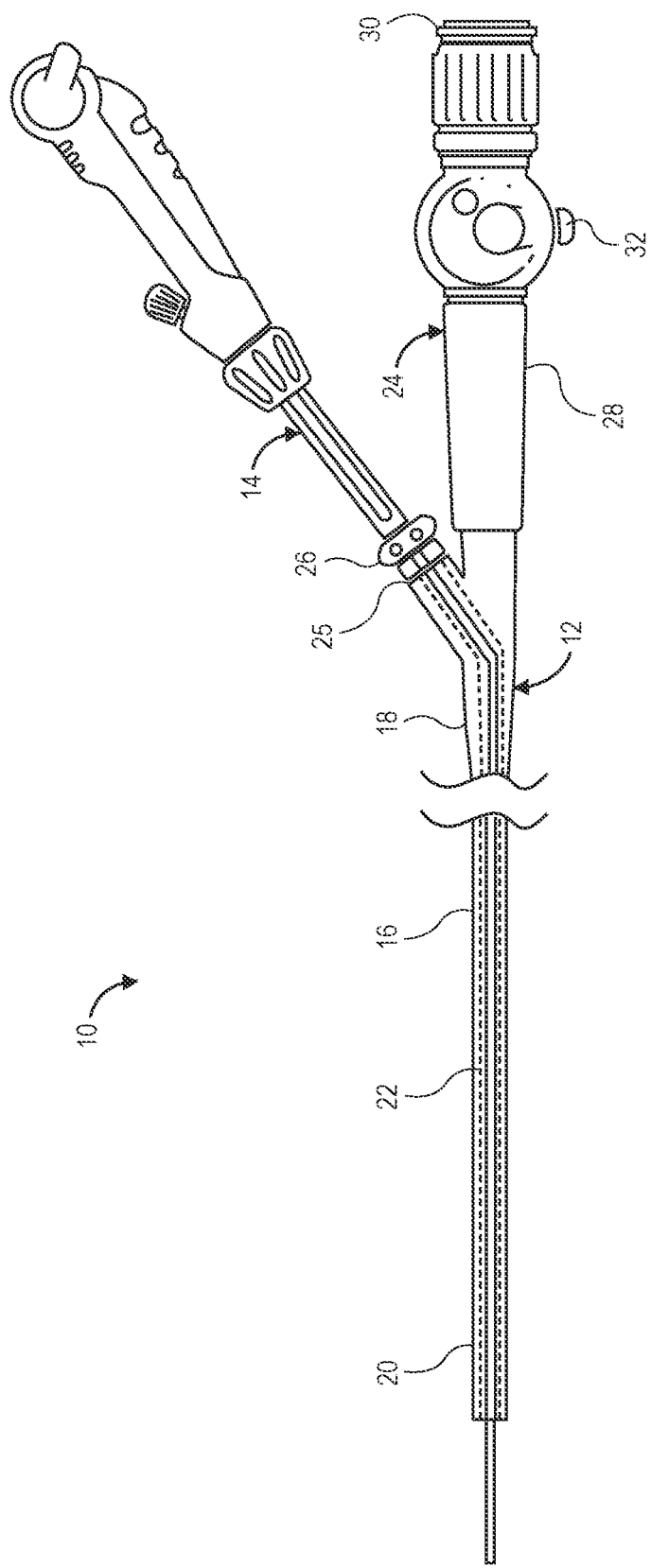
FIG. 1 is a plan view of a transbronchial pulmonary biopsy system constructed in accordance with one embodiment of the present inventions.

Referring to FIG. 1, one exemplary embodiment of a transbronchial pulmonary biopsy system 10 capable of accessing an identified solitary pulmonary nodule (SPN) in the parenchyma of a lung located remotely from a bronchial airway in the lung will be described. The transbronchial pulmonary biopsy system 10 generally comprises a flexible bronchoscope 12 and a pulmonary access device 14.

The bronchoscope 12 is conventional in nature, and can take the form of, but not limited to, BF-P180 or endobronchial ultrasound bronchoscopy (EBUS) scope manufactured by Olympus. The bronchoscope 12 is configured for being inserted through the patient's mouth or nose and into the bronchial airways of the patient. The bronchoscope 12 comprises an elongated shaft 16 having a proximal end 18 and a distal end 20, a working channel 22 extending through the elongated shaft 16, a handle assembly 24 affixed to the proximal end 18 of the elongated shaft 16, and an access port 25 leading to the working channel 22 within the elongated shaft 16. The working channel 22 may conventionally have a diameter of 2.8 mm or a diameter of 2.65 mm. The access port 25 includes a coupling 26 configured for locking the pulmonary access device 14 within the working channel 22 of the bronchoscope 12. In an optional embodiment, the access port 25 does not have a coupling 26, in which case, the pulmonary access device 14 may be freely displaced relative to the working channel 18 of the bronchoscope 12.

The bronchoscope 12 further comprises one or more lights (not shown) disposed at the distal end 20 of the elongated shaft 16 for illumination and optical fibers (not shown) extending through the elongated shaft 16 for capturing and transmitting images at the distal end 20 of the elongated shaft 16. The handle assembly 24 comprises a handle body 28 affixed to the proximal end 18 of the elongated shaft 16, and an eyepiece 30 affixed to the handle body 26 for viewing images at the distal end 20 of the elongated shaft 16, thereby allowing a practitioner to observe the progress of the bronchoscope 18 through the patient on a monitor as the bronchoscope 12 is steered through the bronchial airways of the patient in proximity to an SPN. A camera (not shown) may be connected to the eyepiece 30 for porting images to a monitor (not shown). The handle assembly 24 further comprises a light adapter 32 to which a light cable (not shown) may be connected for optical coupling to the lights at the distal end 20 of the elongated shaft 16.

The pulmonary access device 14 is configured for tracking through the working channel 22 of the bronchoscope 12, being navigated through the tortuous pathways of the deep or far periphery of the bronchial airways of the lungs, puncturing out of a bronchial airway, traversing the parenchyma of the lung, and accessing a selected SPN in the parenchyma of the lung, such that biopsy samples can be taken at multiple sites of the selected SPN. In one variation, the pulmonary access device 14 serves as a biopsy device that takes the biopsy samples from the selected SPN. In another variation, the pulmonary access device 14 serves as a channel device that delivers commercially available or future developed biopsy tools (e.g., biopsy needles, brushes, forceps, etc.) to the selected SPN, which biopsy tools can then be operated to take the biopsy samples from the selected SPN.

Referring further to FIG. 2A-2C, one exemplary embodiment of the pulmonary access device 14 comprises an elongated shaft 40 having a steerable distal section. In the preferred embodiment, the elongated shaft 40 has compression resistance and is highly torqueable to provide the pulmonary access device 14 with steering fidelity, axial pushability, and SPN piercing force translation. The elongated shaft 40 may be constructed, such that it has a 1:1 torque transmission and a 1:1 axial transmission. In this manner, rotational and axial displacement at the distal end of the elongated shaft 40 will consistently track the rotational and axial displacement of the proximal end of the elongated shaft 40, such that the distal tip of the elongated shaft 40 may traverse and change direction in the parenchyma to the SPN, and thus, be consistently and predictably located at the various sampling sites of a selected SPN, as will be described in further detail below. The torsional profile along the entire elongated shaft 40 is preferably uniform, whereas the lateral stiffness profile along the elongated shaft 40 preferably has a transition directly proximal to the steerable distal section of the elongated shaft 40 to facilitate tracking through the parenchyma.

To this end, the elongated shaft 40 has a proximal shaft section 42, a bendable shaft section 44, a distal shaft section 46, a distal tip 48, and a channel 50 (either a biopsy channel or a working channel) (shown in FIGS. 2D and 2E) extending through the proximal shaft section 42, bendable shaft section 44, and distal shaft section 46, and terminating at a distal opening 52 in the distal tip 48 (shown best in FIGS. 7 and 8).

Figure 3A:
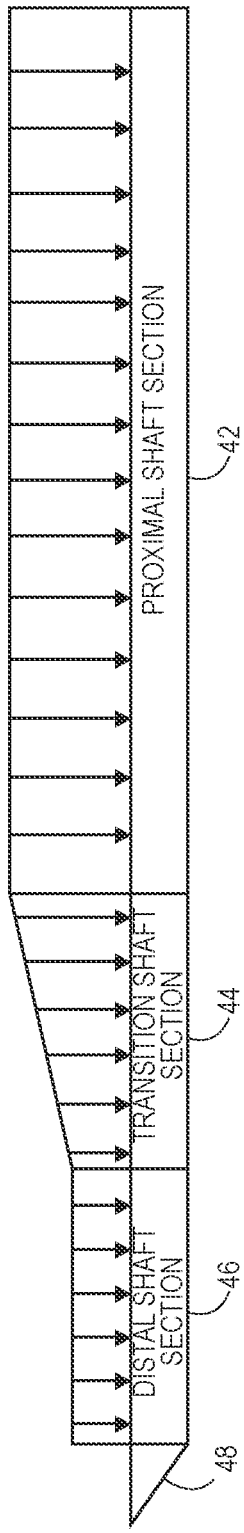
FIG. 3A is a plan view of one lateral stiffness profile of an elongated shaft of the pulmonary access device of FIG. 2A.
Figure 3B:
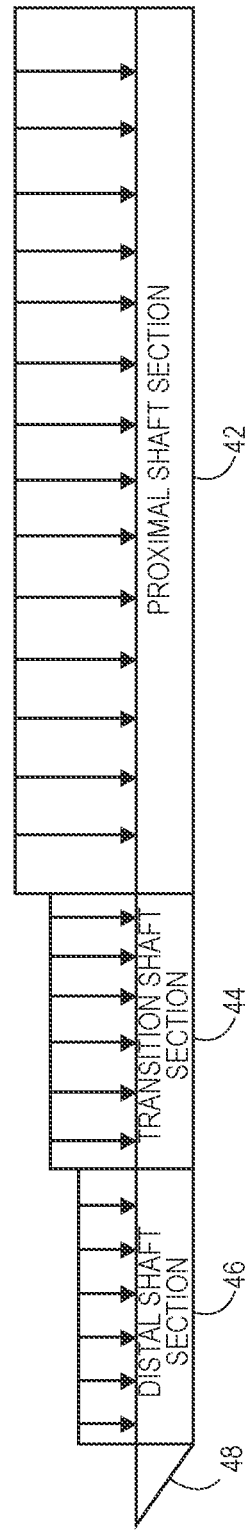
FIG. 3B is a plan view of another lateral stiffness profile of an elongated shaft of the pulmonary access device of FIG. 2A.

In this exemplary embodiment, the lateral stiffness profile of the distal shaft section 46 is less than the lateral stiffness profile of the proximal shaft section 42, while the bendable shaft section 44 has a transitioning lateral stiffness profile that transitions the higher lateral stiffness profile of the proximal shaft section 42 to the lower lateral stiffness profile of the distal shaft section 46, as illustrated in FIGS. 3A and 3B. In this manner, the bendable shaft section 44 facilitates tracking of the distal tip 48 through the bronchial airways and parenchyma of the lung. That is, in the absence of the bendable shaft section 44, the distal shaft section 46 may "snow plow" and not follow itself, possibly creating tissue damage and making it difficult to track the distal tip 48 to the SPN. Although the lateral stiffness profile of the distal shaft section 46 is less than the lateral stiffness profile of the proximal shaft section 42, the lateral stiffness profile of the distal shaft section 46 is preferably high enough to provide stability to the distal shaft section 46 when locating the distal tip 48 at a sampling site of a selected SPN, and to facilitate taking of a biopsy at the sampling site of the selected SPN.

As will be described in further detail below, the lateral stiffness profiles of the proximal shaft section 42, bendable shaft section 44, and distal shaft section 46 may be accomplished using different techniques. Furthermore, the transition between the lateral stiffness profiles of the proximal shaft section 42 and the distal shaft section 46 may also be accomplished using different techniques.

In the exemplary embodiments illustrated in FIGS. 3A and 3B, the lateral stiffness profiles of the proximal shaft section 42 and the distal shaft section 46 are uniform, although in alternative embodiments, either or both of the lateral stiffness profiles of the proximal shaft section 42 and the distal shaft section 46 may be non-uniform. The transitioning lateral stiffness profile of the bendable shaft section 44 may either be gradual (FIG. 3A), such that it transitions the higher lateral stiffness profile of the proximal shaft section 42 to the lower lateral stiffness profile of the distal shaft section 46 in a gradual fashion, or uniform (FIG. 3B), such that it transitions the higher lateral stiffness profile of the proximal shaft section 42 to the lower lateral stiffness profile of the distal shaft section 46 in a gradual fashion in a step-wise fashion.

Figure 3C:
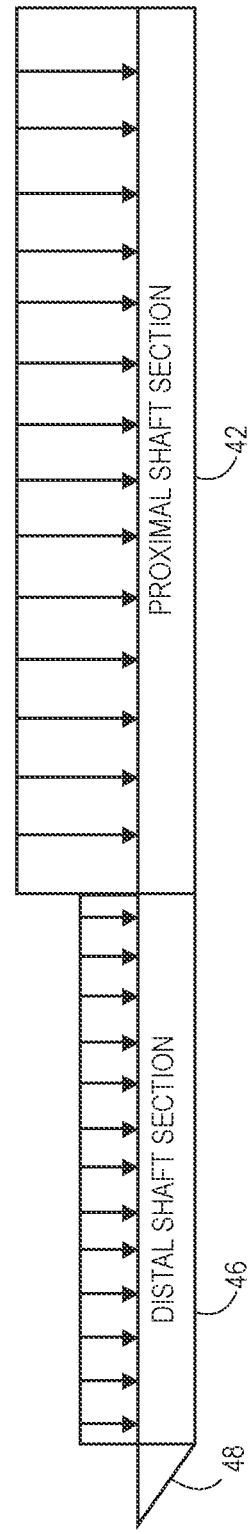
FIG. 3C is a plan view of still another lateral stiffness profile of an elongated shaft of the pulmonary access device of FIG. 2A.

In an alternative embodiment illustrated in FIG. 3C, the bendable shaft section 44 does not transition the higher lateral stiffness profile of the proximal shaft section 42 to the lower lateral stiffness profile of the distal shaft section 46. Instead, bendable shaft section 44 has the same lateral stiffness profile as that of the distal shaft section 46, and thus, the higher lateral stiffness profile of the proximal shaft section 42 is immediately transitioned to the lower lateral stiffness profiles of the bendable shaft section 44 and the distal shaft section 46 in a step-wise fashion.

In this exemplary embodiment, the distal tip 48 takes the form of a tissue-penetrating distal tip. In contrast to asymmetrical distal tips, which may create bias in steering when traversing tissue, and in this case, the parenchyma, the tissue-penetrating distal tip 48 is bi-laterally symmetrical relative to a longitudinal axis of the elongated shaft 40, thereby facilitating uniform and predictable steering of the distal shaft section 46 through the parenchyma. For example, as best illustrated in FIGS. 4A and 4B, the tissue-penetrating distal tip 48 tapers to a point that is coincident with a longitudinal axis 54 of the elongated shaft 40. Preferably, the taper of the tissue-penetrating distal tip 48 aligns perpendicularly to the plane of deflection of the distal shaft section 46. In an alternative embodiment, the elongated shaft 40 has an atraumatic distal tip 48', as illustrated in FIG. 5.

The pulmonary access device 14 further comprises a profiled stylet 56 configured for being disposed in the working channel 50 of the elongated shaft 40. As best shown in FIG. 6, the profiled stylet 56 has a proximal stylet section 58, an intermediate stylet section 60, and a distal stylet section 62. As illustrated in FIGS. 2A-2C, the profiled stylet 56 further comprises a stylet hub 63 affixed to the end of the proximal stylet section 58. One embodiment of a stylet 56*a* has a circular cross-section (FIG. 6A). Another embodiment of a stylet 56*b* has a rectangular cross-section (FIG. 6B). In this embodiment, the smaller dimension of the rectangular cross-section (i.e., the dimension with decreased bending stiffness) may be aligned with the steering directionality (in this case, of uni-directional or bi-directional steering), thereby facilitating bending of the bendable shaft section 44 in the proper steering plane. In this case, the stylet 56*b* may be keyed with the elongated shaft 40 to facilitate proper rotational orientation of the stylet 56*b* within the channel 50. In still another embodiment, the stylet 56*c* may have a generally rectangular cross-section with rounded edges (FIG. 6C). For example, the top and bottom surfaces of a cylindrical rod may be ground flat to achieve decreasing bending stiffness in the plane of bending.

As illustrated in FIG. 7, when the profiled stylet 56 is disposed in the working channel 50 of the elongated shaft 40, the proximal stylet section 58, intermediate stylet section 60, and distal stylet section 62 respectively axially align with the proximal shaft section 42, bendable shaft section 44, and distal shaft section 46. In the alternative embodiment where the elongated shaft 40 does not include a transition shaft section (see FIG. 3C), the proximal stylet section 58 and intermediate stylet section 60 will be aligned with the distal shaft section 46 (e.g., the proximal stylet section 58 and intermediate stylet section 60 will collectively extend along the length of the distal shaft section 46).

Figure 8A:
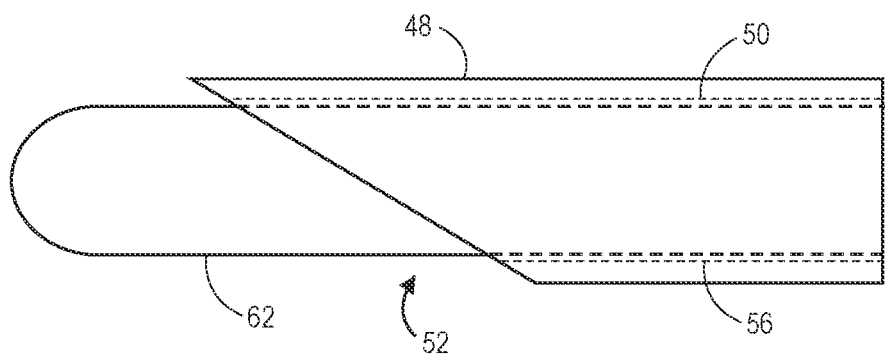
FIGS. 8A-8C are profile views of one embodiment of a profiled stylet in different positions relative to the tissue-penetrating distal tip of FIGS. 4A-4B.
Figure 8B:
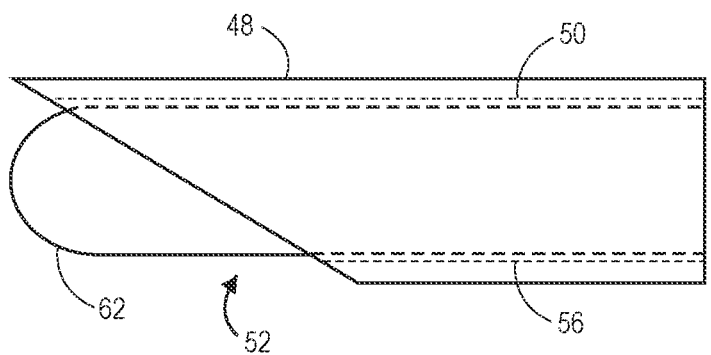
Figure 8C:
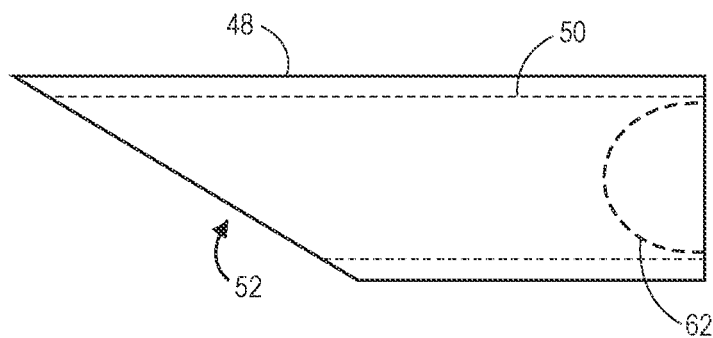

In the exemplary embodiment illustrated in FIG. 8A-8C, the distal stylet section 62 is atraumatic and blocks the distal opening 52 in the tissue-penetrating distal tip 48. In this manner, the profiled stylet 56 serves as an obturator for pulmonary access device 14. For example, when navigating through the bronchial airways, the distal stylet section 62 may extend distally past the tissue-penetrating distal tip 48 (see FIG. 8A), thereby shielding the tissue along the bronchial airways from being damaged by the tissue-penetrating distal tip 48. When puncturing through a bronchial airway into the parenchyma, and tracking the parenchyma to the SPN, the distal stylet section 62 may be slightly retracted within the tissue-penetrating distal tip 48 until the distal stylet section 62 is axially aligned with, or proximal to, the tissue-penetrating distal tip 48 (see FIG. 8B), thereby allowing the tissue-penetrating distal tip 48 to puncture and traverse tissue, without coring the tissue. When taking a biopsy sample from the SPN, the distal stylet section 62 may be further retracted within the tissue-penetrating distal tip 48 (see FIG. 8C), thereby creating sufficient displace in the distal end of the channel 50 for coring the SPN.

Figure 9A:
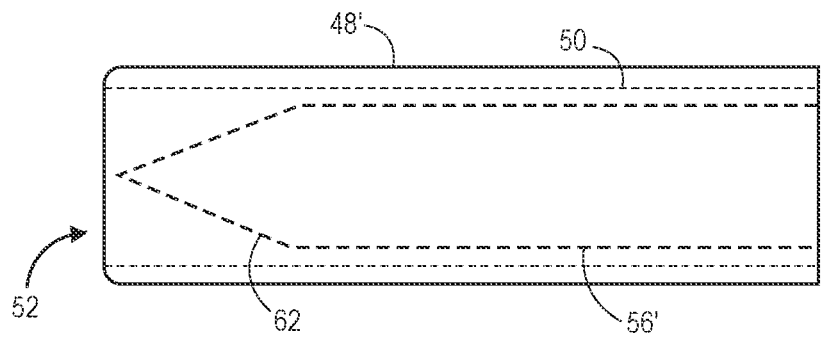
FIGS. 9A-9C are profile views of another embodiment of a profiled stylet in different positions relative to the atraumatic distal tip of FIG. 5.
Figure 9B:
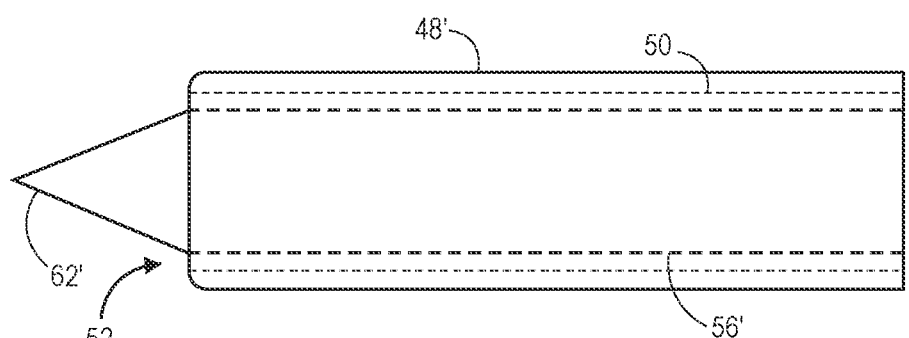
Figure 9C:
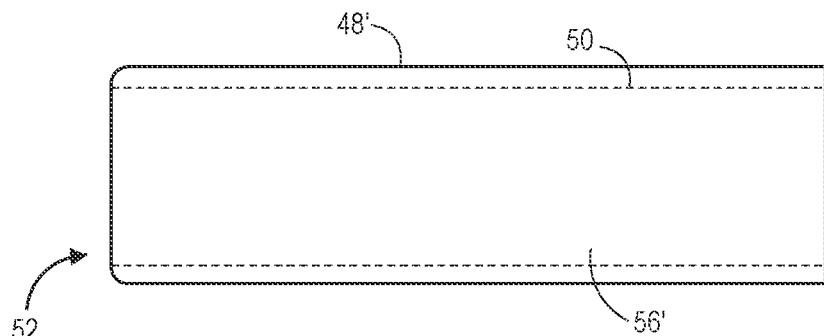

In the embodiment illustrated in FIGS. 9A-9C, wherein the elongated shaft 40 has an atraumatic distal tip 48', an alternative embodiment of a profiled stylet 56' has a tissue-penetrating distal stylet section 62'. For example, when navigating through the bronchial airways, the distal stylet section 62' may be retracted within the tissue-penetrating distal tip 48' (see FIG. 9A), thereby shielding the tissue along the bronchial airways from being damaged by the atraumatic distal tip 48'. When puncturing through a bronchial airway into the parenchyma, and tracking the parenchyma to the SPN, the tissue-penetrating distal stylet section 62' may be distally extended from the atraumatic distal tip 48' (see FIG. 9B), such that the tissue-penetrating distal stylet section 62' may puncture the tissue, and allow the atraumatic distal tip 48' to traverse tissue, without coring the tissue. When taking a biopsy sample from the SPN, the profiled stylet 56' may be completely removed from the channel 50 (see FIG. 9C) and replaced with a separate biopsy tool (not shown) for taking a biopsy of the SPN.

In either of the embodiments illustrated in FIGS. 8A-8C or FIGS. 9A-9C, the lateral stiffness profile of the proximal stylet section 58 and distal stylet section 62 are the same, while the lateral stiffness profile of the intermediate stylet section 60 is less than the lateral stiffness profiles of the proximal stylet section 58 and distal stylet section 62. In the exemplary embodiment illustrated in FIGS. 6 and 7, the intermediate stylet section 60 has a geometric profile that is less than the geometric profile of the proximal and distal stylet sections 58, 62, such that the lateral stiffness profile of the intermediate stylet section 60 is less than the lateral stiffness profiles of the proximal and distal stylet sections 58, 62. In this exemplary embodiment, the geometric profiles of the proximal stylet section 58, intermediate stylet section 60, and distal stylet section 62 are circular cross-sections, in which case, the diameter of the intermediate stylet section 60 is less than the diameters of the proximal and distal stylet sections 58, 62.

In the case where the pulmonary access device 14 serves as a biopsy needle, the profiled stylet 56 may be pulled back within the channel 50 (or alternatively, the pulmonary access device 14 may be distally advanced relative to the profiled stylet 56), such that the distal tip 48 may core a biopsy sample from the SPN, which biopsy sample may be retained in the distal end of the channel 50. The profiled stylet 56 may then be pushed back to dislodge the biopsy sample from the channel 50, which can be subsequently analyzed. In the case where the pulmonary access device 14 serves as a channel device (e.g., the embodiment illustrated in FIG. 9C), the profiled stylet 56 may be completely removed from the channel 50, such that a separate biopsy tool may be introduced through the channel 50 to take biopsy samples from the SPN.

Figure 2D:
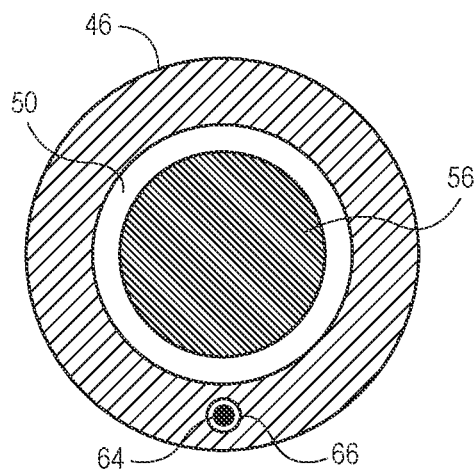
FIG. 2D is a cross-sectional view of one variation of the pulmonary access device of FIG. 2A, taken along the line 2D-2D.
Figure 2E:
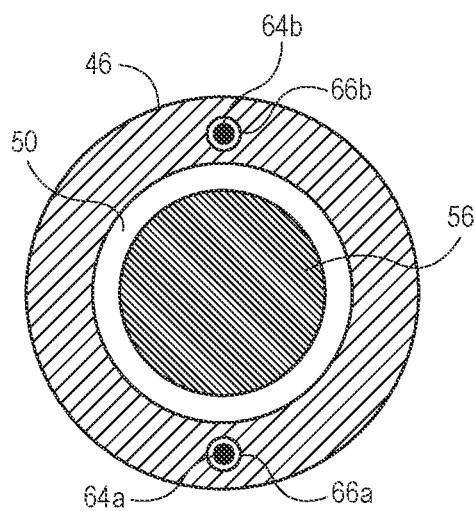
FIG. 2E is a cross-sectional view of another variation of the pulmonary access device of FIG. 2A, taken along the line 2E-2E.

Referring specifically to FIG. 2D, the pulmonary access device 14 further comprises a pull wire 64 affixed to the distal shaft section 46. In the exemplary embodiment, the pull wire 64 is housed within a pull wire lumen 66 extending through the proximal shaft section 42 and bendable shaft section 44, and into the distal shaft section 46. Thus, when the pull wire 64 is tensioned, the bendable shaft section 44 bends, thereby deflecting the distal shaft section 46 relative to the proximal shaft section 42, as illustrated in FIG. 2B. In an alternative embodiment illustrated in FIG. 2E, the pulmonary access device 14 comprises two pull wires 64 that are clocked from each other 180 degrees and affixed to the distal shaft section 46. In the exemplary embodiment, the pull wires 64a, 64b are respectively housed within two pull wire lumens 66a, 66b extending through the proximal shaft section 42 and bendable shaft section 44, and into the distal shaft section 46. Thus, when the pull wire 64a is tensioned, the bendable shaft section 44 bends, thereby deflecting the distal shaft section 46 relative to the proximal shaft section 42 in first direction. In contrast, when the pull wire 64b is tensioned, the bendable shaft section 44 bends, thereby deflecting the distal shaft section 46 relative to the proximal shaft section 42 in the opposite direction.

In one embodiment, the maximum bend of the bendable shaft section 44 is at least 180 degrees, thereby deflecting the distal shaft section 46 a maximum of at least 180 degrees relative to the proximal shaft section 42. In this manner, the deflection strength of the distal shaft section 46, when in the tissue of the patient, and in this case when in the parenchyma of the lung, is increased, thereby increasing the number of sites that can be sampled. In alternative embodiments, the maximum bend of the bendable shaft section 44 is less than 180 degrees (e.g., 90 degrees), thereby deflecting the distal shaft section 46 a maximum of less than 180 degrees (e.g., 90 degrees) relative to the proximal shaft section 42.

Significantly, since the intermediate stylet section 60 is aligned with the bendable shaft section 44 of the elongated shaft 40 when fully introduced into the channel 50 of the pulmonary access device 14, as illustrated in FIG. 7, bending of the bendable shaft section 44, and thus, deflection of the distal shaft section 46, is facilitated by the relatively low lateral stiffness of the intermediate stylet section 60. As will be described in further detail below, selective deflection of the distal shaft section 46 allows the pulmonary access device 14 to be actively steered to the SPN and located at various sites of the SPN, thereby maximizing the diagnostic yield of the biopsy. Furthermore, when coring the biopsy samples, deflection of the distal shaft section 46 allows a biopsy sample that is cored within the channel 50 to be sheer off ("bite-off") or twist off the cored biopsy sample to separate it from the SPN. In contrast, a non-steerable distal tip must be cycled back and forth along an axis to core the sample, which may result in difficulty detaching the cored sample from the SPN.

Although the distal shaft section 46 has been described and illustrated as only being capable of deflecting in a single direction, such that the pulmonary access device 14 is enabled with uni-directional steerability, it should be appreciated that the pulmonary access device 14 may be modified to allow the distal shaft section 46 to be selectively deflected in one of a plurality of different directions. For example, the pulmonary access device 14 may comprise two pull wires and two associated pull wire lumens that are clocked 180 degrees from each other to allow the distal shaft section 46 to be deflected in opposite directions, thereby enabling the pulmonary access device 14 with bi-directional steerability. As another example, the pulmonary access device 14 may comprise two pull wires and two associated pull wire lumens that are clocked less than 180 degrees from each other (e.g., 90 degrees) to allow the distal shaft section 46 to be deflected out-of-plane to create complex curves.

Referring to FIGS. 2A-2C, the pulmonary access device 14 further comprises a handle assembly 68 affixed to the proximal shaft section 42. The handle assembly 68 includes a handle body 70, which is preferably shaped to be ergonomic for grasping with one hand by the physician. The handle body 46 may be composed of a suitable polymer, such as, e.g., acrylonitrile butadiene styrene (ABS), polyvinylchloride, polycarbonate, polyolefins, polypropylene, polyethylene, etc. The handle assembly 68 further includes a stylet port 71 through which the stylet 56 may be introduced into the channel 50 of the elongated shaft 40. In one embodiment, the handle assembly 68 includes a luer connector (not shown) that can affix the stylet 56 relative to the elongated shaft 40. Thus, the position of the stylet 56 within the channel 50 may be affixed by tightening the luer connector. In an optional embodiment, the stylet 56 may be removed from the channel 50, and an aspiration/suction system can be connected in fluid connection with the channel 50 via the luer connector.

The handle assembly 68 further includes a deflection control actuator 72 affixed to the handle body 70. The deflection control actuator 72 is operably connected to the pull wire 64, such that the pull wire 64 may be alternately tensioned via manual manipulation of the deflection control actuator 72, thereby bending the bendable shaft section 44 (see FIG. 2C), and relaxed via manual manipulation of the deflection control actuator 72, thereby allowing the resiliency of the elongated shaft 40 to straighten, or at least reduce the bend in, the bendable shaft section 44 (see FIG. 2A).

The handle assembly 68 further includes a shaft displacement actuator 74 affixed to the handle body 70. The shaft displacement actuator 74 is operably connected to the proximal shaft section 42, such that the elongated shaft 40 may be rotated about its longitudinal axis 54 relative to the handle body 70 via manual manipulation of the shaft displacement actuator 74, thereby rotating the deflected distal shaft section 46 about the longitudinal axis 54. As a result, the distal tip 48 of the deflected distal shaft section 46 may be located at different circumferential positions about the longitudinal axis 54. The shaft displacement actuator 74 is also operably connected to the proximal shaft section 42, such that the elongated shaft 40 may be linear displaced along the longitudinal axis 54 relative to the handle body 70 via manual manipulation of the shaft displacement actuator 74, thereby linearly translating the distal shaft section 46 along the longitudinal axis 54. In this manner, the distal shaft section 46 may be alternately deployed from the distal end 20 of the elongated shaft 16 of the bronchoscope 12 (see FIG. 2B) and retracted into the distal end 20 of the elongated shaft 16 of the bronchoscope 12 (see FIG. 2A).

Figure 10:
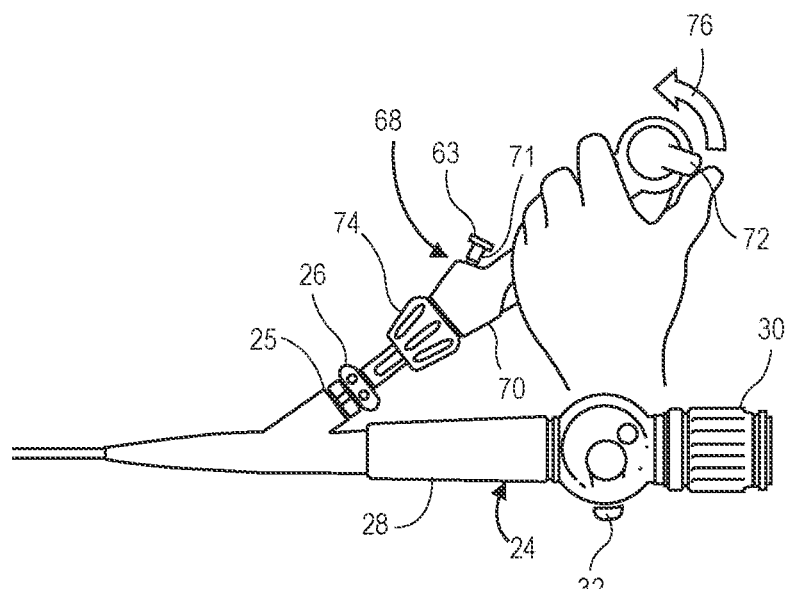
FIG. 10 is a perspective view of one embodiment of handle assemblies of a bronchoscope and pulmonary access device of the transbronchial pulmonary biopsy system of FIG. 1, particularly showing manipulation of a deflection control actuator located on the handle assembly of the pulmonary access device.
Figure 11:
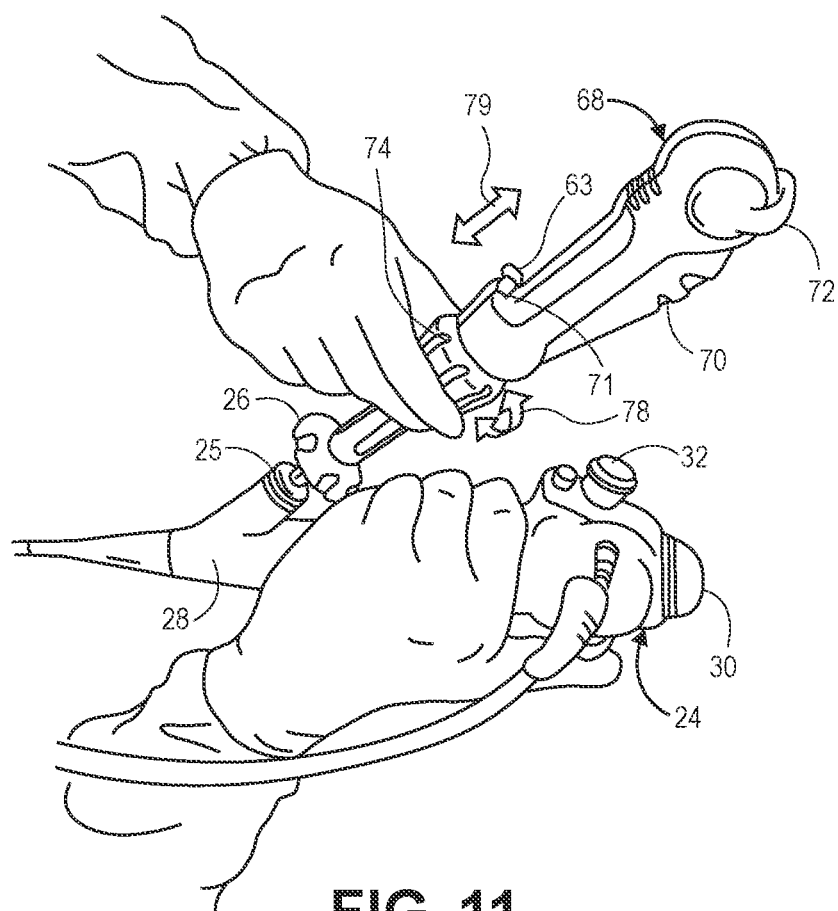
FIG. 11 is a perspective view of the handle assemblies of FIG. 10, particularly showing manipulation of a shaft displacement actuator located on the handle assembly of the pulmonary access device.

In the embodiment illustrated in FIG. 2A-2C, the deflection control actuator 72 takes the form of a dial that can be manually rotated about the arrow 76 by the thumb of the physician in one direction to tension the pull wire 64, and either manually rotated by the thumb of the physician in the other opposite direction, or simply released, to relax the pull wire 64, as illustrated in FIG. 10. The deflection control actuator 72 may be locked in one or more positions, such that the tension on the pull wire 64, and thus the bend in the bendable shaft section 44, is maintained when the physician releases the deflection control actuator 72, and unlocked to relax the pull wire 64 and straighten the bendable shaft section 44. In the embodiment illustrated in FIGS. 2A-2C, the shaft displacement actuator 74 takes the form of a collar that can be grasped between the thumb and finger of the physician and manually rotated about the arrow 78 to rotate the deflected distal shaft section 46 about the longitudinal axis 54 and/or linearly translated along the arrow 79 to linearly translate the distal shaft section 46 along the longitudinal axis 54, as illustrated in FIG. 11.

Figure 12:
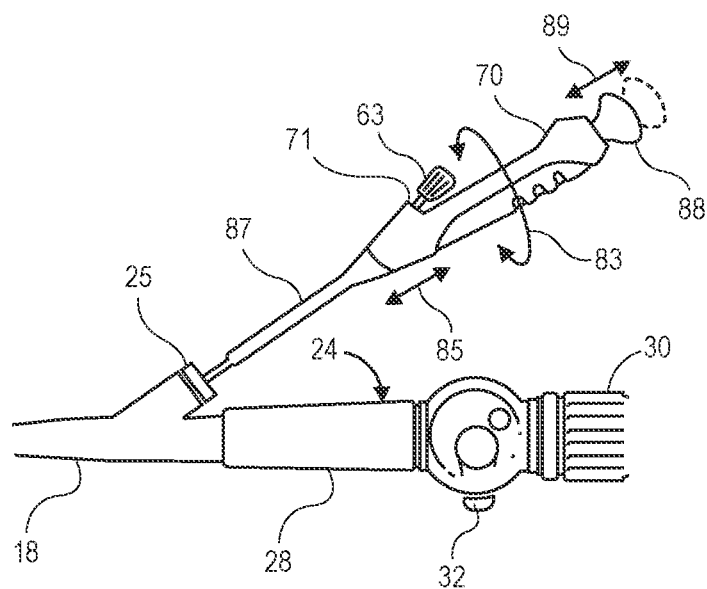
FIG. 12 is a perspective view of another embodiment of handle assemblies of a bronchoscope and pulmonary access device of the transbronchial pulmonary biopsy system of FIG. 1.
Figure 13:
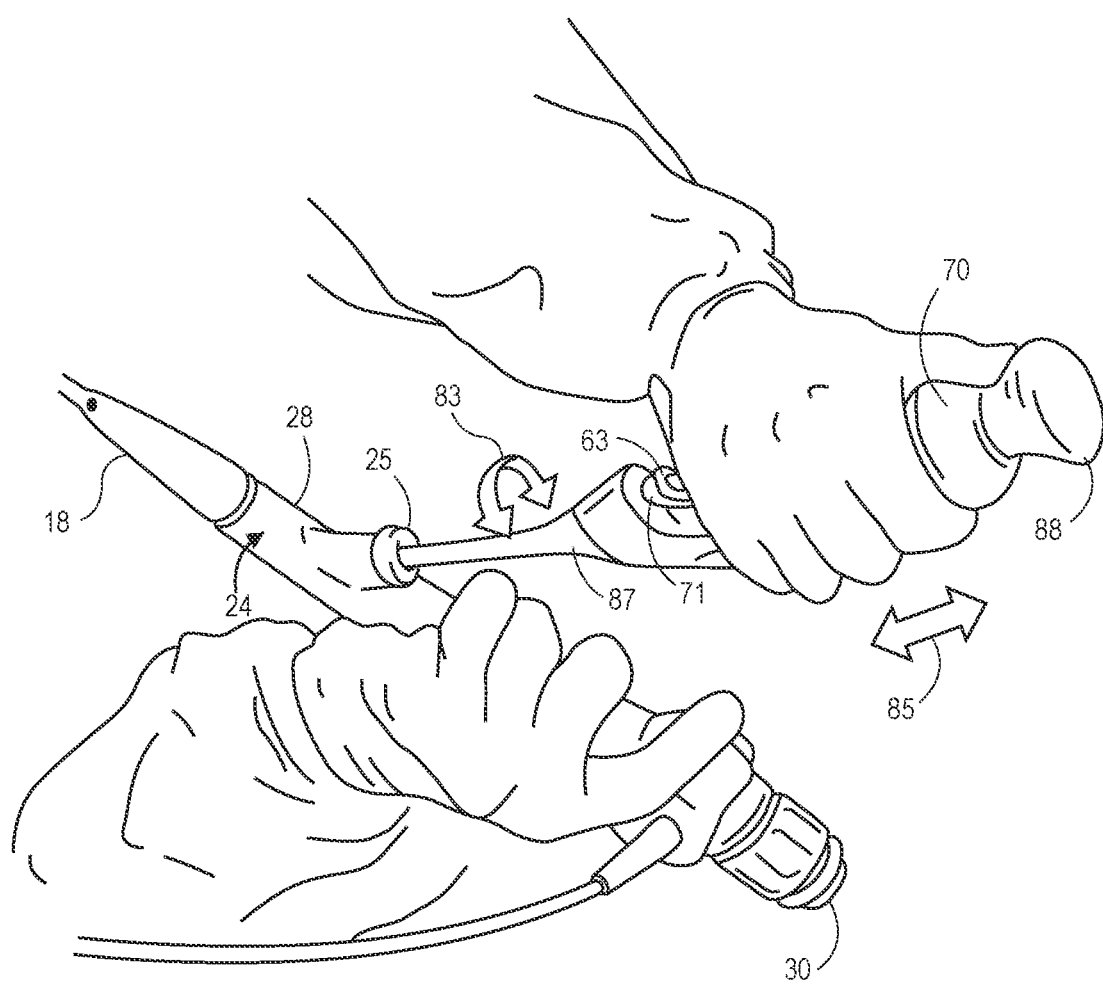
FIG. 13 is a perspective view of the handle assemblies of FIG. 12, particularly showing manipulation of the handle assembly of the pulmonary access device.

As briefly discussed above, the pulmonary access device 14 may alternatively not be locked within the working channel 22 of the bronchoscope 12, and thus, may be freely displaced relative to the working channel 18 of the bronchoscope 12, as illustrated in handle assembly 68' of FIG. 12. In this case, a shaft displacement actuator is not required, and instead, the handle body 70 may simply be rotated about arrow 83 relative to the bronchoscope 12 to rotate the deflected distal shaft section 46 about the longitudinal axis 54 and/or linearly displaced along the arrow 85 relative to the bronchoscope 12 to linearly displace the distal shaft section 46 along the longitudinal axis 54, as illustrated in FIG. 13. In this alternative embodiment, the pulmonary access device 14 further includes a strain relief sleeve 87 affixed around the exposed region of the proximal shaft section 42.

Figure 14C:
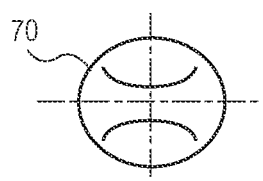
FIG. 14C is an axial view of the deflection control actuator of FIG. 14A.
Figure 14A:
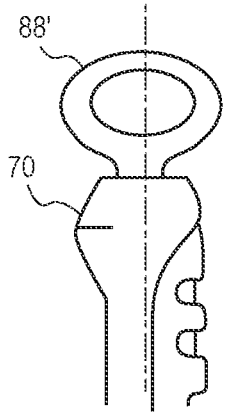
FIG. 14A is a plan view of one variation of a deflection control actuator of the handle assembly of the pulmonary access device of FIG. 12, particularly showing the deflection control actuator in one position.
Figure 14B:
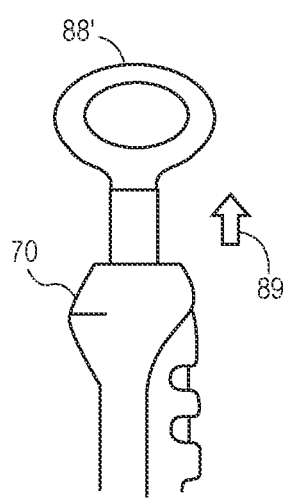
FIG. 14B is a plan view of the deflection control actuator of FIG. 14A, particularly showing the deflection control actuator in another position.

The handle assembly 68' in this alternative embodiment may include a deflection control actuator 88 that takes the form of a plunger that can be manually axially pulled with a finger of the physician to tension the pull wire 64, and either manually axially pushed with the finger or thumb of the physician, or simply released, to relax the pull wire 64. One variation of the deflection control actuator 88 illustrated in FIGS. 14A-14C may take the form of a finger ring 88' that can be manually axially pulled with a finger of the physician along the arrow 89 to tension the pull wire 64 (FIG. 14A) and manually axially pushed with the finger or thumb of the physician, or simply released, to relax the pull wire 64 (FIG. 14B).

Although the pulmonary access device 14 has been described as being capable of manually manipulated via the handle assembly 68, it should be appreciated that the pulmonary access device 14 may form a portion of a robotic medical system, in which case, the elongated shaft 40 of the pulmonary access device 14 may be operably connected to a robotic actuation of the robotic medical system.

Referring now to FIGS. 15 and 16, one specific embodiment of a pulmonary access device 14' will be described. In this embodiment, the lateral stiffness profiles of the proximal shaft section 42 and the distal shaft section 46 are uniform (with the lateral stiffness profile of the distal shaft section 46 being less than the lateral stiffness profile of the proximal shaft section 42), and the transitioning lateral stiffness profile of the bendable shaft section 44 is gradual, such that it transitions the higher lateral stiffness profile of the proximal shaft section 42 to the lower lateral stiffness profile of the distal shaft section 46 in a gradual fashion, as illustrated in FIG. 3A.

The elongated shaft 40 of the pulmonary access device 14' comprises a proximal tube 80 extending along the proximal shaft section 42, and a distal tube 82 extending along the bendable shaft section 44 and the distal shaft section 46. The proximal tube 80 can be composed of a metal to facilitate axial and torque transmission along the proximal shaft section 42. For example, the proximal tube 80 may be composed of a multi-strand wound stainless steel wire construction designed to maximize torque transmission in either rotational direction while maximizing axial compression resistance to enable efficient steering.

In contrast, the distal tube 82 can have a more flexible construction. In the illustrated embodiment, the distal tube 82 is composed of a very thin malleable polymeric material (e.g., expanded polytetrafluoroethylene (ePTFE)), thereby providing lateral flexibility along the bendable shaft section 44 and the distal shaft section 46 relative to the proximal shaft section 42. Alternatively, the distal tube 82 may have a metallic construction (e.g., a metallic coil or a laser cut metallic tube). In an optional embodiment, the proximal tube 80 and distal tube 82 are radiopaque to enable visualization of the pulmonary access device 14' under fluoroscopy. For example, the metallic nature of the proximal tube 80, and if applicable the distal tube 82, inherently provides radiopaqueness to the pulmonary access device 14'. In the case where the proximal tube 80 is polymeric, the polymer may be loaded within radiopaque particles, such as tungsten or bismuth.

The proximal tube 80 and distal tube 82 may be affixed to each other in any suitable manner. For example, the proximal tube 80 and distal tube 82 may be affixed to each other via a lap joint. In the illustrated embodiment, the distal end of the proximal tube 80 has a reduced diameter, such that the proximal end of the distal tube 82 may be fitted over the reduced distal end of the proximal tube 80 and bonded together.

In this embodiment, the distal tip 48 of the pulmonary access device 14' is a tissue-penetrating distal tip. To this end, the distal tip 48 of the pulmonary access device 14' takes the form of a coring needle 84 composed of a suitably rigid material, such as stainless steel, that is affixed to the distal end of the distal tube 82. The pull wire lumen 66 extends through the walls of the proximal tube 80 and distal tube 82, terminating at the coring needle 84. The distal end of the pull wire 64 extending through the pull wire lumen 66 is attached to the coring needle 84 using suitable means, e.g., soldering or welding. In an alternative embodiment, the distal tip 48 of the pulmonary access device 14' may be an atraumatic distal tip, in which case, the distal end of the distal tube 82 may serve as the atraumatic distal tip 48. In an alternative embodiment, the atraumatic metal distal tip is a distinct element that is affixed to the distal end of the distal tube 82.

In this embodiment, the pulmonary access device 14' further comprises a steering plate 86 having a rectangular cross-section affixed within the elongate shaft 40 along the bendable shaft section 44 and distal shaft section 46. The steering plate 86 may be composed, e.g., a high yield strength spring steer (17-7 PH®). In one embodiment, the steering plate 86 is embedded in the distal tube 82. In an alternative embodiment, the steering plate 86 may reside within a separate polymeric tube. The lateral stiffness profile of the combination of the distal tube 82 and the steering plate 86 extending along the distal shaft section 46 is less than the lateral stiffness profile of the proximal tube 80 extending along the proximal shaft section 42. As best illustrated in FIG. 17A, the steering plate 86 has a geometric profile along the longitudinal axis 54 of the elongated shaft 40 that tapers down in the distal direction along the bendable shaft section 44, such that the steering plate 86 transitions the higher lateral stiffness profile of the proximal shaft section 42 to the lower lateral stiffness profile of the distal shaft section 46 in a gradual manner, as illustrated in FIG. 3A.

Thus, as discussed above, the steering plate 86 transitions the higher lateral stiffness of the proximal shaft section 42 to the lower lateral stiffness of the distal shaft section 46, thereby facilitating tracking of the distal tip 48 through the bronchial airways and parenchyma of the lung. In the illustrated embodiment, the pull wire 64 is affixed to the coring needle 84 circumferentially opposite to the steering plate 86 to minimize the steering force required to deflect the distal shaft region 46 of the elongated shaft 40.

In an alternative embodiment illustrated in FIG. 17B, a steering plate 86' has a uniform geometric profile along its length, such that there is no transition between the higher lateral stiffness profile of the proximal shaft section 42 and the lower lateral stiffness profile of the distal shaft section 46. In this case, the elongated shaft 40 does not have a transition section, but instead, the higher lateral stiffness profile of the proximal shaft section 42 is immediately transitioned to the distal shaft section 42 in a step-wise manner, as illustrated in FIG. 3C.

Figure 18:
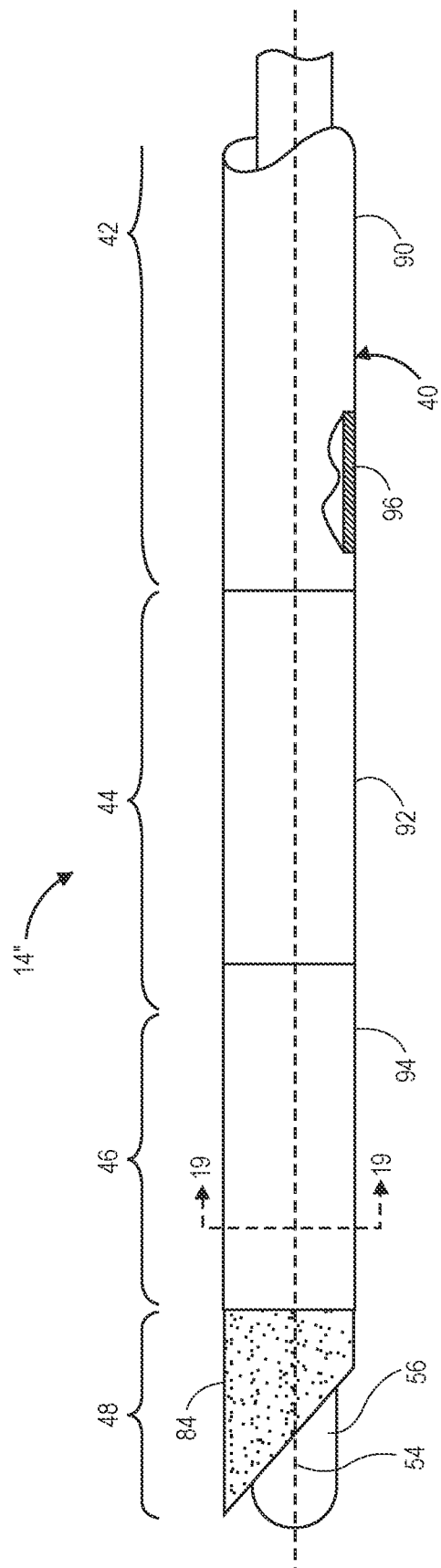
FIG. 18 is a partially-cutaway profile view of another specific embodiment of the pulmonary access device of FIG. 2A.
Figure 19:
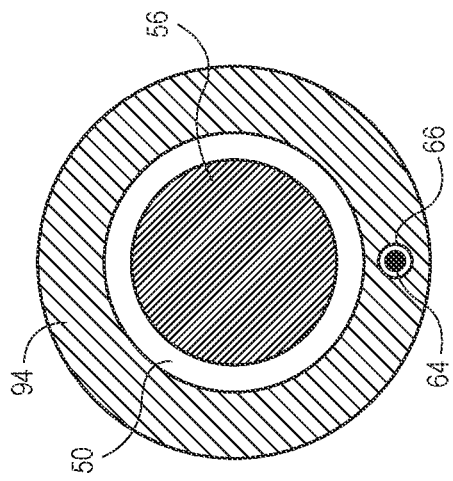
FIG. 19 is a cross-sectional view of the pulmonary access device of FIG. 18, taken along the line 19-19.
Figure 20:
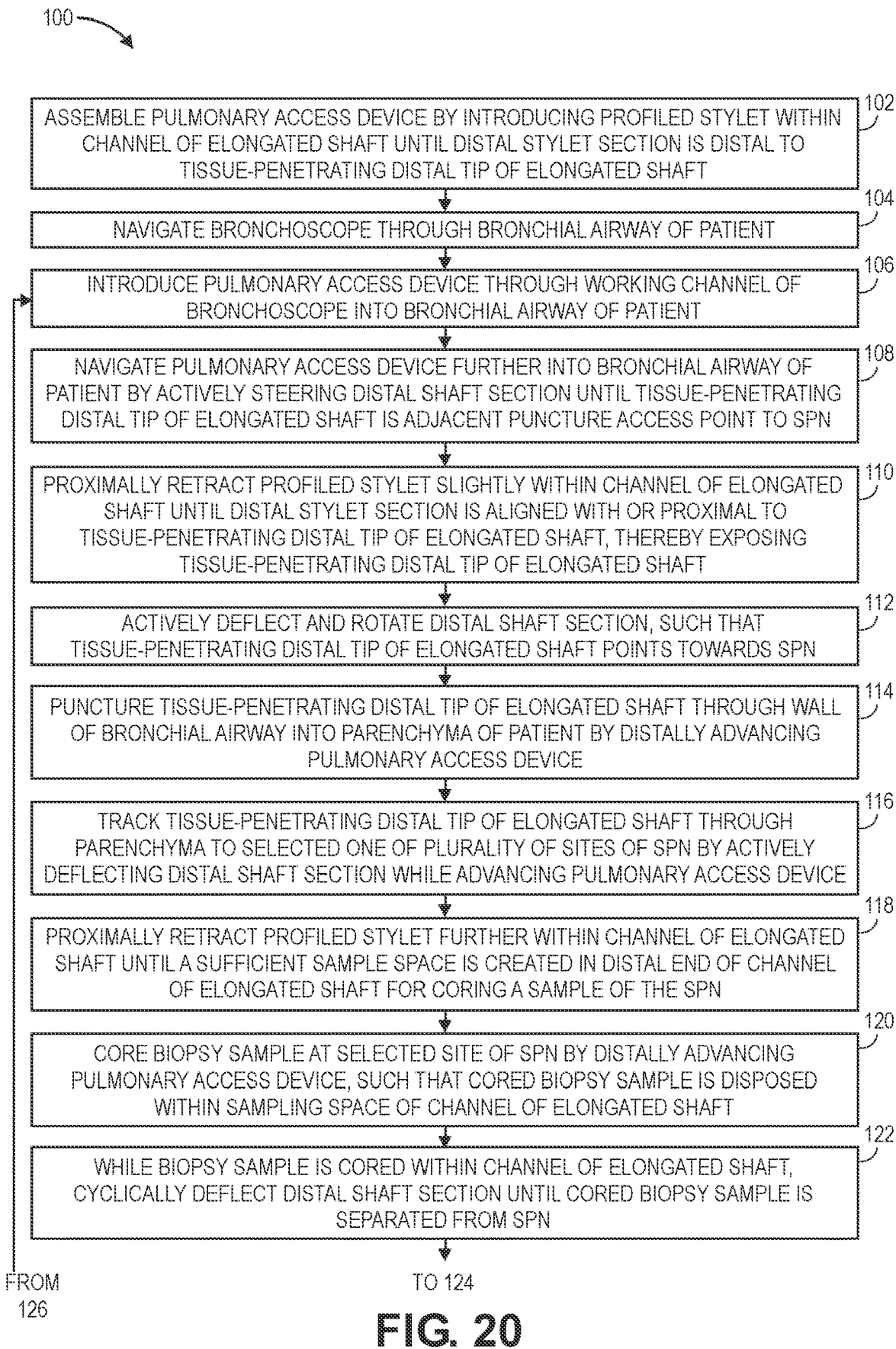
FIG. 20 is a flow diagram of one method of operating the transbronchial pulmonary biopsy system to take biopsy samples from a solitary pulmonary nodule (SPN) of a patient.
Figure 20:
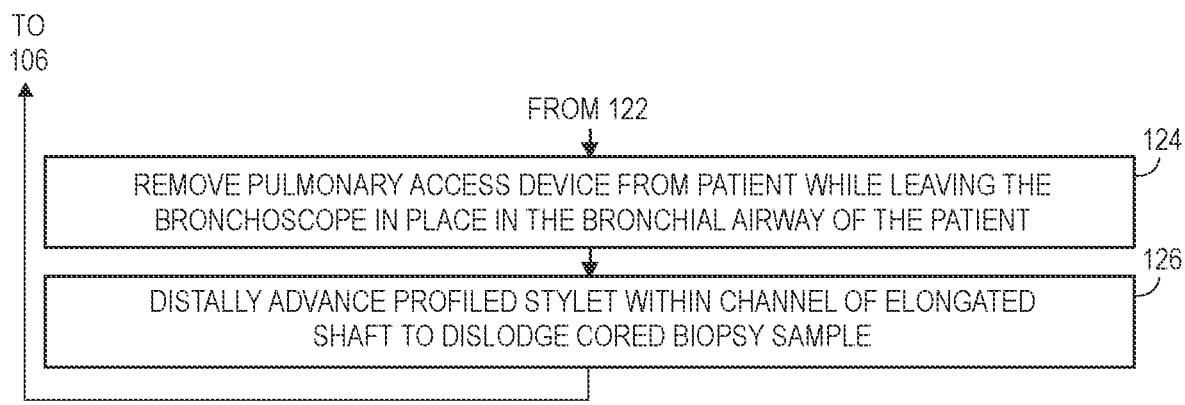

Referring now to FIGS. 18 and 19, another specific embodiment of a pulmonary access device 14" will be described. In this embodiment, the lateral stiffness profile of the proximal shaft section 42 is uniform, and the distal shaft section 46 is uniform (with the lateral stiffness profile of the distal shaft section 46 being less than the lateral stiffness profile of the proximal shaft section 42), and the transitioning lateral stiffness profile of the bendable shaft section 44 is uniform, such that it transitions the higher lateral stiffness profile of the proximal shaft section 42 to the lower lateral stiffness profile of the distal shaft section 46 in a step-wise fashion, as illustrated in FIG. 3B.

The elongated shaft 40 of the pulmonary access device 14" comprises a proximal polymeric tube 90 extending along the proximal shaft section 42, an intermediate polymeric tube 92 extending along the bendable shaft section 44, and a distal polymeric tube 94 extending along the distal shaft section 46. The polymeric tubes 90-94 may be composed of, e.g., nylon, Pebax® elastomer, polyurethane, or a laminate design. In the illustrated embodiment the proximal polymeric tube 90 has a relatively high durometer (e.g., 90D), the intermediate polymeric tube 92 has a relatively medial durometer (e.g., 72D), and the distal polymeric tube 94 has a relatively low durometer (e.g., 55D). In one embodiment, the polymeric tubes 90-94 may be reinforced with a uniform braid (e.g., 0.001"×0.003" flat wire composed of a stainless steel braid of 55 picks per inch (ppi)) to resist both compression and torsional loss.

Thus, the lateral stiffness profile of the distal polymer tube 94 extending along the distal shaft section 46 is less than the lateral stiffness profile of the proximal polymer tube 90 extending along the proximal shaft section 42, while the transition polymer tube 92 transitions the higher lateral stiffness profile of the proximal shaft section 42 to the lower lateral stiffness profile of the distal shaft section 46 in step-wise manner, as illustrated in FIG. 3B. In an optional embodiment, the proximal polymer tube 90, intermediate polymer tube 92, and distal polymer tube 94 may be loaded with radiopaque particles, such as tungsten or bismuth, to provide radiopacity to the pulmonary access device 14".

The proximal polymer tube 90, intermediate polymer tube 92, and distal polymer tube 94 may be affixed to each other in any suitable manner. For example, the proximal polymer tube 90, intermediate polymer tube 92, and distal polymer tube 94 may be affixed to each other via lap joints. In the illustrated embodiment, the distal end of the proximal polymer tube 90 has a reduced diameter, such that the proximal end of the intermediate polymer tube 92 may be fitted over the reduced distal end of the proximal polymer tube 80 and bonded together. Likewise, the distal end of the intermediate polymer tube 92 has a reduced diameter, such that the proximal end of the distal polymer tube 94 may be fitted over the reduced distal end of the intermediate polymer tube 92 and bonded together. In an alternative embodiment, the proximal polymer tube 90, intermediate polymer tube 92, and distal polymer tube 94 may be affixed to each other via butt bonds.

In this embodiment, the distal tip 80 of the pulmonary access device 14" is tissue-penetrating distal tip. To this end, the pulmonary access device 14' takes the form of a coring needle 84 composed of a suitably rigid material, such as stainless steel, that is affixed to the distal end of the distal polymer tube 84. The pull wire lumen 66 extends through the walls of the proximal polymer tube 90, intermediate polymer tube 92, and distal polymer tube 94, terminating at the coring needle 96. The distal end of the pull wire 64 extending through the pull wire lumen 66 is attached to the coring needle 96 using suitable means, e.g., soldering or welding. In an alternative embodiment, the distal tip 80 of the pulmonary access device 14" may be an atraumatic distal tip, in which case, the distal end of the distal polymer tube 94 may serve as the atraumatic distal tip 80. In this embodiment, a compression coil 96 (e.g., a tightly wound steer coil) may be provided over the pull wire 64 to provide additional compression resistance to the proximal polymer tube 90, intermediate polymer tube 92, and distal polymer tube 94.

In an alternative embodiment, the elongated shaft 40 of the pulmonary access device 14" does not have an intermediate polymer tube 92, such that there is no transition between the higher lateral stiffness profile of the proximal shaft section 42 and the lower lateral stiffness profile of the distal shaft section 46. In this case, the higher lateral stiffness profile of the proximal shaft section 42 will be immediately transitioned to the distal shaft section 42 in a step-wise manner, as illustrated in FIG. 3C.

Referring to FIGS. 20 and 21A-21H, one exemplary method 100 of using the transbronchial pulmonary biopsy system 10 to take biopsy samples from different sites of an SPN located in the parenchyma P of a patient will now be described. In this method, the pulmonary access device 14 serves as a biopsy needle comprising the elongated shaft 40 with a tissue-penetrating distal tip 48, as illustrated in FIGS. 2A-2C, and a profiled stylet 56 as an obturator within the elongated shaft 40, as illustrated in FIGS. 8A-8C.

First, the pulmonary access device 14 is assembled by introducing the profiled stylet 56 within the channel 50 of the elongated shaft 40 (e.g., by introducing the profiled stylet 56 through the stylet port 71 associated with the handle body 70 (shown in FIGS. 10-13), and into the working channel 50 along the elongated shaft 40) until the distal stylet section 62 (obturator) is distal to the tissue-penetrating distal tip 48 of the elongated shaft 40, as illustrated in FIG. 8A (step 102).

Figure 21A:
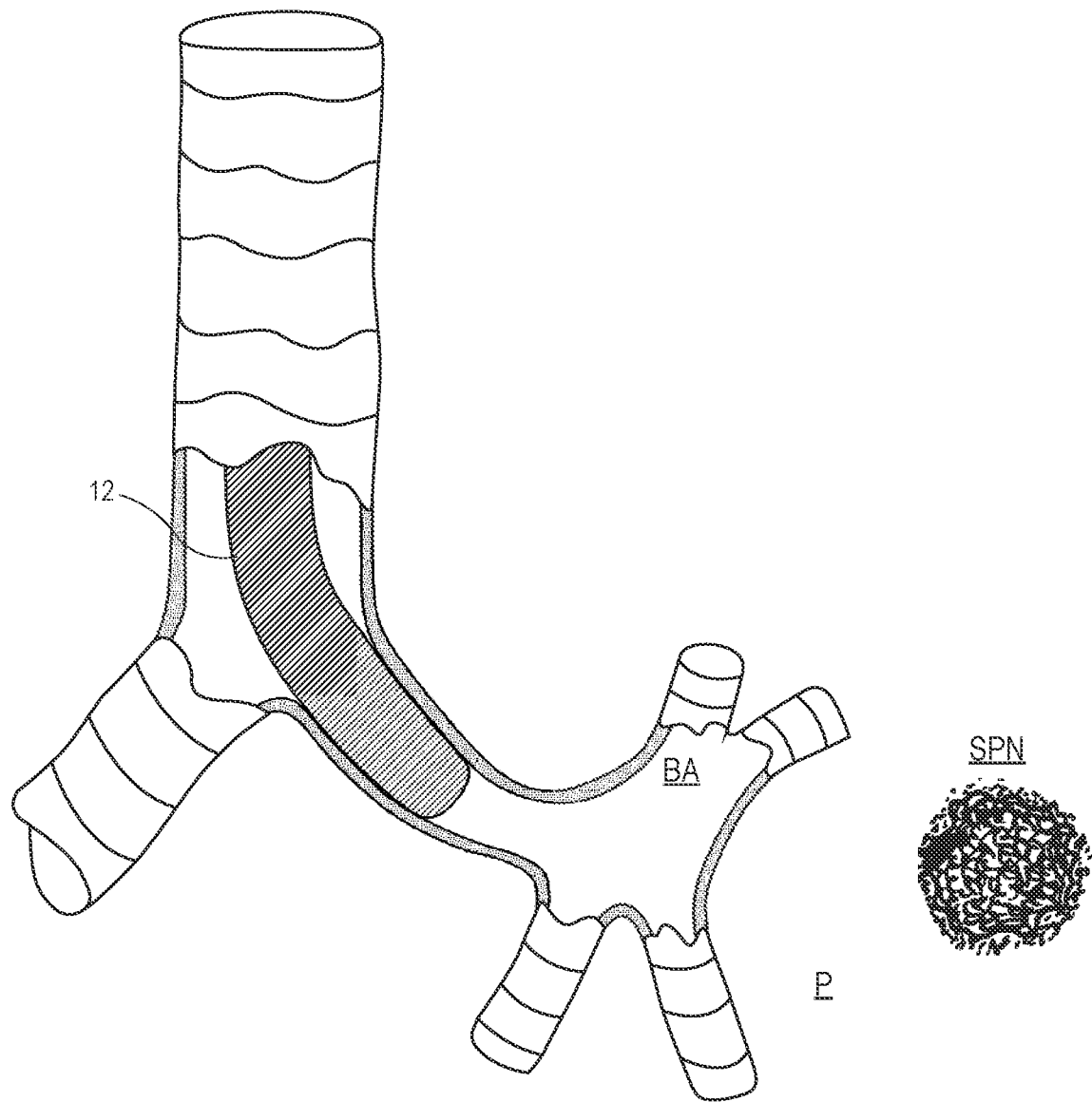
FIGS. 21A-21J are plan views illustrating the transbronchial pulmonary biopsy system of FIG. 1 in use to take biopsy samples from the SPN of the patient in accordance with the method of FIG. 20.
Figure 21B:
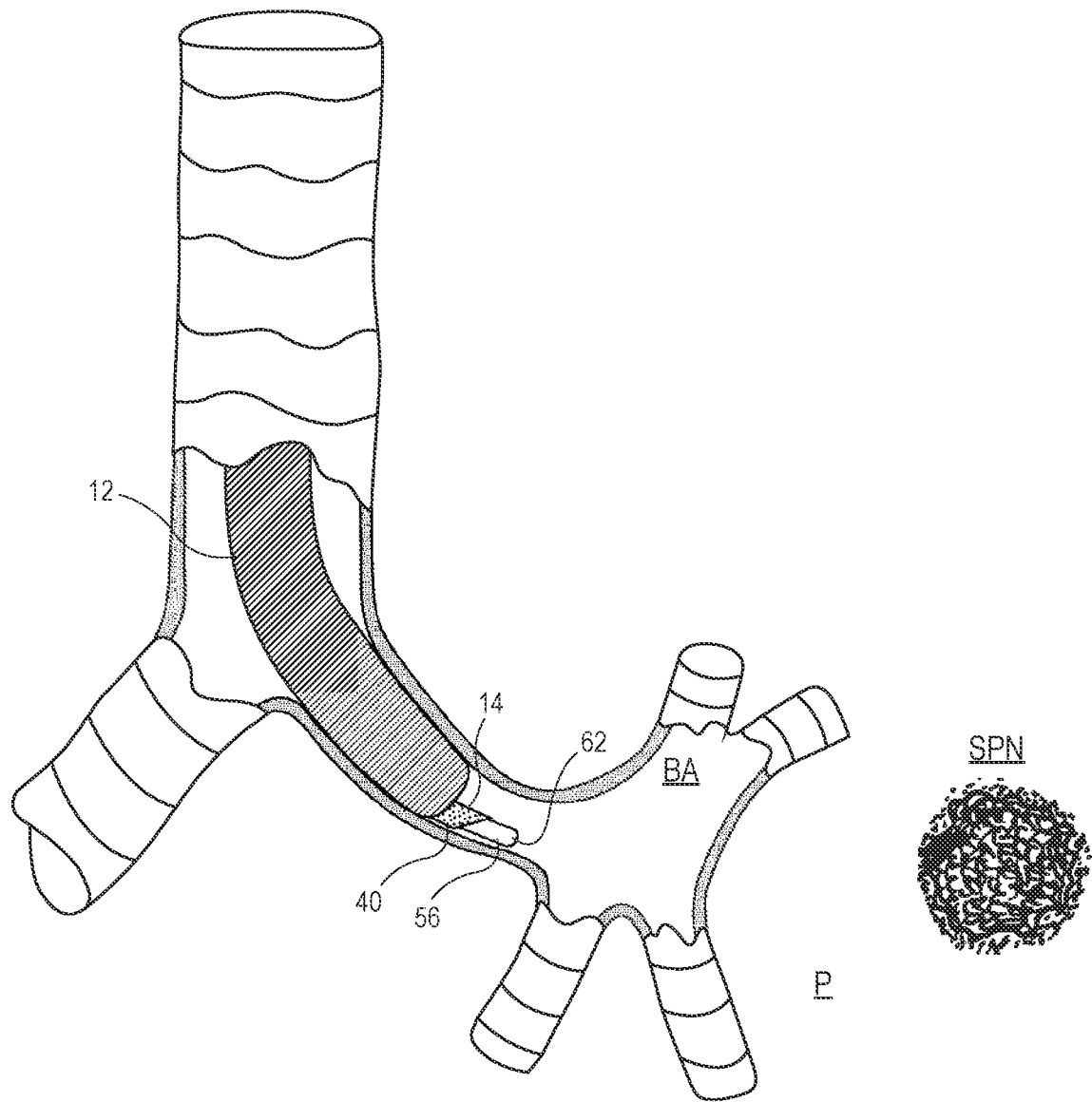

Next, the pulmonary access device 14 is navigated through a bronchial airway BA of the patient. In particular, the bronchoscope 12 is navigated through the bronchial airway BA of the patient in a conventional manner (step 104), as illustrated in FIG. 21A. The pulmonary access device 14 is then introduced through the working channel 22 of bronchoscope 12 (shown in FIG. 1) into the bronchial airway BA of the patient (step 106), as illustrated in FIG. 21B. In the case where the bronchoscope 12 is provided with a coupling 26, the pulmonary access device 14 may be locked within the working channel 22 of the bronchoscope 12 (shown in FIG. 1).

Figure 21C:
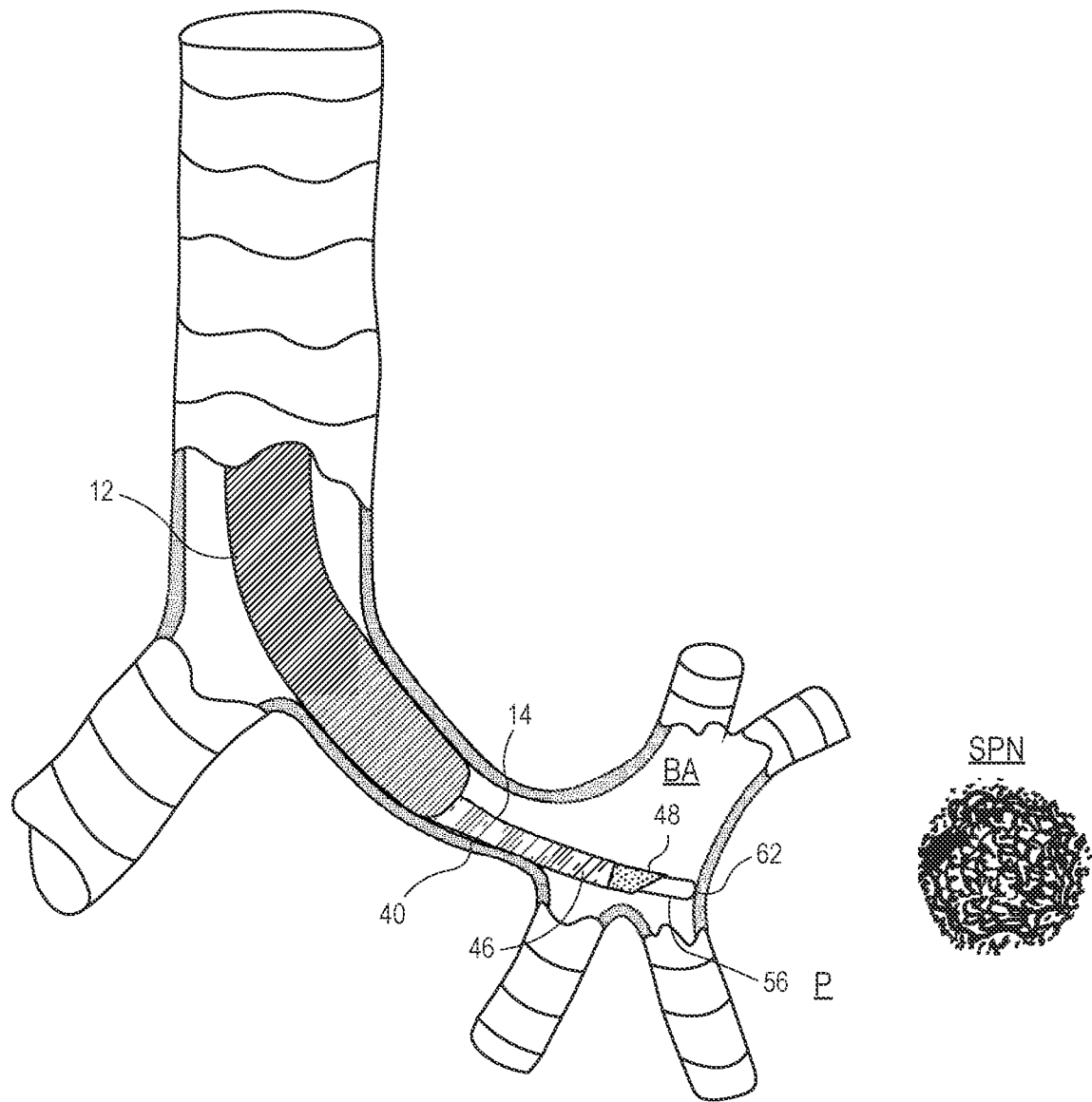

The pulmonary access device 14 is then navigated further into the bronchial airway BA of the patient by actively steering the distal shaft section 46 while distally advancing the pulmonary access device 14 within the bronchial airway BA of the patient until the tissue-penetrating distal tip 48 of the elongated shaft 40 is adjacent the access puncture point to the SPN (step 108), as illustrated in FIG. 21C. In the exemplary embodiment, the pulmonary access device 14 is actively steered by tensioning the pull wire 64 via manipulation of the deflection control actuator 72 illustrated in FIGS. 10-11 or via manipulation of the deflection control actuator 88 illustrated in FIGS. 12-14) to actively deflect the distal shaft section 46, and the pulmonary access device 14 is distally advanced within the bronchial airway BA of the patient via linear displacement of the shaft displacement actuator 74 illustrated in FIGS. 10-11 or via linear displacement of the handle body 70 illustrated in FIGS. 12-14).

Figure 21D:
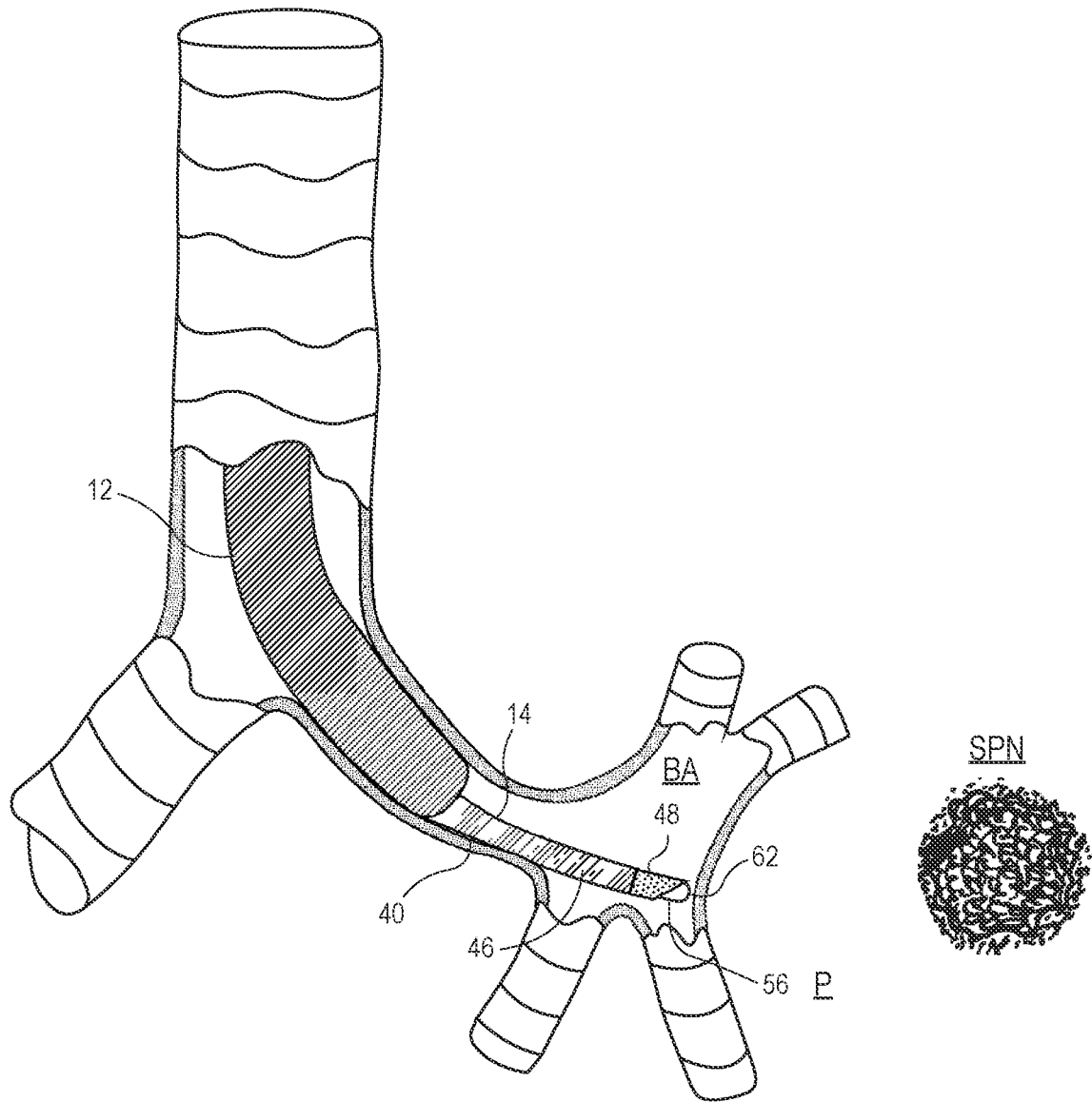
Figure 21E:
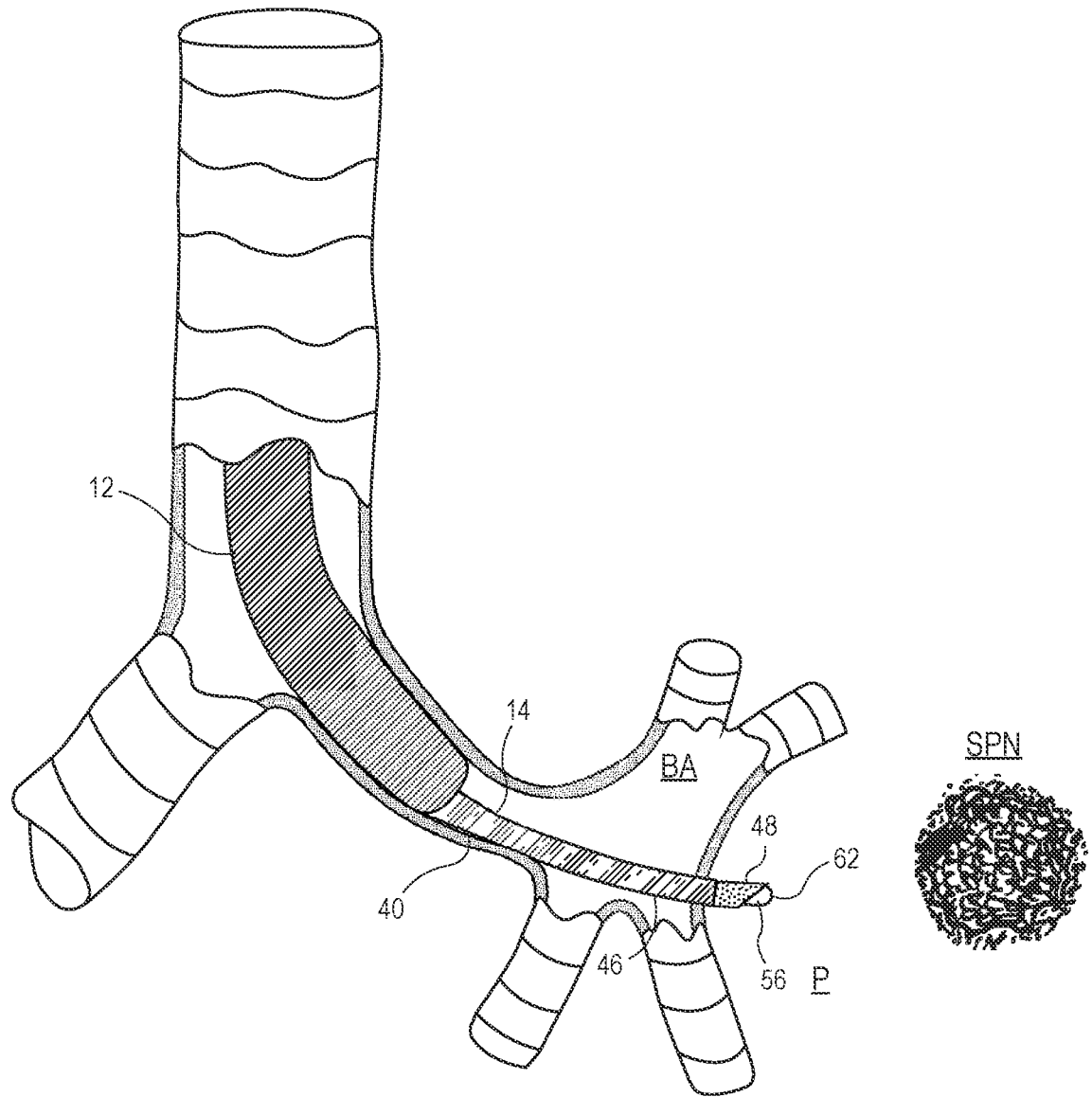

Next, the profiled stylet 56 is proximally retracted slightly within the channel 50 of the elongated shaft 40 until the distal stylet section 62 (obturator) is aligned with or proximal to the tissue-penetrating distal tip 48 of the elongated shaft 40, thereby exposing the tissue-penetrating distal tip 48 of the elongated shaft 40 (step 110), as illustrated in FIG. 8B and FIG. 21D. Then, if the tissue-penetrating distal tip 48 of the elongated shaft 40 is not already pointed towards the SPN, the distal shaft section 46 is actively deflected and rotated about the longitudinal axis 54 of elongated shaft 40, such that the tissue-penetrating distal tip 48 of the elongated shaft 40 points towards the SPN (step 112). In the exemplary embodiment, the distal shaft section 46 is actively deflected by tensioning the pull wire 64 (e.g., via manipulation of the deflection control actuator 72 illustrated in FIGS. 10-11 or the deflection control actuator 88 illustrated in FIGS. 12-14), and rotated via rotation of the shaft displacement actuator 74 illustrated in FIGS. 10-11 or via rotation of the handle body 70 illustrated in FIGS. 12-14). The tissue-penetrating distal tip 48 of the elongated shaft 40 is then punctured through the wall of the bronchial airway PA into the parenchyma P by distally advancing the pulmonary access device 14 (step 114), as illustrated in FIG. 21E. In the exemplary embodiment, the pulmonary access device 14 is distally advanced within the bronchial airway BA of the patient via linear displacement of the shaft displacement actuator 74 illustrated in FIGS. 10-11 or via linear displacement of the handle body 70 illustrated in FIGS. 12-14).

Figure 21F:
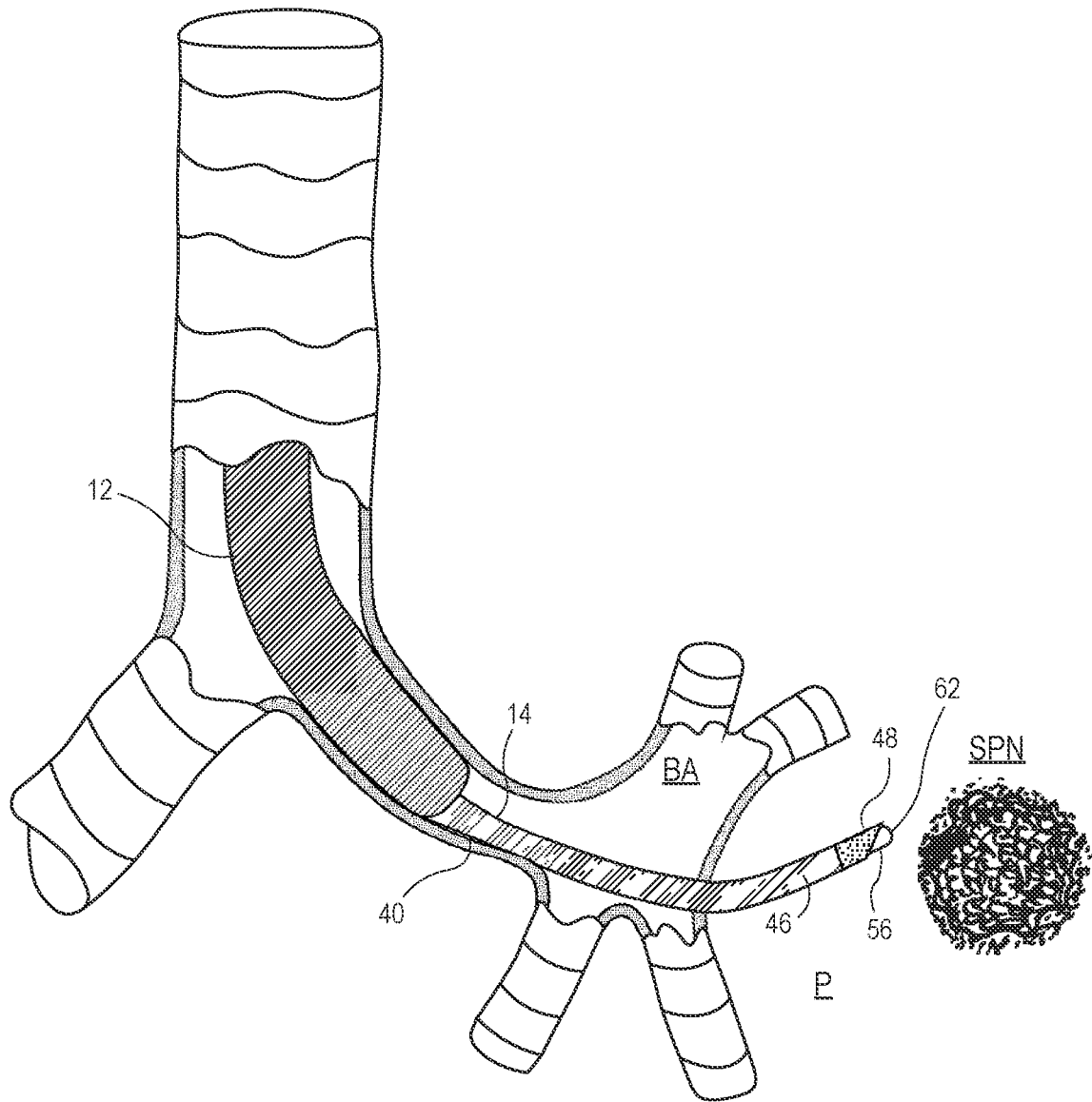
Figure 21G:
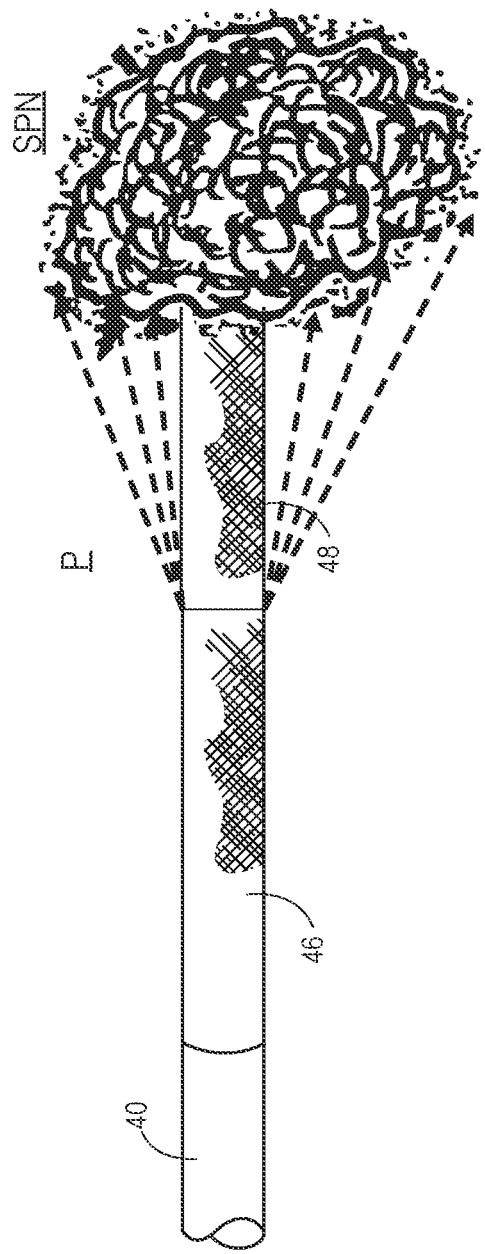

Next, the tissue-penetrating distal tip 48 of the elongated shaft 40 is tracked through the parenchyma P to a selected one of a plurality of different sites of the SPN by actively deflecting the distal shaft section 46 while distally advancing the pulmonary access device 14 (step 116), as illustrated in FIG. 21F. In the exemplary embodiment, the distal shaft section 46 is actively deflected by tensioning the pull wire 64 (e.g., via manipulation of the deflection control actuator 72 illustrated in FIGS. 10-11 or the deflection control actuator 88 illustrated in FIGS. 12-14). As illustrated in FIG. 21G, any one of a plurality of different sites of the SPN may be selected by controllably deflecting the distal shaft section 46. As such, multiple biopsies may be taken from various sites of the SPN, thereby maximizing the diagnostic yield of the biopsy.

Figure 21H:
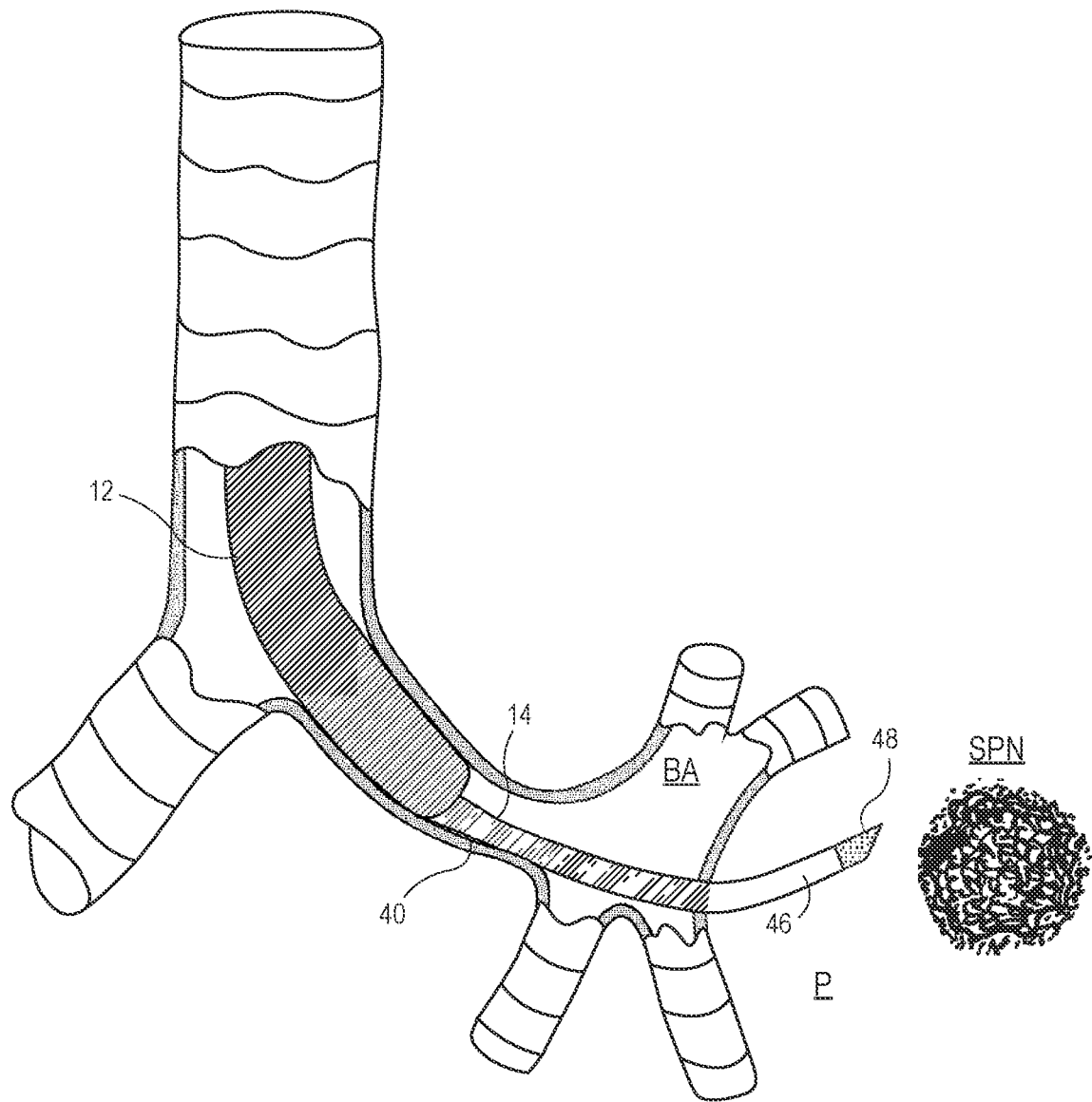
Figure 21I:
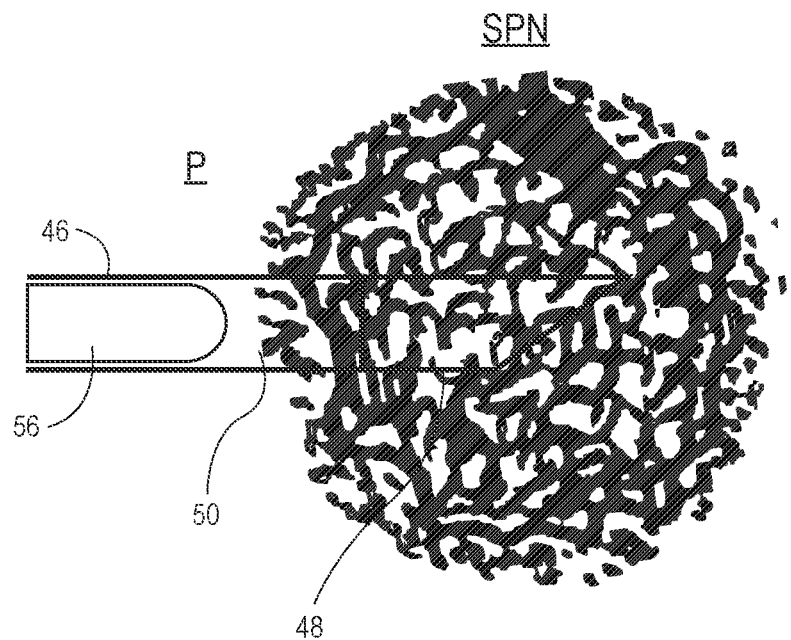

Then, the profiled stylet 56 is proximally retracted further within the channel 50 of the elongated shaft 40 until a sufficient sampling space is created in the distal end of the channel 50 of the elongated shaft 40 for coring a biopsy sample of the SPN (step 118), as illustrated in FIG. 8C and FIG. 21H. The biopsy sample at the selected site of the SPN is then cored with the tissue-penetrating distal tip 48 of elongated shaft 40 by distally advancing the pulmonary access device 14, such that the cored biopsy sample is disposed within the sampling space of the channel 50 (step 120), as illustrated in FIG. 21I. In the exemplary embodiment, the pulmonary access device 14 is distally advanced via linear displacement of the shaft displacement actuator 74 illustrated in FIGS. 10-11 or via linear displacement of the handle body 70 illustrated in FIGS. 12-14).

Figure 21J:
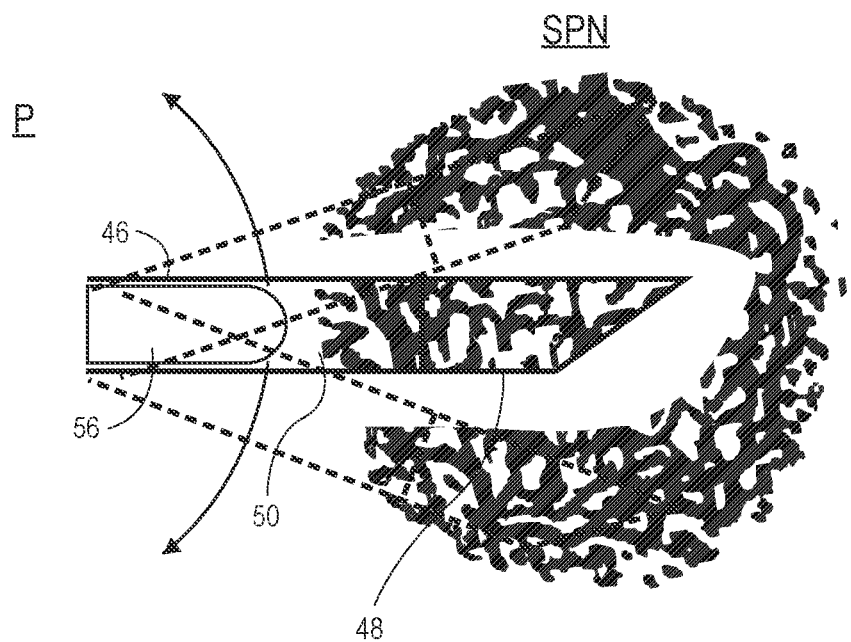

While the biopsy sample is cored within the channel 50 of the elongated shaft 40, the distal shaft section 46 is cyclically deflected until the cored biopsy sample is separated from the SPN (step 122), as illustrated in FIG. 21J. In the exemplary embodiment, the distal shaft section 46 is cyclically deflected by repeatedly tensioning and relaxing the pull wire 64 (e.g., via manipulation of the deflection control actuator 72 illustrated in FIGS. 10-11 or the deflection control actuator 88 illustrated in FIGS. 12-14).

The pulmonary access device 14 is then removed from the patient while leaving the bronchoscope 12 in place within the bronchial airway BA of the patient (step 124), and the profiled stylet 56 is distally advanced within the channel 50 to dislodge the cored biopsy sample (step 126). Steps 106-124 can then be repeated to take another biopsy sample from a different site of the SPN, except that, instead of puncturing through the wall of the bronchial airway BA of the patient into the parenchyma P in step 114, the pulmonary access device 14 is reintroduced through the previously made puncture in the wall of the bronchial airway BA into the parenchyma P. In an optional method after the SPN has been completely biopsied, the profiled stylet 56 may be completely removed from the channel 50, and an aspiration system (not shown) can be fluidly coupled to the channel 50, and operated to aspirate any remaining loose cells from the SPN through the working channel 50. The aspirate, along with the cells, may then be collected for analysis.

Figure 22:
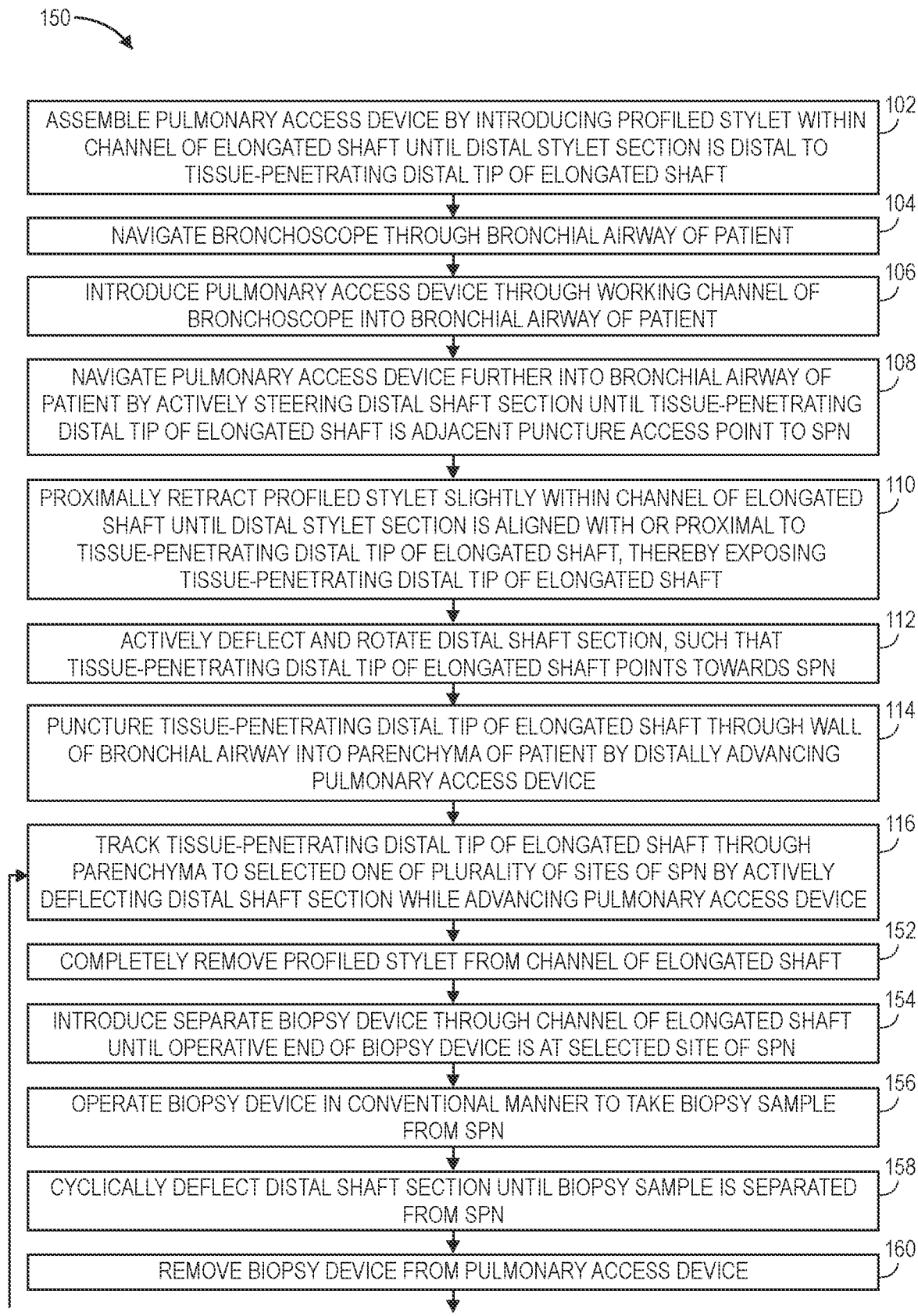
FIG. 22 is a flow diagram of another method of operating the transbronchial pulmonary biopsy system of FIG. 1 to take biopsy samples from a solitary pulmonary nodule (SPN) of a patient.
Figure 22:
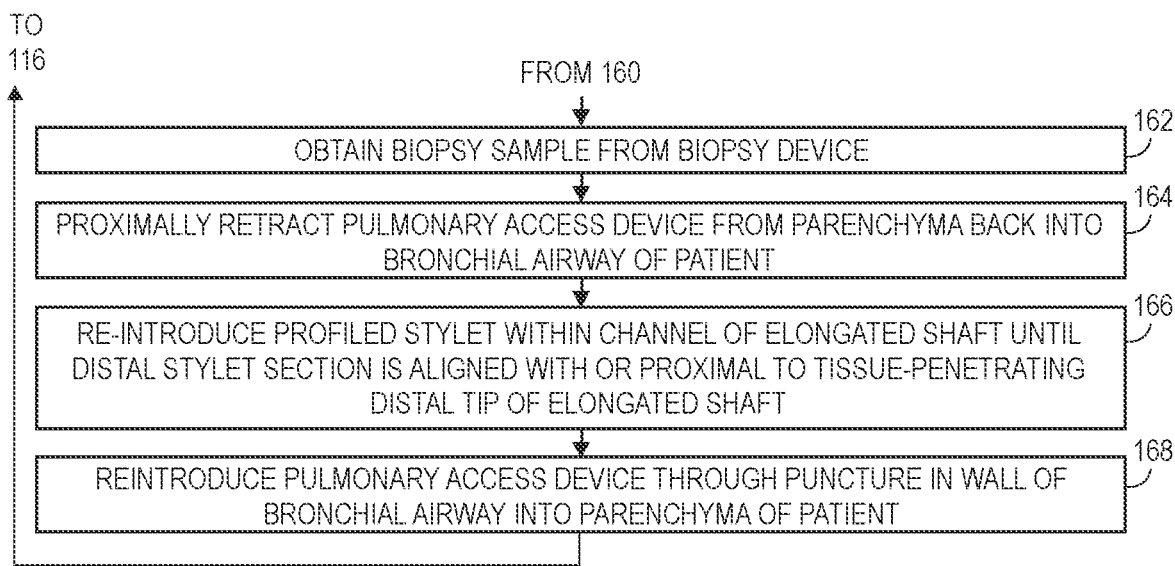
Figure 23:
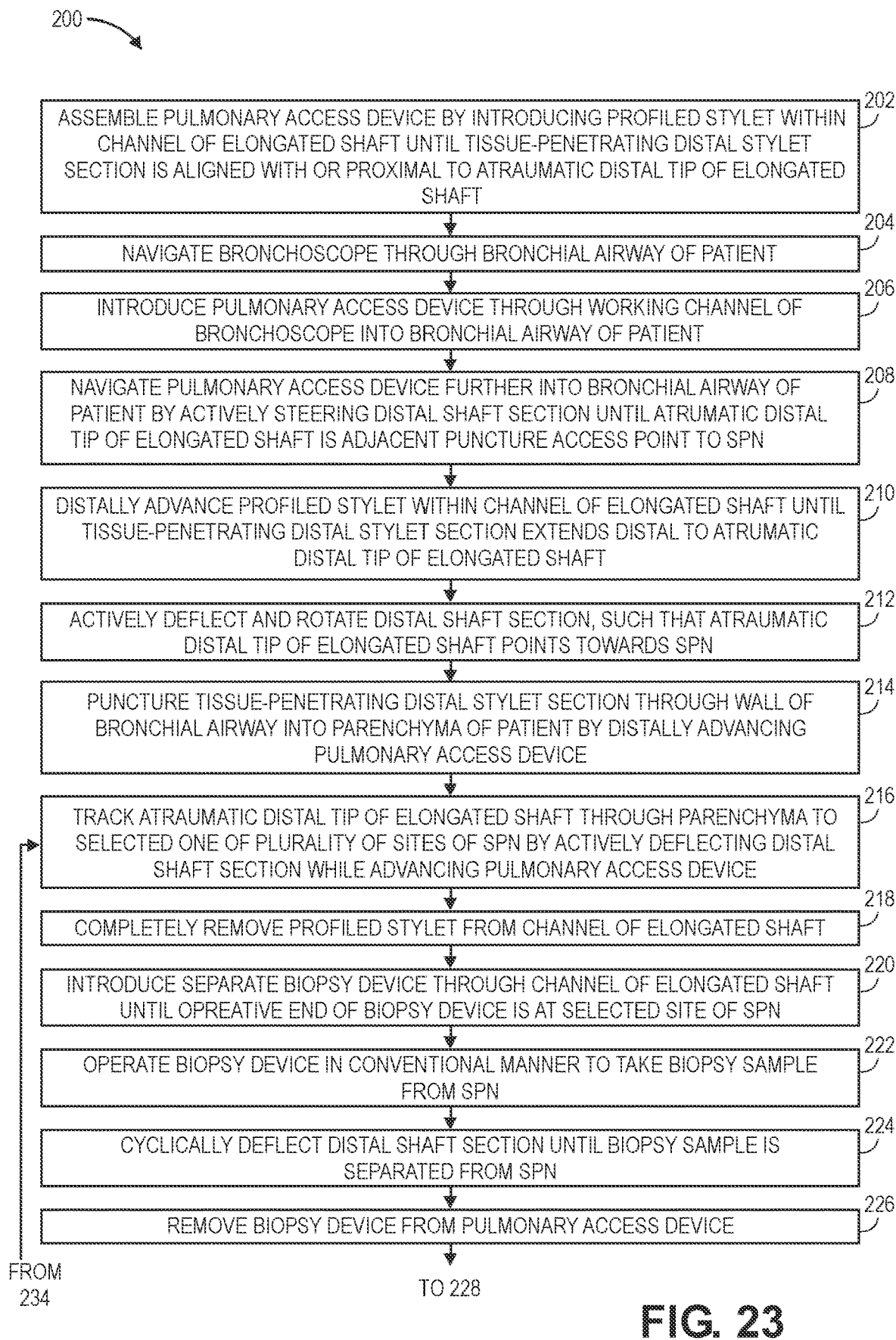
FIG. 23 is a flow diagram of still another method of operating the transbronchial pulmonary biopsy system of FIG. 1 to take biopsy samples from a solitary pulmonary nodule (SPN) of a patient.
Figure 23:
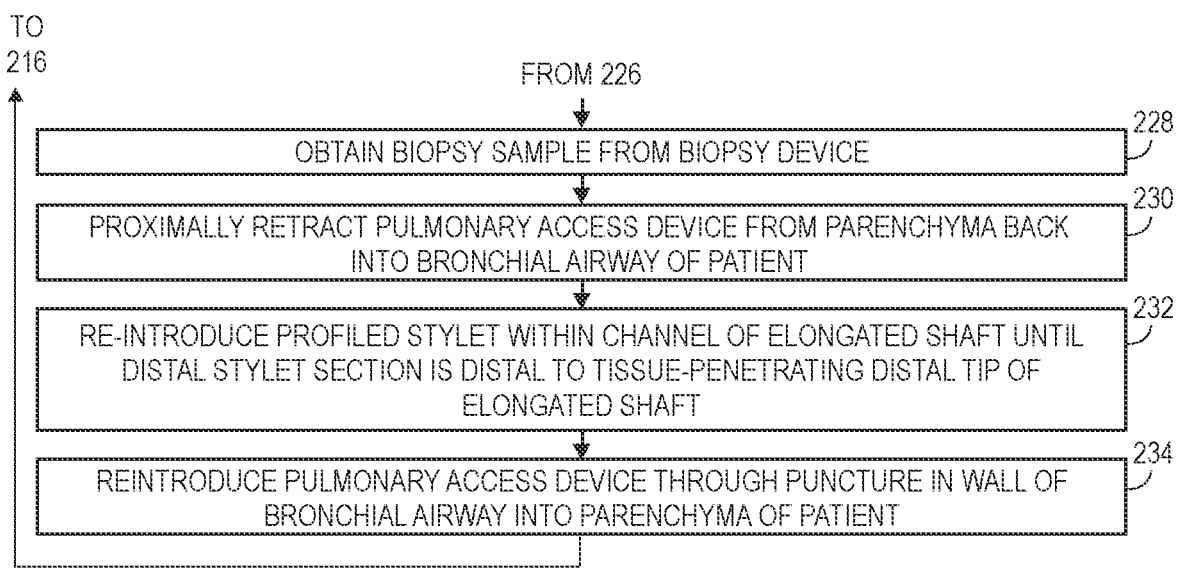

Referring to FIG. 22, another exemplary method 150 of using the transbronchial pulmonary biopsy system 10 to take biopsy samples from different sites of an SPN located in the parenchyma P of a patient will now be described. In this method, the pulmonary access device 14 serves as a channel device (as opposed to a biopsy needle) comprising the elongated shaft 40 with a tissue-penetrating distal tip 48, as illustrated in FIGS. 2A-2C, and a profiled stylet 56 having an obturating distal stylet section 62, as illustrated in FIGS. 8A-8C.

The method 150 is similar to the method 100 described above in that steps 102-116 are performed to track the tissue-penetrating distal tip 48 of the elongated shaft 40 through the parenchyma P to a selected one of a plurality of different sites of the SPN (step 116). The method 150 differs from the method 100 in that, instead of proximally retracting the profiled stylet 56 further within the channel 50 of the elongated shaft 40 to create sufficient sampling space in the distal end of the channel 50 of the elongated shaft 40 for coring a biopsy sample of the SPN, the profiled stylet 56 is completely removed from the channel 50 of the elongated shaft 40 (e.g., from the stylet port 71 associated with the handle body 70) (step 152), and a separate biopsy device (not shown) is introduced within the channel 50 of the elongated shaft 40 (e.g., by introducing the profiled stylet 56 through the stylet port 71 associated with the handle body 70 (shown in FIGS. 10-13) until the operative end of the biopsy device is at the selected site of the SPN (step 154).

The biopsy device is then operated in a conventional manner to take a biopsy sample from the SPN (step 156), and if required, the distal shaft section 46 may be cyclically deflected until the biopsy sample is separated from the SPN (step 158). The biopsy device is then completely removed from the channel 50 of the elongated shaft 40 (e.g., from the stylet port 71 associated with the handle body 70) (step 160), and the biopsy sample is obtained from the biopsy device (step 162). The pulmonary access device 14 is then proximally retracted from the parenchyma P back into the bronchial airway BA of the patient (step 164). In the exemplary embodiment, the pulmonary access device 14 is proximally retracted via linear displacement of the shaft displacement actuator 74 illustrated in FIGS. 10-11 or via linear displacement of the handle body 70 illustrated in FIGS. 12-14).

The profiled stylet 56 is re-introduced within the channel 50 of the elongated shaft 40 until the distal stylet section 62 (obturator) is aligned with or just proximal to the tissue-penetrating distal tip 48 of the elongated shaft 40 (step 166). The pulmonary access device 14 is then re-introduced through the puncture in the bronchial airway BA into the parenchyma P of the patient (step 168), and steps 116 and 152-162 repeated to take another biopsy sample from a different site of the SPN.

Referring to FIGS. 23 and 24A-24J, still another exemplary method 200 of using the transbronchial pulmonary biopsy system 10 to take biopsy samples from different sites of an SPN located in the parenchyma P of a patient will now be described. In this method, the pulmonary access device 14 serves as a channel device comprising the elongated shaft 40 with an atraumatic distal tip 48, as illustrated in FIG. 5, and a profiled stylet 56' having a tissue-penetrating distal stylet section 62', as illustrated in FIGS. 9A-9C.

First, the pulmonary access device 14 is assembled by introducing the profiled stylet 56' within the channel 50 of the elongated shaft 40 (e.g., by introducing the profiled stylet 56' through the stylet port 71 associated with the handle body 70 (shown in FIGS. 10-13), and into the working channel 50 along the elongated shaft 40) until the tissue-penetrating distal stylet section 62' is aligned with or proximal to the atraumatic distal tip 48' of the elongated shaft 40, as illustrated in FIG. 9A (step 202).

Figure 24A:
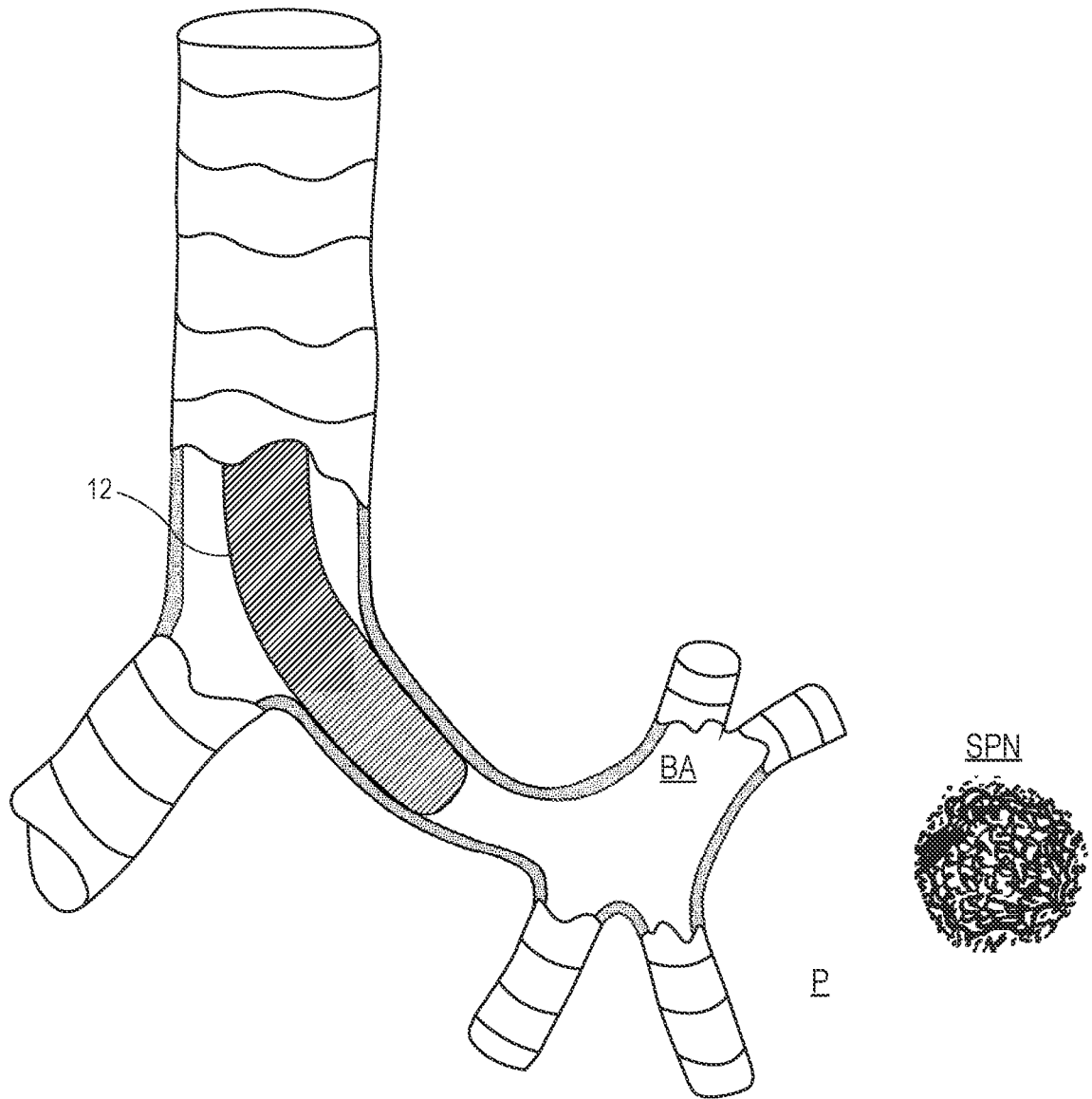
FIGS. 24A-24J are plan views illustrating the transbronchial pulmonary biopsy system FIG. 1 in use to take biopsy samples from the SPN of the patient in accordance with the method of FIG. 23
Figure 24B:
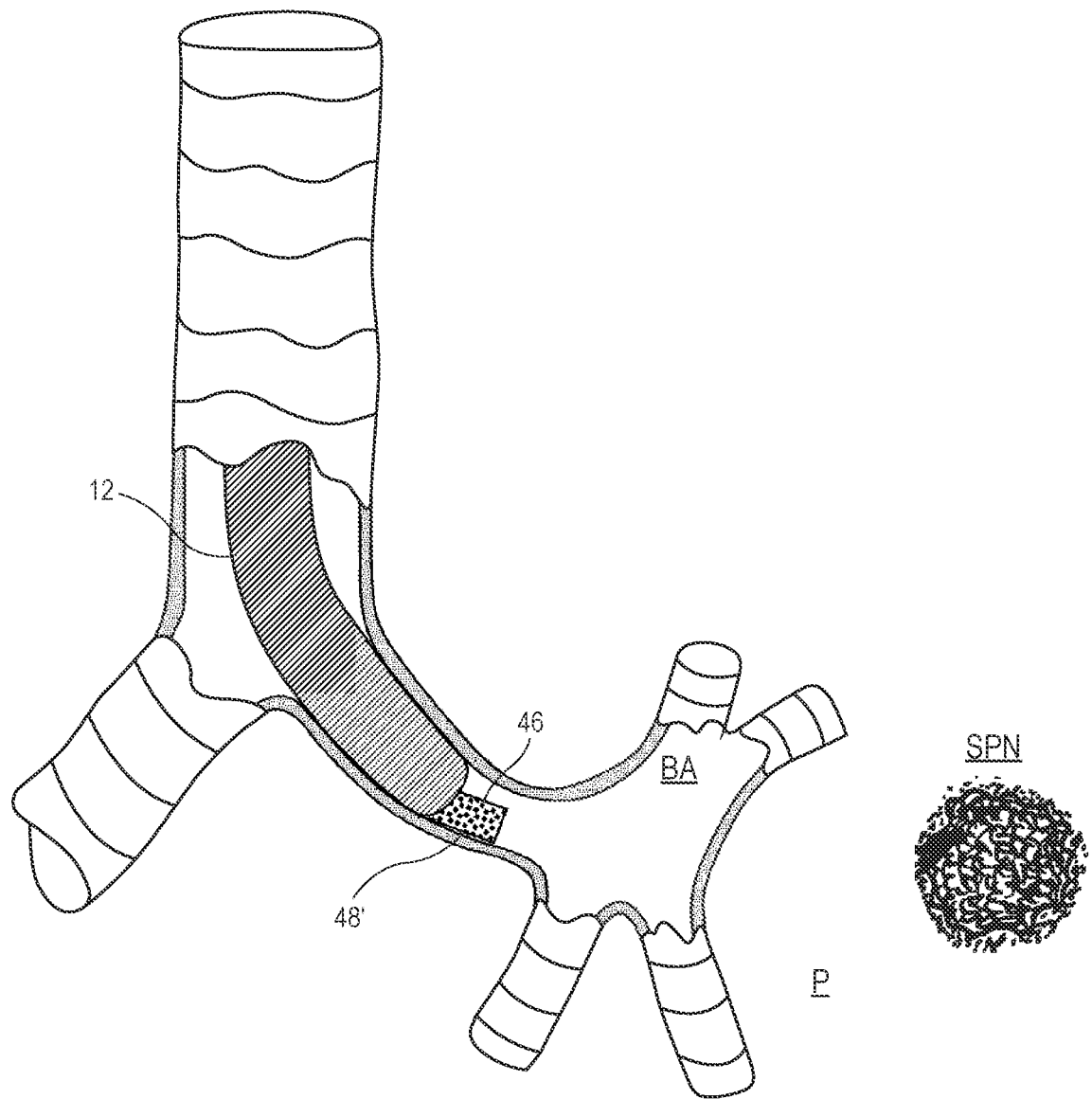

Next, the pulmonary access device 14 is navigated through a bronchial airway BA of the patient. In particular, the bronchoscope 12 is navigated through the bronchial airway BA of the patient in a conventional manner (step 204), as illustrated in FIG. 24A. The pulmonary access device 14 is then introduced through the working channel 22 of bronchoscope 12 (shown in FIG. 1) into the bronchial airway BA of the patient (e.g., via the access port 25 of the bronchoscope 12) (step 206), as illustrated in FIG. 24B. In the case where the bronchoscope 12 is provided with a coupling 26, the pulmonary access device 14 may be locked within the working channel 22 of the bronchoscope 12 (shown in FIG. 1).

Figure 24C:
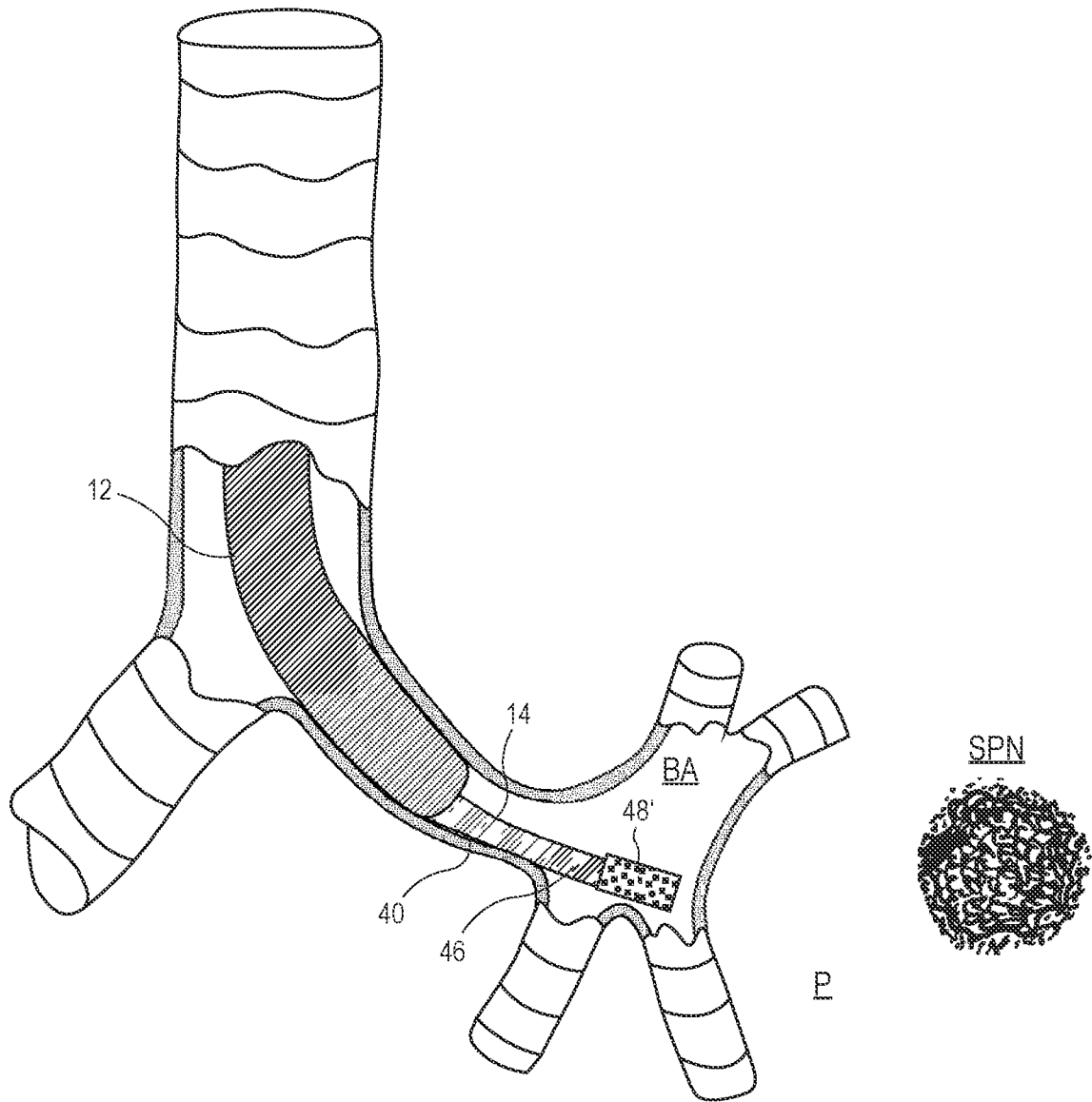

The pulmonary access device 14 is then navigated further into the bronchial airway BA of the patient by actively steering the distal shaft section 46 while distally advancing the pulmonary access device 14 within the bronchial airway BA of the patient until the atraumatic distal tip 48' of the elongated shaft 40 is adjacent the access puncture point to the SPN (step 208), as illustrated in FIG. 24C. In the exemplary embodiment, the pulmonary access device 14 is actively steered by tensioning the pull wire 64 via manipulation of the deflection control actuator 72 illustrated in FIGS. 10-11 or via manipulation of the deflection control actuator 88 illustrated in FIGS. 12-14) to actively deflect the distal shaft section 46, and the pulmonary access device 14 is distally advanced within the bronchial airway BA of the patient via linear displacement of the shaft displacement actuator 74 illustrated in FIGS. 10-11 or via linear displacement of the handle body 70 illustrated in FIGS. 12-14).

Figure 24D:
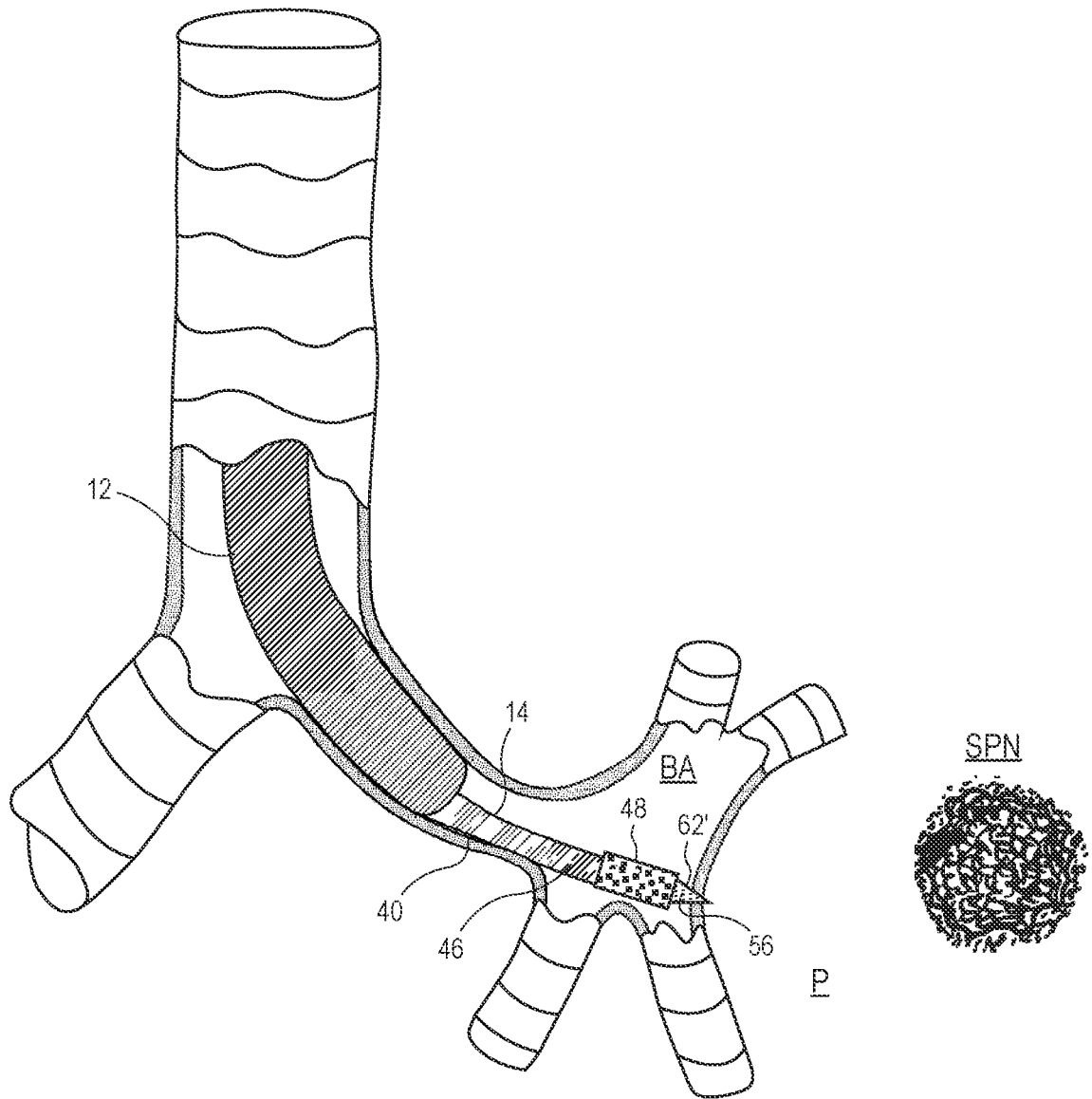
Figure 24E:
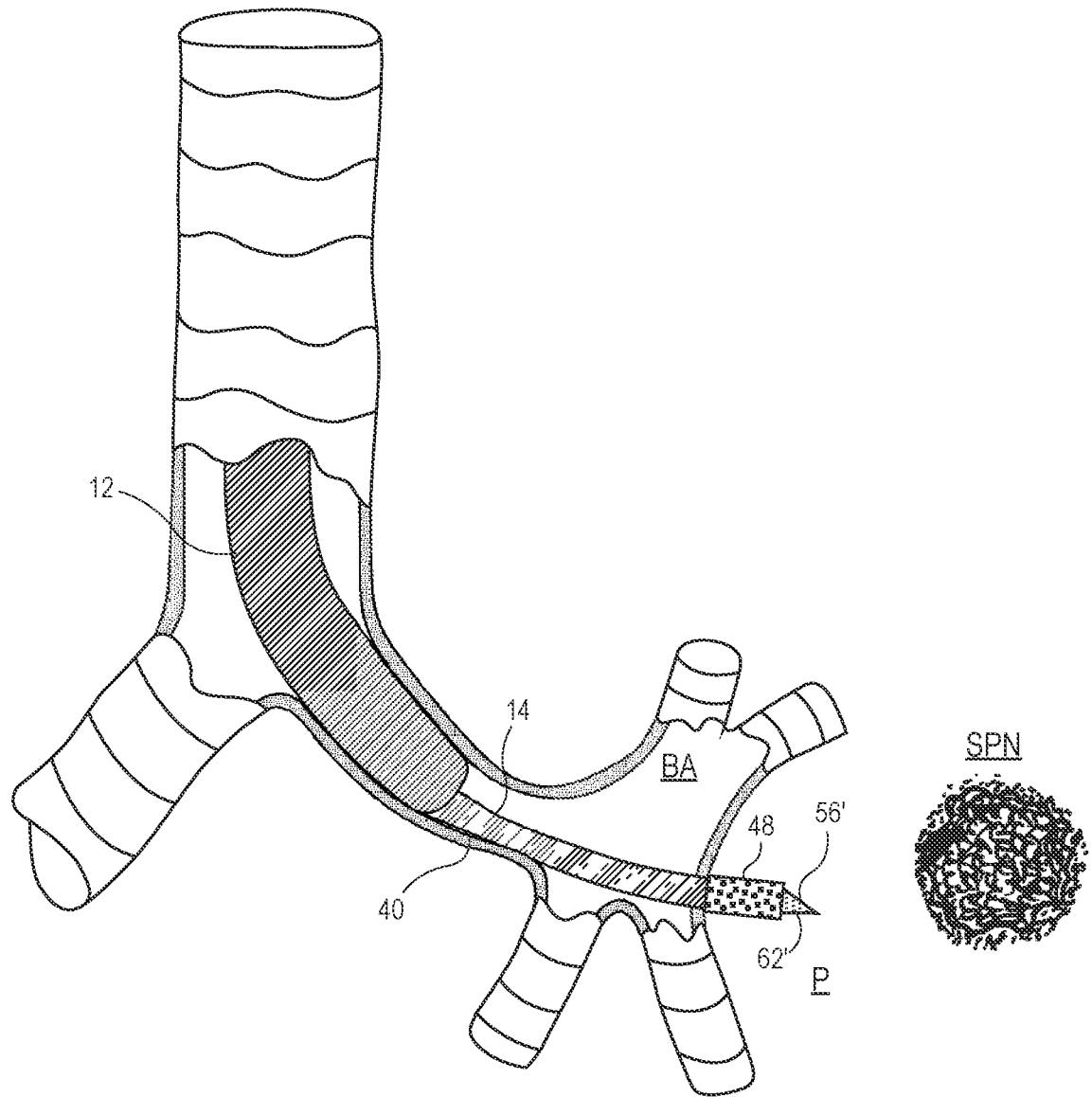

Next, the profiled stylet 56 is distally advanced within the channel 50 of the elongated shaft 40 until the tissue-penetrating distal stylet section 62' extends distally from the atraumatic distal tip 48' of the elongated shaft 40 (step 210), as illustrated in FIG. 9B and FIG. 24D. Then, if the atraumatic distal tip 48' of the elongated shaft 40 is not already pointed towards the SPN, the distal shaft section 46 is actively deflected and rotated about the longitudinal axis 54 of elongated shaft 40, such that the atraumatic distal tip 48' of the elongated shaft 40 points towards the SPN (step 212). In the exemplary embodiment, the distal shaft section 46 is actively deflected by tensioning the pull wire 64 (e.g., via manipulation of the deflection control actuator 72 illustrated in FIGS. 10-11 or the deflection control actuator 88 illustrated in FIGS. 12-14), and rotated via rotation of the shaft displacement actuator 74 illustrated in FIGS. 10-11 or via rotation of the handle body 70 illustrated in FIGS. 12-14). The tissue-penetrating distal stylet section 62' is then punctured through the wall of the bronchial airway PA into the parenchyma P by distally advancing the pulmonary access device 14 (step 214), as illustrated in FIG. 24E. In the exemplary embodiment, the pulmonary access device 14 is distally advanced within the bronchial airway BA of the patient via linear displacement of the shaft displacement actuator 74 illustrated in FIGS. 10-11 or via linear displacement of the handle body 70 illustrated in FIGS. 12-14).

Figure 24F:
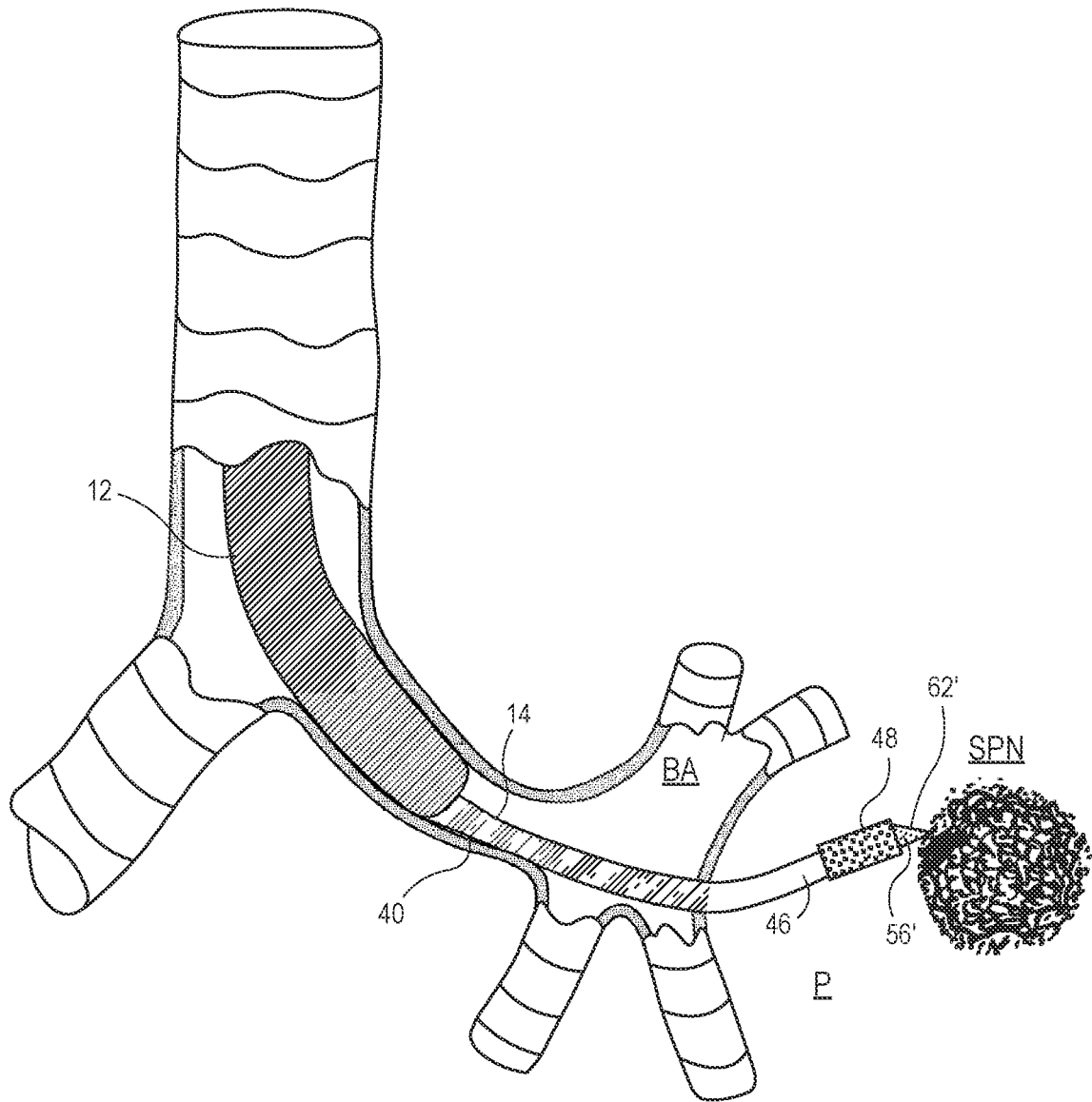
Figure 24G:
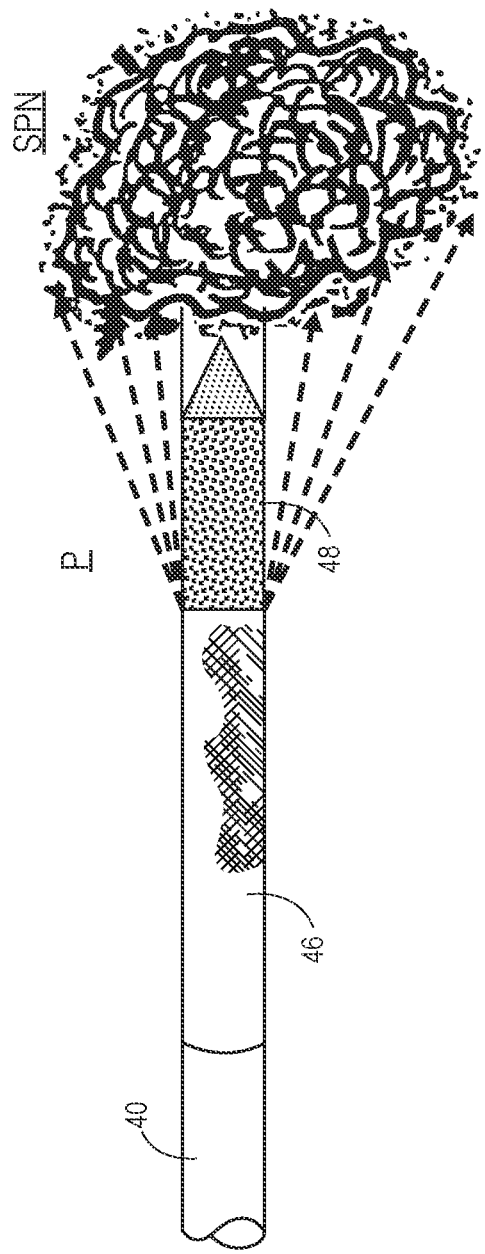

Next, the atraumatic distal tip 48' of the elongated shaft 40 is tracked through the parenchyma P to a selected one of a plurality of different sites of the SPN by actively deflecting the distal shaft section 46 while distally advancing the pulmonary access device 14 (step 216), as illustrated in FIG. 24F. In the exemplary embodiment, the distal shaft section 46 is actively deflected by tensioning the pull wire 64 (e.g., via manipulation of the deflection control actuator 72 illustrated in FIGS. 10-11 or the deflection control actuator 88 illustrated in FIGS. 12-14). As illustrated in FIG. 24G, any one of a plurality of different sites of the SPN may be selected by controllably deflecting the distal shaft section 46. As such, multiple biopsies may be taken from various sites of the SPN, thereby maximizing the diagnostic yield of the biopsy.

Figure 24H:
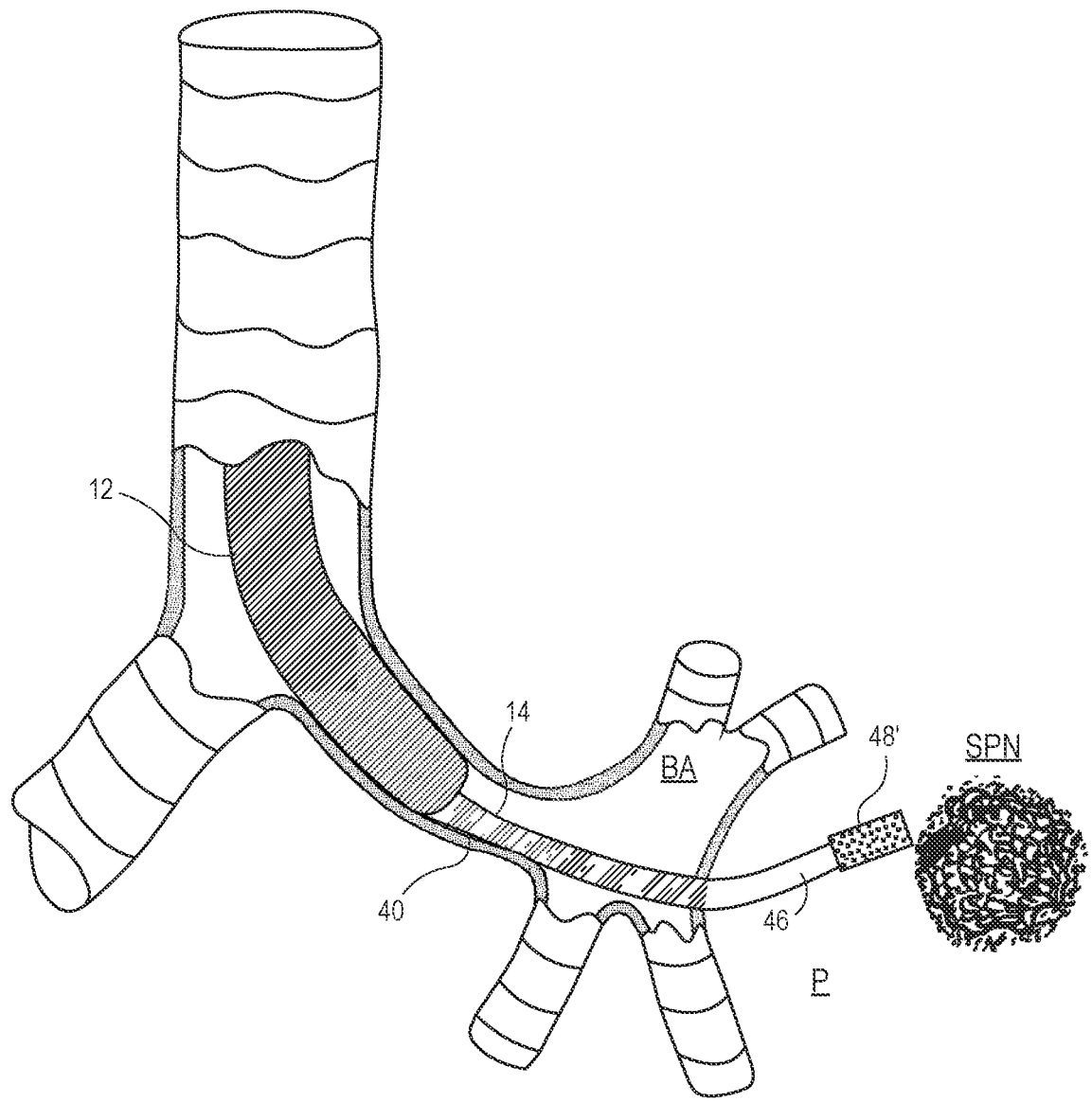

Next, the profiled stylet 56' is completely removed from the channel 50 of the elongated shaft 40 (e.g., from the stylet port 71 associated with the handle body 70) (step 218), and a separate biopsy device 90 (e.g., biopsy forceps) is introduced within the channel 50 of the elongated shaft 40 (e.g., by introducing the biopsy device 90 through the stylet port 71 associated with the handle body 70 (shown in FIGS. 10-13) until the operative end of the biopsy device 90 is at the selected site of the SPN (step 220), as illustrated in FIG. 24H.

Figure 24I:
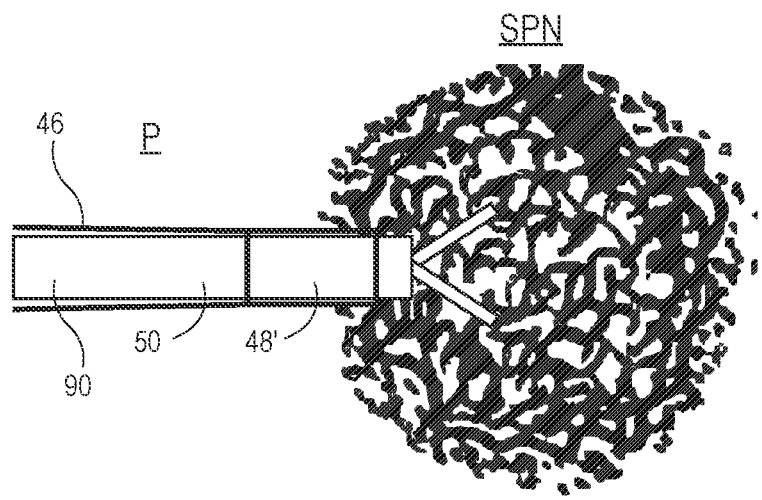
Figure 24J:
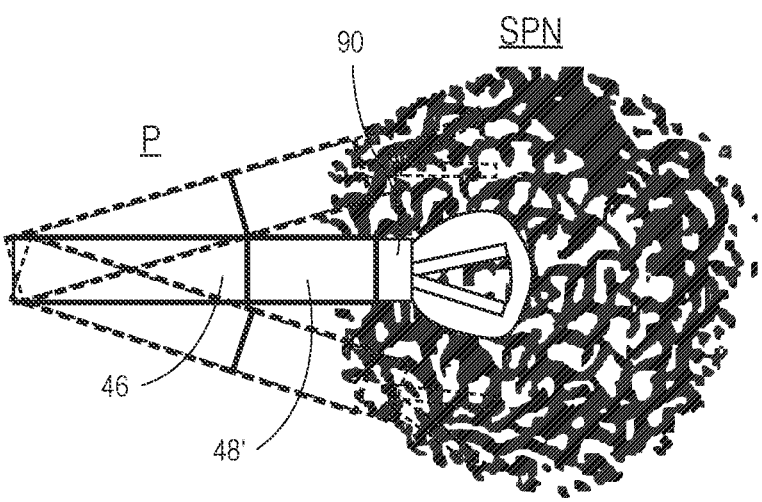

The biopsy device 90 is then operated in a conventional manner to take a biopsy sample from the SPN (step 222), as illustrated in FIG. 24I, and if required, the distal shaft section 46 may be cyclically deflected until the biopsy sample is separated from the SPN (step 224), as illustrated in FIG. 24J. The biopsy device 90 is then completely removed from the channel 50 of the elongated shaft 40 (e.g., from the stylet port 71 associated with the handle body 70) (step 226), and the biopsy sample is obtained from the biopsy device 90 (step 228). The pulmonary access device 14 is then proximally retracted from the parenchyma P back into the bronchial airway BA of the patient (step 230). In the exemplary embodiment, the pulmonary access device 14 is proximally retracted via linear displacement of the shaft displacement actuator 74 illustrated in FIGS. 10-11 or via linear displacement of the handle body 70 illustrated in FIGS. 12-14).

The profiled stylet 56' is re-introduced within the channel 50 of the elongated shaft 40 until the distal stylet section 62 is distal to the tissue-penetrating distal tip 48 of the elongated shaft 40 (step 232). The pulmonary access device 14 is then re-introduced through the puncture in the bronchial airway BA into the parenchyma P of the patient (step 234), and steps 216-228 are repeated to take another biopsy sample from a different site of the SPN.

Figure 25:
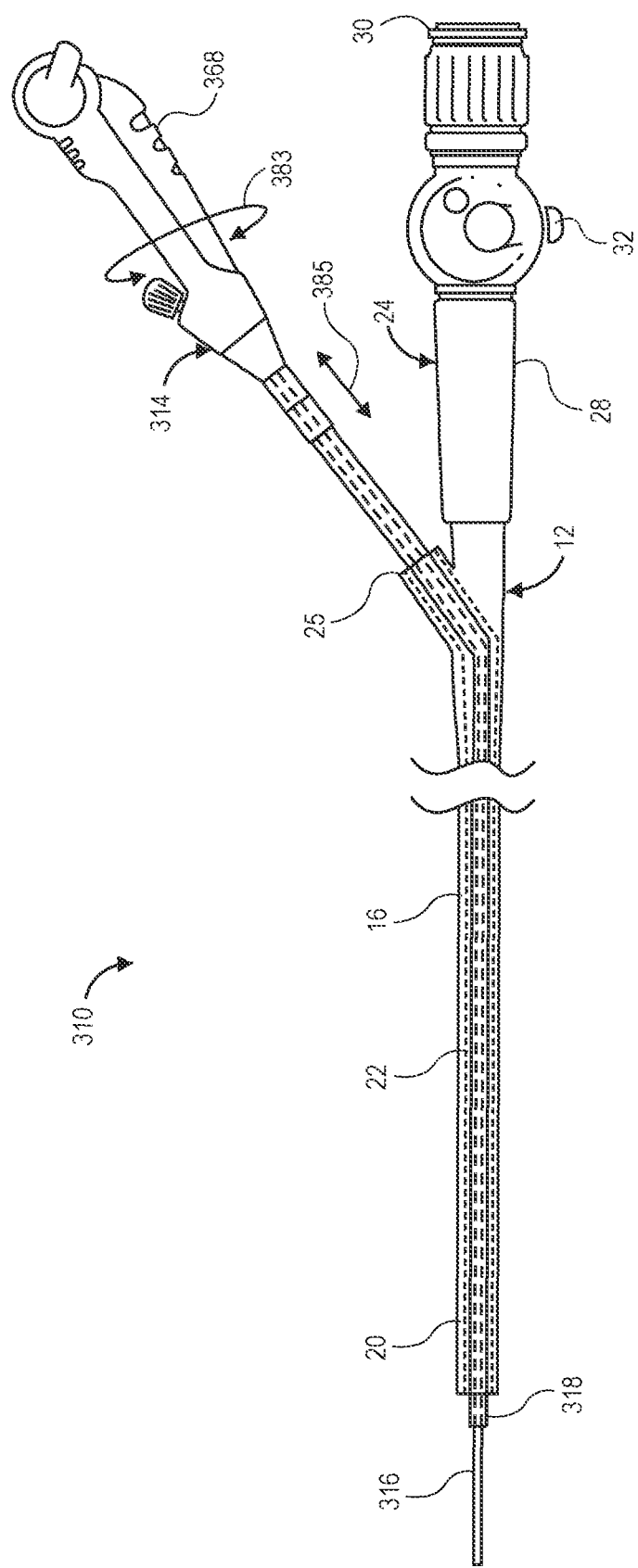
FIG. 25 is a plan view of a transbronchial pulmonary biopsy system constructed in accordance with another embodiment of the present inventions.

Referring to FIG. 25, another exemplary embodiment of a transbronchial pulmonary biopsy system 310 capable of accessing an identified SPN in the parenchyma of a lung located remotely from a bronchial airway in the lung will be described. The transbronchial pulmonary biopsy system 310 generally comprises the flexible bronchoscope 12 described above and a pulmonary access device 314. The pulmonary access device 314 generally comprises a steerable needle 316 and an access sheath 318 in which the steerable needle 316 is slidably disposed. As will be described in further detail below, when delivered to the SPN, the steerable needle 316 can be removed from the access sheath 318, thereby allowing one or more separate biopsy tools to be introduced through the access sheath 318 for taking biopsy samples from the SPN.

In the illustrated embodiment, the steerable needle 316 takes the form of the pulmonary access device 14 illustrated in FIGS. 2A-2C, which may serve as either a biopsy needle or a channel device. In this case, both the steerable needle 316 and the access sheath 318 may provide biopsy functionality (i.e., the physician may operate the steerable needle 316 to take biopsy samples from the SPN (as described above with respect to the method 150 of FIG. 22 or the method 200 of FIG. 23) and/or remove the steerable needle 316 from the access sheath 318 and introduce separate biopsy tool(s) though the access sheath 318 to take biopsy samples from the SPN). In alternative embodiments, the steerable needle 316 may merely take the form of any needle that can be actively steered, e.g., via the use of one or more pull wires, but has no biopsy functionality, in which case, the access sheath 318, after the steerable needle 316 has been removed, provides the sole means for taking biopsy samples from the SPN via separate biopsy tools introduced through the access sheath 318.

As illustrated in FIGS. 26A-26E and 27, the steerable needle 316 comprises an elongated shaft 340 having a proximal shaft section 342, a bendable shaft section 344, a distal shaft section 346, a distal tip 348, and a working channel 350 (either a biopsy channel or a working channel) (shown in FIGS. 26D and 26E) extending through the proximal shaft section 342, bendable shaft section 344, and distal shaft section 346, and terminating at a distal opening 352 in the distal tip 348. The construction of the proximal shaft section 342, bendable shaft section 344, distal shaft section 346, and distal tip 348 may be the same as that of the proximal shaft section 42, bendable shaft section 44, distal shaft section 46, and distal tip 48 of the pulmonary access device 14 illustrated in FIGS. 2A-2C.

Thus, the lateral stiffness profile of the distal shaft section 346 may be less than the lateral stiffness profile of the proximal shaft section 342, while the bendable shaft section 344 may have a transitioning lateral stiffness profile that transitions the higher lateral stiffness profile of the proximal shaft section 342 to the lower lateral stiffness profile of the distal shaft section 346 in the same manner as that of the distal shaft section 46, proximal shaft section 42, and bendable shaft section 44 illustrated in FIGS. 3A and 3B. The lateral stiffness profiles of the proximal shaft section 342 and the distal shaft section 346 may be uniform, although in alternative embodiments, either or both of the lateral stiffness profiles of the proximal shaft section 342 and the distal shaft section 346 may be non-uniform. The transitioning lateral stiffness profile of the bendable shaft section 344 may either be gradual, similar to the bendable shaft section 44 illustrated in FIG. 3A, such that it transitions the higher lateral stiffness profile of the proximal shaft section 342 to the lower lateral stiffness profile of the distal shaft section 346 in a gradual fashion, or uniform, similar to the bendable shaft section 44 illustrated in FIG. 3B, such that it transitions the higher lateral stiffness profile of the proximal shaft section 342 to the lower lateral stiffness profile of the distal shaft section 346 in a gradual fashion in a step-wise fashion. In an alternative embodiment, the bendable shaft section 344 does not transition the higher lateral stiffness profile of the proximal shaft section 342 to the lower lateral stiffness profile of the distal shaft section 346. Instead, the bendable shaft section 344 has the same lateral stiffness profile as that of the distal shaft section 346, and thus, the higher lateral stiffness profile of the proximal shaft section 342 is immediately transitioned to the lower lateral stiffness profiles of the bendable shaft section 344 and the distal shaft section 346 in a step-wise fashion in the same manner as the bendable shaft section 44 and distal shaft section 46 illustrated in FIG. 3C.

In this exemplary embodiment, the distal tip 348 takes the form of a tissue-penetrating distal tip that tapers to a point that is coincident with a longitudinal axis 354 of the elongated shaft 340 similar to the distal tip 48 illustrated in FIGS. 4A and 4B. In an alternative embodiment, the elongated shaft 340 has an atraumatic distal tip similar to the atraumatic tip 48', as illustrated in FIG. 5.

Figure 26A:
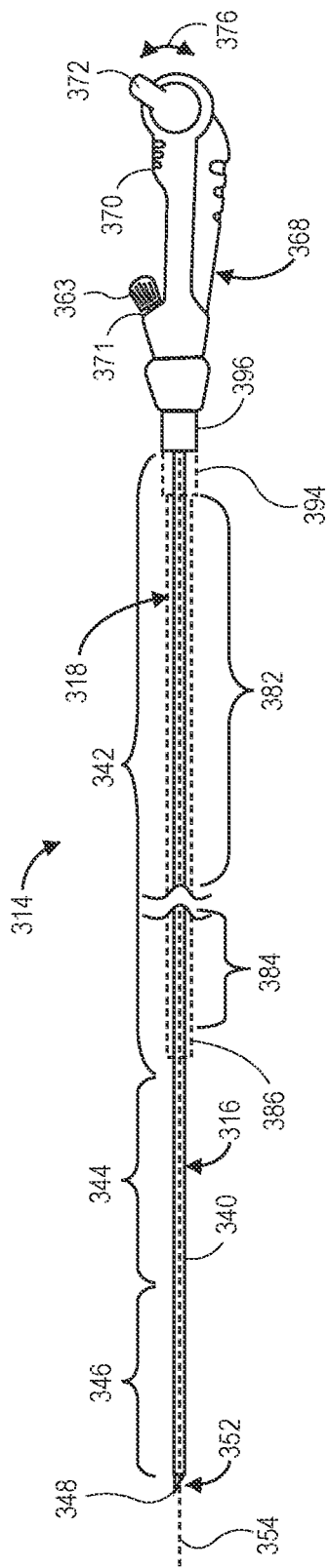
FIG. 26A is a plan view of a pulmonary access device used in the transbronchial pulmonary biopsy system of FIG. 25, particularly showing an access sheath of the pulmonary access device in a proximally retracted position.
Figure 26B:
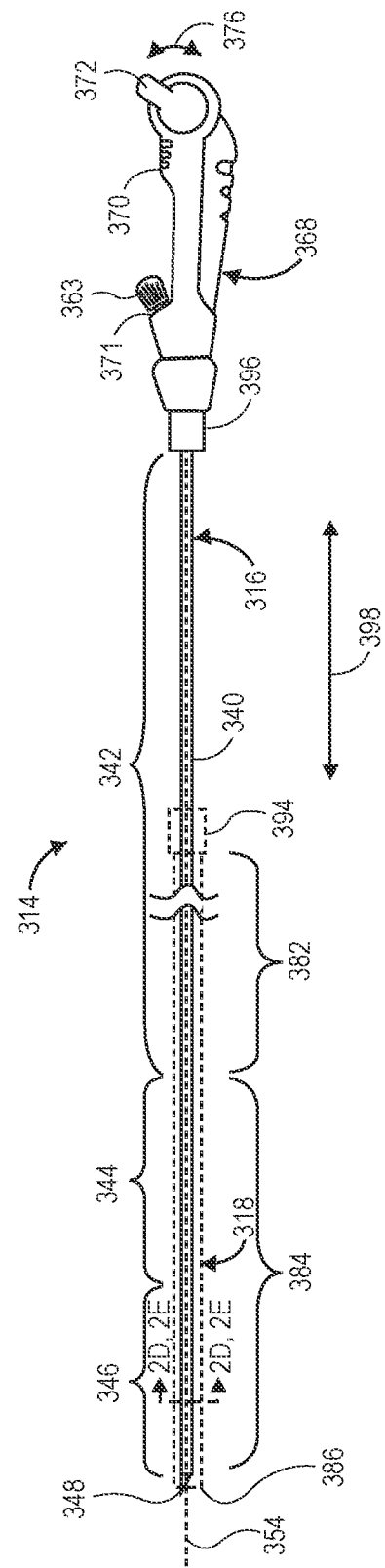
FIG. 26B is a plan view of the pulmonary access device of FIG. 26A, particularly showing the access sheath of the pulmonary access device in a distally advanced position.

The steerable needle 316 further comprises a profiled stylet 356 (shown in FIGS. 26D and 26E) configured for being disposed in the working channel 350 of the elongated shaft 340. The construction of the profiled stylet 356 may be same as the profiled stylet 56 illustrated in FIGS. 6 and 7, and thus, may have a proximal stylet section, intermediate stylet section, and distal stylet section (all not shown) that respectively align with the proximal shaft section 342, bendable shaft section 344, and distal shaft section 346 in the same manner as the proximal stylet section 58, intermediate stylet section 60, and distal stylet section 62 of the profiled stylet 56 aligns with the proximal shaft section 42, bendable shaft section 44, and distal shaft section 46 illustrated in FIG. 7. As illustrated in FIGS. 26A-26C, the profiled stylet 356 further comprises a stylet hub 363 affixed to the end of the proximal stylet section (not shown). The stylet 356 may, e.g., have any of the cross-sections of the stylets 56a-56c respectively illustrated in FIGS. 6A-6C.

In the same manner as illustrated in FIGS. 8A-8C, the distal tip of the profiled stylet 356 may either be atraumatic, when combined with an elongated shaft 340 with a tissue-penetrating distal tip, or in the same manner as illustrated in FIGS. 9A-9C, the distal tip of the profiled stylet 356 may be tissue-penetrating, when combined with an elongated shaft 340 with an atraumatic distal tip.

In the case where the steerable needle 316 serves as a biopsy needle, the profiled stylet 356 may be pulled back within the working channel 350 (or alternatively, the elongated shaft 340 may be distally advanced relative to the profiled stylet 356), such that the distal tip 348 may core a biopsy sample from the SPN, which biopsy sample may be retained in the distal end of the working channel 350. The profiled stylet 356 may then be pushed back to dislodge the biopsy sample from the working channel 350, which can be subsequently analyzed.

In the case where the steerable needle 316 serves as a channel device, the profiled stylet 356 may be completely removed from the working channel 350, such that a separate biopsy tool may be introduced through the working channel 350 to take biopsy samples from the SPN.

In the alternative case where the steerable needle 316 does not have biopsy functionality, the use of a stylet 356 and accompanying channel 350 may be foregone.

Referring specifically to FIG. 26D, the steerable needle 342 further comprises a pull wire 364 affixed to the distal shaft section 346. In the exemplary embodiment, the pull wire 364 is housed within a pull wire lumen 366 extending through the proximal shaft section 342 and bendable shaft section 344, and into the distal shaft section 346. Thus, when the pull wire 364 is tensioned, the bendable shaft section 344 bends, thereby deflecting the distal shaft section 346 relative to the proximal shaft section 342, as illustrated in FIG. 26C. In an alternative embodiment illustrated in FIG. 26E, the steerable needle 342 comprises two pull wires 364 that are clocked from each other 180 degrees and affixed to the distal shaft section 346. In the exemplary embodiment, the pull wires 364a, 364b are respectively housed within two pull wire lumens 366a, 366b extending through the proximal shaft section 342 and bendable shaft section 344, and into the distal shaft section 346. Thus, when the pull wire 364a is tensioned, the bendable shaft section 344 bends, thereby deflecting the distal shaft section 346 relative to the proximal shaft section 342 in first direction. In contrast, when the pull wire 364b is tensioned, the bendable shaft section 344 bends, thereby deflecting the distal shaft section 346 relative to the proximal shaft section 342 in the opposite direction.

The pulmonary access device 314 further comprises a handle assembly 368 affixed to the proximal shaft section 342. The handle assembly 368 includes a handle body 370, which is preferably shaped to be ergonomic for grasping with one hand by the physician. The handle body 346 may be composed of a suitable polymer, such as, e.g., acrylonitrile butadiene styrene (ABS), polyvinylchloride, polycarbonate, polyolefins, polypropylene, polyethylene, etc. The handle assembly 368 further includes a stylet port 371 through which the stylet 356 may be introduced into the working channel 350 of the elongated shaft 340. In one embodiment, the handle assembly 368 includes a luer connector (not shown) that can affix the stylet 356 relative to the elongated shaft 340. Thus, the position of the stylet 356 within the working channel 350 may be affixed by tightening the luer connector. In an optional embodiment, the stylet 356 may be removed from the working channel 350, and an aspiration/suction system can be connected in fluid connection with the working channel 350 via the luer connector.

The handle assembly 368 further includes a deflection control actuator 372 affixed to the handle body 370. The deflection control actuator 372 is operably connected to the pull wire 364, such that the pull wire 364 may be alternately tensioned via manual manipulation of the deflection control actuator 372, thereby bending the bendable shaft section 344 (see FIG. 26C), and relaxed via manual manipulation of the deflection control actuator 372, thereby allowing the resiliency of the elongated shaft 340 to straighten, or at least reduce the bend in, the bendable shaft section 344 (see FIG. 26A). In the embodiment illustrated in FIG. 26A-26C, the deflection control actuator 372 takes the form of a dial that can be manually rotated about the arrow 376 by the thumb of the physician in one direction to tension the pull wire 364, and either manually rotated by the thumb of the physician in the other opposite direction, or simply released, to relax the pull wire 364. In an alternative embodiment, the deflection control actuator 372 may take the form of a plunger that can be manually axially pulled with a finger of the physician to tension the pull wire 364, and either manually axially pushed with the finger or thumb of the physician, or simply released, to relax the pull wire 364 in the same manner as the deflection control actuator 88 illustrated in FIGS. 12, 13, and 14A-14C.

The deflection control actuator 372 may be locked in one or more positions, such that the tension on the pull wire 364, and thus the bend in the bendable shaft section 344, is maintained when the physician releases the deflection control actuator 372, and unlocked to relax the pull wire 364 and straighten the bendable shaft section 44. In the embodiment illustrated in FIGS. 26A-26C, the pulmonary access device 314 is not locked within the working channel 22 of the bronchoscope 12, and thus, may be freely displaced relative to the working channel 18 of the bronchoscope 12. In this case, handle body 370 may simply be rotated about arrow 383 relative to the bronchoscope 12 to rotate the deflected distal shaft section 346 about the longitudinal axis 354 and/or linearly displaced along the arrow 385 relative to the bronchoscope 12 to linearly displace the distal shaft section 346 along the longitudinal axis 354, as illustrated in FIG. 25.

The access sheath 318 has a proximal sheath section 382, a malleable distal sheath section 384, a distal tip 386, and a working channel 388 configured for slidably receiving the elongated shaft 340 of the steerable needle 316. The proximal sheath section 382 may be rigid relative to the malleable distal sheath section 384. For the purposes of this specification, the term "malleable" with respect to the distal sheath section 384 means that the distal sheath section 384 can be repeatedly reshaped in response to forces exerted on the distal sheath section 384 by the steerable needle 316 when disposed in the working channel 388 of the access sheath 318 (i.e., the distal sheath section 384 assumes the shape of the steerable needle 316), which shape is retained when the steerable needle 316 is removed from the working channel 388 of the access sheath 318. In the illustrated embodiment, the distal tip 386 is soft and tapered to facilitate traversal, while minimizing trauma, to tissue as the access sheath 318 is distally advanced over the steerable needle 316, as will be described in further detail below. In alternative embodiment, the distal tip 386 may have barbs or hooks to facilitate its retention within the parenchyma of the lung.

Figure 27:
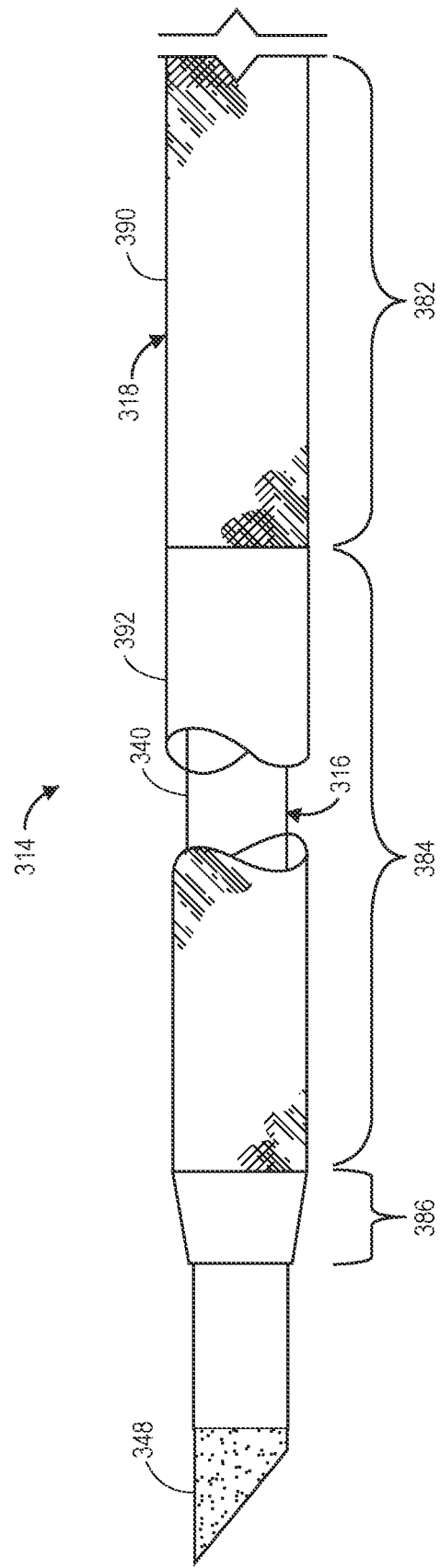
FIG. 27 is a close-up view of the distal end of the pulmonary access device of FIG. 26A.
Figure 28:
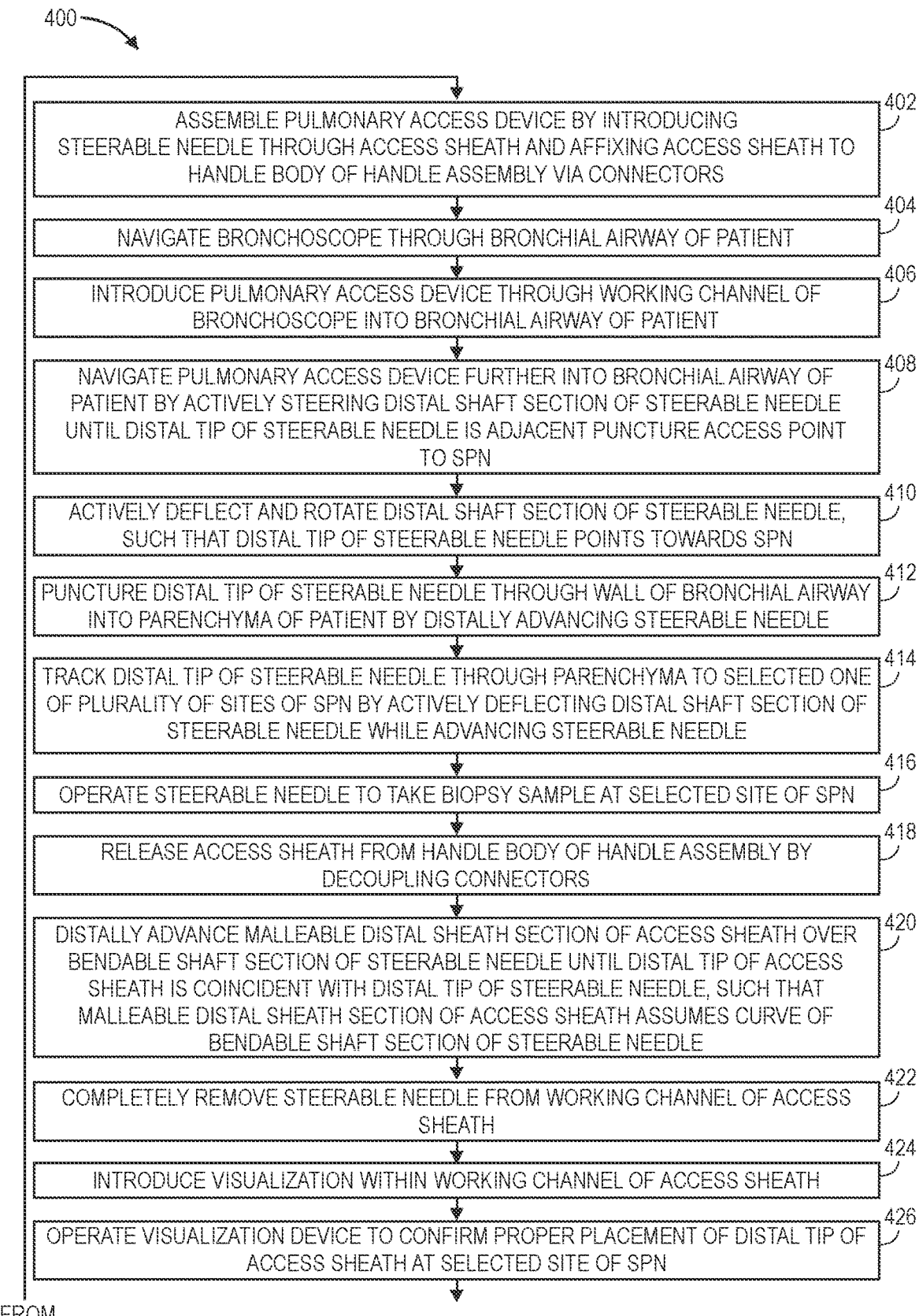
FIG. 28 is a flow diagram of a method of operating the transbronchial pulmonary biopsy system of FIG. 25 to take biopsy samples from a solitary pulmonary nodule (SPN) of a patient.
Figure 28:
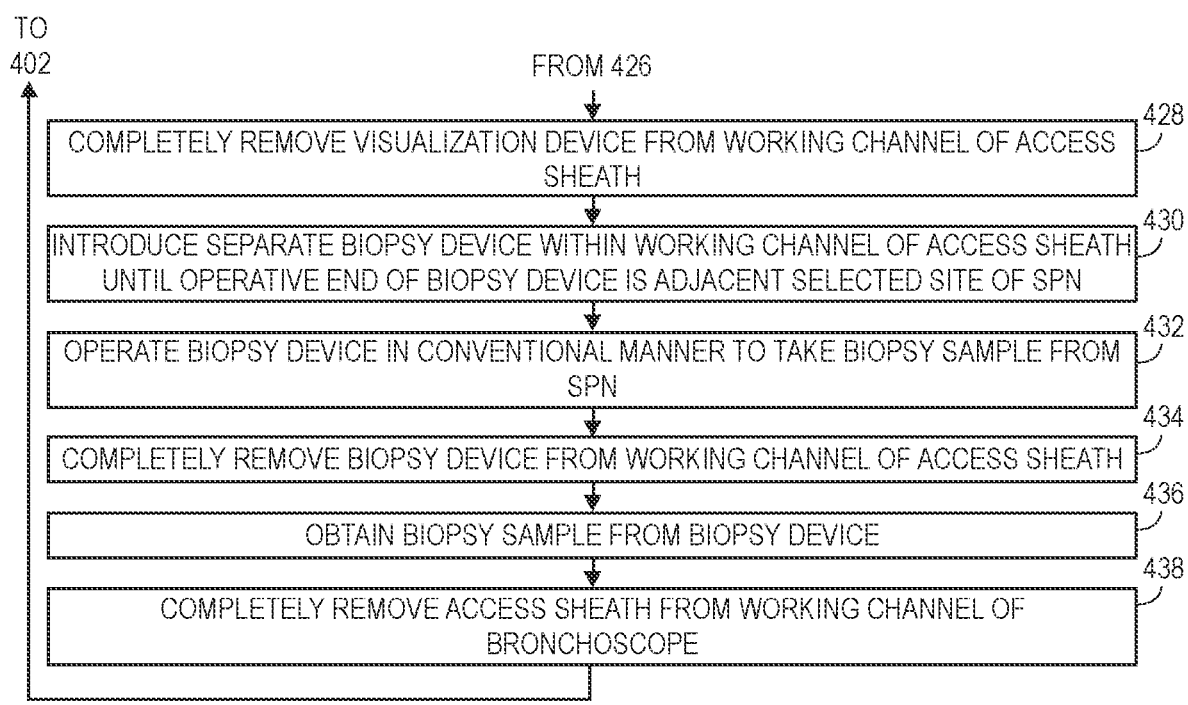

In one embodiment illustrated in FIG. 27, the access sheath 318 comprises a proximal tube 390 extending along the proximal sheath section 382, and a distal tube 392 extending along the malleable distal sheath section 384. The proximal tube 390 can be composed of a metal to facilitate axial and torque transmission along the proximal sheath section 382. For example, the proximal tube 390 may be composed of a multi-strand wound stainless steel wire construction designed to maximize torque transmission in either rotational direction while maximizing axial compression resistance to enable efficient steering. In an alternative embodiment, the proximal tube 390 may be composed of a polymeric material (e.g., nylon, Pebax® elastomer, polyurethane, or a laminate design) having a relatively high durometer (e.g., 90D). The polymeric proximal tube 390 may be reinforced with a uniform braid (e.g., 0.001"×0.003" flat wire composed of a stainless steel braid of 55 picks per inch (ppi)) to resist both compression and torsional loss.

In contrast, the distal tube 392 may have a malleable construction, e.g., shapeable polymer, annealed stainless steel, polymer covered annealed steal, braided soft polymer, etc. In an optional embodiment, the proximal tube 390 and distal tube 392 are radiopaque to enable visualization of the access sheath 318 under fluoroscopy. For example, the metallic nature of the proximal tube 390, and if applicable the distal tube 392, inherently provides radiopaqueness to the access sheath 318. In the case where the proximal tube 390 and/or distal tube 392 are polymeric, the polymer may be loaded within radiopaque particles, such as tungsten or bismuth.

The proximal tube 390 and distal tube 392 may be affixed to each other in any suitable manner. For example, the proximal tube 390 and distal tube 392 may be affixed to each other via a lap joint. In the illustrated embodiment, the distal end of the proximal tube 390 has a reduced diameter, such that the proximal end of the distal tube 392 may be fitted over the reduced distal end of the proximal tube 390 and bonded together.

The proximal end of the access sheath 318 is configured for being removably affixed to the handle body 370 of the handle assembly 368. In the illustrated embodiment, the handle assembly 368 and the access sheath 318 respectively have complementary connectors 394, 396, e.g., luer connectors, that can be selectively coupled together to affix the access sheath 318 to the handle body 370 and decoupled from each other to release the access sheath 318 from the handle body 370. When the access sheath 318 is affixed to the handle body 370 via coupling of the connectors 394, 396, the distal tip 386 of the access sheath 318 is preferably proximally located relative to the bendable shaft section 344 of the steerable needle 316, as illustrated in FIG. 26A. In this manner, the access sheath 318 will not hinder the steerability of the steerable needle 316. Alternatively, when the access sheath 318 is affixed to the handle body 370 via coupling of the connectors 394, 396, the distal tip 386 of the access sheath 318 extends distal of the bendable shaft section 344 of the steerable needle 316, e.g., to the distal tip 386 of the elongated shaft 340.

When the access sheath 318 is released from the handle body 370 via decoupling of the connectors 394, 396, the access sheath 318 is free to linearly translate along the longitudinal axis 354 (see arrow 398) relative to the steerable needle 316. In the preferred embodiment, the released access sheath 318 may be distally advanced, such that the distal tip 386 of the access sheath 318 extends to, or distal of, the distal tip 348 of the steerable needle 316, as illustrated in FIG. 26B. Furthermore, the released access sheath 318 may be distally advanced, such that the malleable distal sheath section 384 of the access sheath 318 respectively longitudinally aligns with bendable shaft section 344 and distal shaft section 346 of the steerable needle 316. Thus, when the bendable shaft section 344 of the steerable needle 316 is bent or curved to deflect the distal shaft section 346 relative to the proximal shaft section 342, the released access sheath 318 may be distally advanced, such that the distal sheath section 384 of the access sheath 318 is disposed over, and assumes the curve of, the bendable shaft section 344 and distal shaft section 346 of the steerable needle 316, as illustrated in FIG. 26C. Of course, in the alternative embodiment where the distal sheath section 384 of the access sheath 318 is already disposed over the bendable shaft section 344 and distal shaft section 346 of the steerable needle 316 prior to bending or curving the bendable shaft section 344 of the steerable needle 316, the distal sheath section 384 will naturally assume the curve of the bendable shaft section 344 and distal shaft section 346 of the steerable needle 316 as the curve is formed. Regardless, the rigidity of the distal sheath section 384 of the access sheath 318 allows it to retain the curve of the bendable shaft section 344 and distal shaft section 346 of the steerable needle 316 when the steerable needle 316 is removed from the working channel 350 of the access sheath 318.

Although the pulmonary access device 314 has been described as being capable of manually manipulated via the handle assembly 368, it should be appreciated that the pulmonary access device 314 may form a portion of a robotic medical system, in which case, the steerable needle 316 and the access sheath 318 of the pulmonary access device 314 may be operably connected to a robotic actuation of the robotic medical system. Furthermore, although the pulmonary access device 314 has been described as comprising a steerable needle capable of puncturing into the parenchyma of a lung, in cases where an SPN is not in the parenchyma of a lung, but rather in the airway of the lung, it may be not be desirable to puncture into the parenchyma of a lung. In this case, the pulmonary access device 314 may have a steerable elongated member that functions similarly as the steerable needle 316, but is not capable of puncturing into the parenchyma of a lung.

Referring to FIGS. 28 and 29A-29H, one exemplary method 400 of using the transbronchial pulmonary biopsy system 310 to take biopsy samples from different sites of an SPN located in the parenchyma P of a patient will now be described.

First, the pulmonary access device 314 is assembled by introducing the steerable needle 316 through the access sheath 318 and affixing the access sheath 318 to the handle body 370 of the handle assembly 356 via the connectors 394, 396 (shown in FIGS. 26A-26C) (step 402). In the case where the steerable needle 316 includes a profile stylet 356, it can be introduced within the working channel 350 of the elongated shaft 340 (e.g., by introducing the profiled stylet 356 through the stylet port 371 associated with the handle body 370 (shown in FIGS. 26A-26C), and into the working channel 350 along the elongated shaft 340) until the distal stylet section is aligned with or proximal to the distal tip 348 of the elongated shaft 340.

Figure 29A:
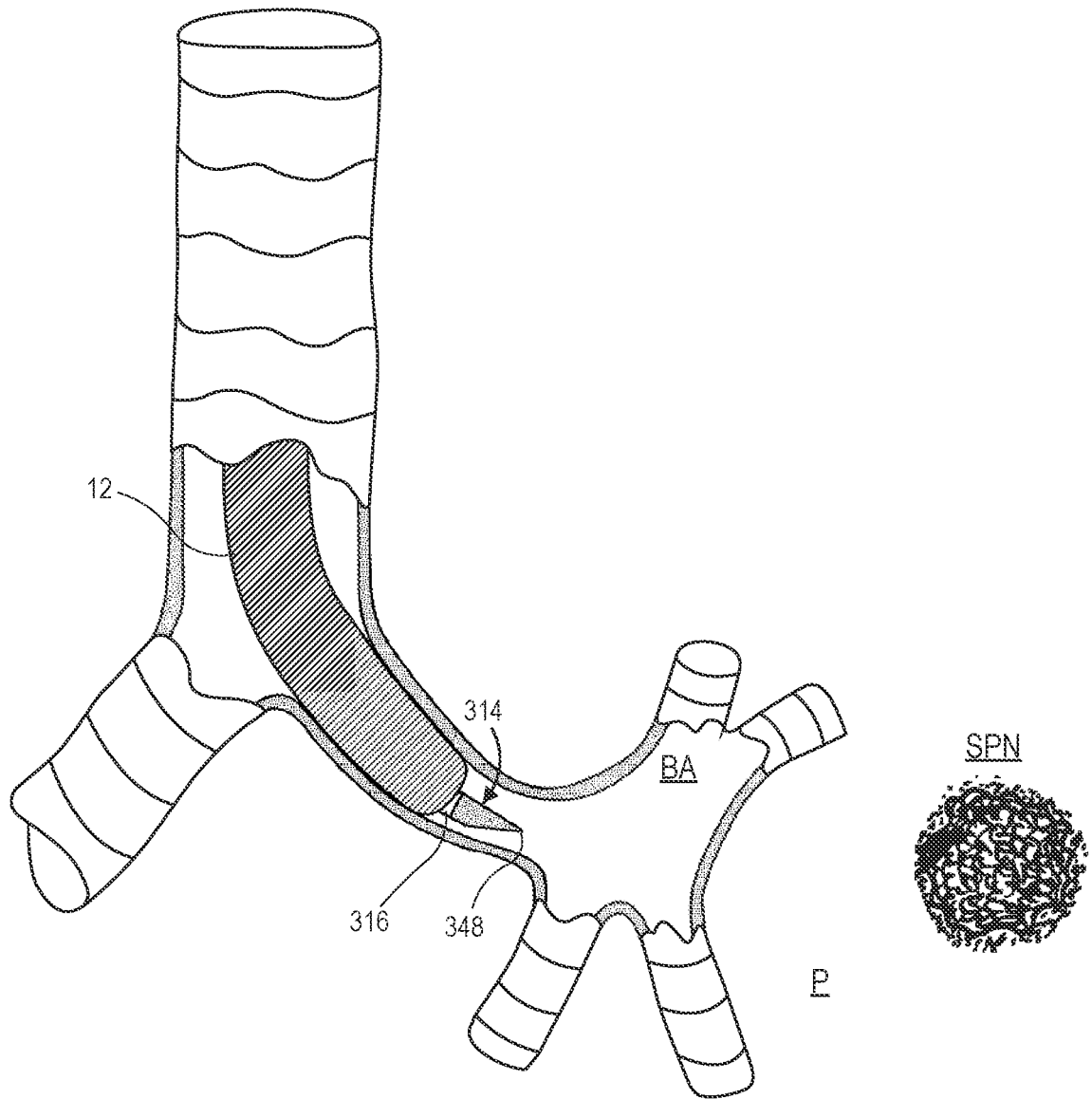
FIGS. 29A-29H are plan views illustrating the transbronchial pulmonary biopsy system of FIG. 25 in use to take biopsy samples from the SPN of the patient in accordance with the method of FIG. 28.

Next, the pulmonary access device 314 is navigated through a bronchial airway BA of the patient. In particular, the bronchoscope 12 is navigated through the bronchial airway BA of the patient in a conventional manner (step 404), as illustrated in FIG. 24A, and the pulmonary access device 314 is then introduced through the working channel 22 of bronchoscope 12 (shown in FIG. 1) (e.g., via the access port 25 of the bronchoscope 12) into the bronchial airway BA of the patient (step 406), as illustrated in FIG. 29A. In an alternative embodiment, the access sheath 318, without the steerable needle 316, may be introduced through the working channel 22 of the bronchoscope 12, and then the steerable needle 316 introduced through the working channel 350 of the previously introduced access sheath 318. The access sheath 318 may then be affixed to the handle body 370 of the handle assembly 356 via the connectors 394, 396.

Figure 29B:
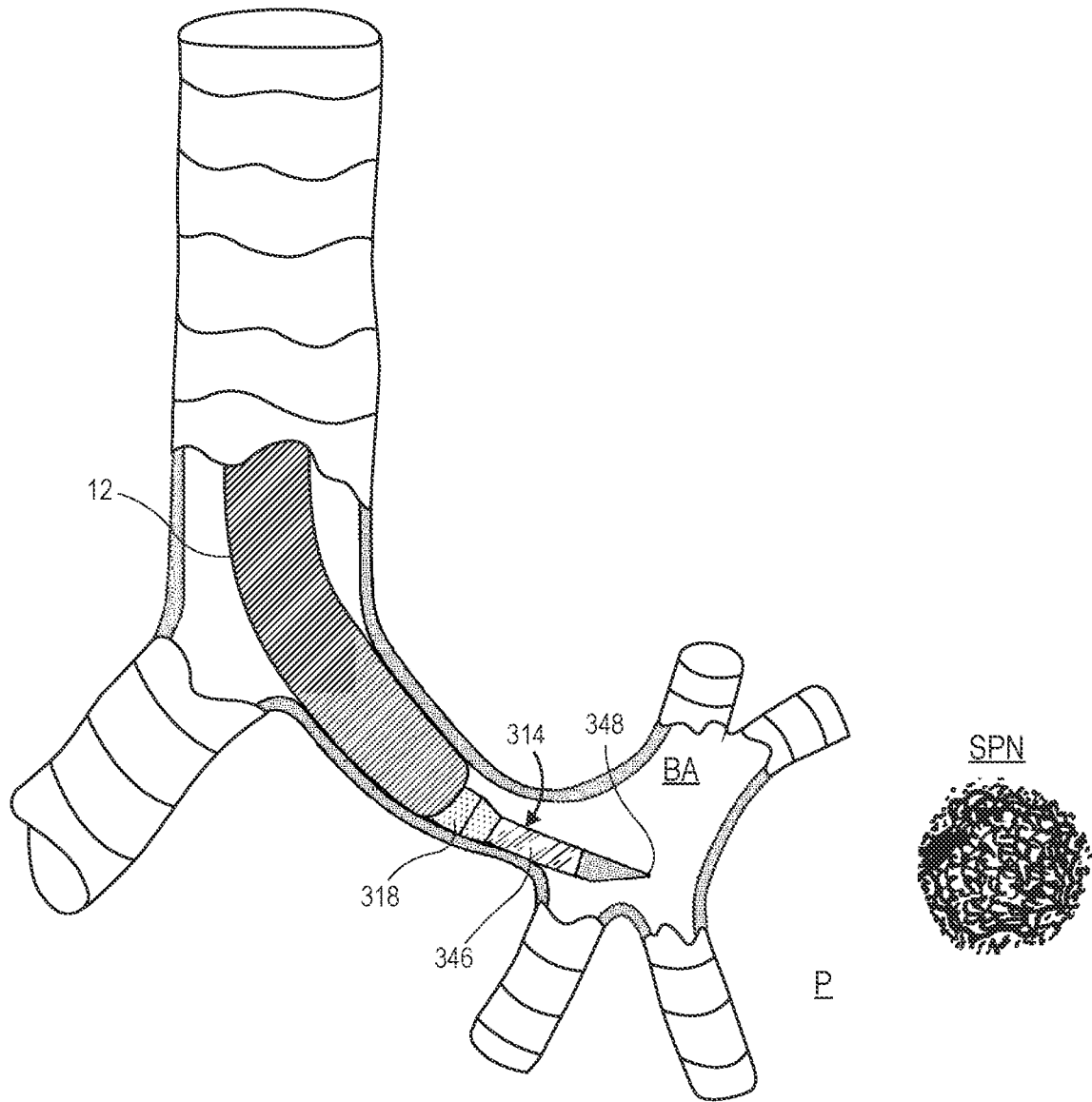

The pulmonary access device 314 is then navigated further into the bronchial airway BA of the patient by actively steering the distal shaft section 346 while distally advancing the pulmonary access device 314 within the bronchial airway BA of the patient until the distal tip 348 of the steerable needle 316 is adjacent the access puncture point to the SPN (step 408), as illustrated in FIG. 29B. In the exemplary embodiment, the steerable needle 316 is actively steered by tensioning the pull wire 364 via manipulation of the deflection control actuator 372 to actively deflect the distal shaft section 346 of the steerable needle 316, and the steerable needle 316 is distally advanced within the bronchial airway BA of the patient via linear displacement of the handle body 370 illustrated in FIGS. 26A-26C. Notably, the distal tip 386 of the access sheath 318 does not cover any portion of the bendable shaft section 344 or the distal shaft section 346 of the steerable needle 316, such that the access sheath 318 does not hinder the steering functionality of the steerable needle 316.

Next, if the distal tip 348 of the steerable needle 316 is not already pointed towards the SPN, the distal shaft section 346 is actively deflected and rotated about the longitudinal axis 354 of steerable needle 316, such that the distal tip 348 of the steerable needle 316 points towards the SPN (step 410). In the exemplary embodiment, the distal shaft section 346 of the steerable needle 316 is actively deflected by tensioning the pull wire 364 (e.g., via manipulation of the deflection control actuator 372, and rotated via rotation of the handle body 370 illustrated in FIGS. 26A-26E).

Figure 29C:
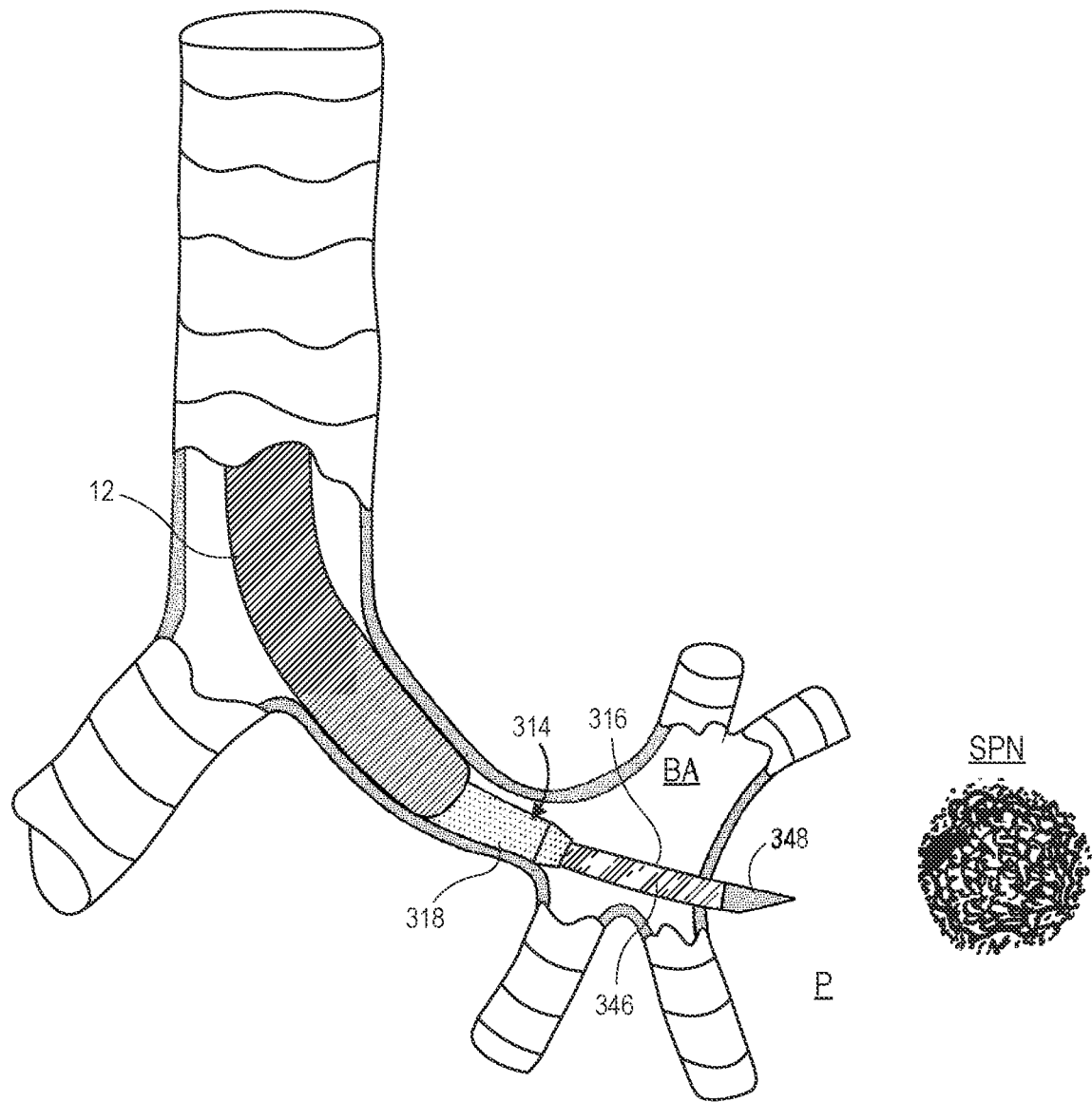

The distal tip 348 of the steerable needle 316 (with or without a profiled stylet 356) is then punctured through the wall of the bronchial airway PA into the parenchyma P by distally advancing the pulmonary access device 314 (step 412), as illustrated in FIG. 29C. In the exemplary embodiment, the pulmonary access device 14 is distally advanced within the bronchial airway BA of the patient via linear displacement of the handle body 70 illustrated in FIGS. 26A-26C). Prior to puncturing through the wall of the bronchial airway PA into the parenchyma P, if the steerable needle 316 comprises a profiled stylet 356 and the distal tip 48 of the elongated shaft 340 is tissue-penetrating, the profiled stylet 356 may be proximally retracted slightly within the working channel 350 of the elongated shaft 340 until the distal stylet section 362 (obturator) is aligned with or proximal to the tissue-penetrating distal tip 348 of the elongated shaft 340, thereby exposing the tissue-penetrating distal tip 348 of the elongated shaft 340 similar to the arrangement of the pulmonary access device 14 illustrated in FIG. 21D. If the steerable needle 316 comprises a profiled stylet 356 and the distal tip 48 of the elongated shaft 340 is atraumatic, the profiled stylet 356 may be distally advanced within the working channel 350 of the elongated shaft 340 until the tissue-penetrating distal stylet section extends distally from the atraumatic distal tip 348 of the elongated shaft 340 similar to the arrangement of the pulmonary access device 14 illustrated in FIG. 24D.

Figure 29D:
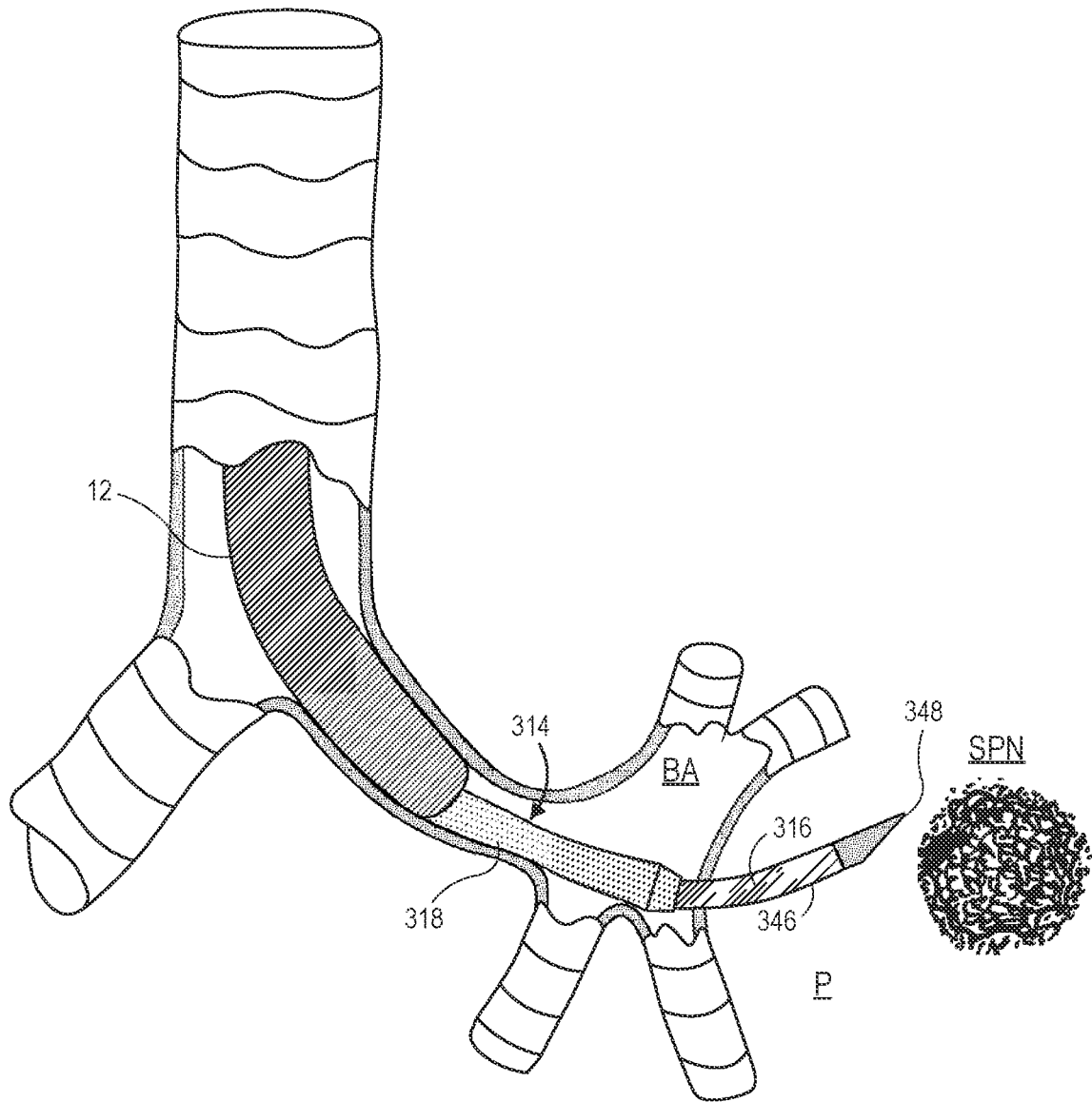

Next, the distal tip 348 of the steerable needle 316 is tracked through the parenchyma P to a selected one of a plurality of different sites of the SPN by actively deflecting the distal shaft section 346 of the steerable needle 316 while distally advancing the pulmonary access device 314 (step 414), as illustrated in FIG. 29D. In the exemplary embodiment, the distal shaft section 346 of the steerable needle 316 is actively deflected by tensioning the pull wire 364 (e.g., via manipulation of the deflection control actuator 372 illustrated in FIGS. 26A-26E). Any one of a plurality of different sites of the SPN may be selected by controllably deflecting the distal shaft section 346, similar to the arrangement of the pulmonary access device 14 illustrated in FIG. 21G or 24G. As such, multiple biopsies may be taken from various sites of the SPN, thereby maximizing the diagnostic yield of the biopsy.

Optionally, if it has biopsy functionality, the steerable needle 316 may be operated to take a biopsy sample at the selected site of the SPN (step 416). For example, if the steerable needle 316 takes the form of a biopsy needle, the biopsy sample may be taken at the selected site of the SPN in accordance with steps 118-126 of the method 100 performed by the pulmonary access device 14 (see FIGS. 21H-21J). As another example, if the steerable needle 316 takes the form of an access device, the biopsy sample may be taken at the selected site of the SPN in accordance with steps 218-230 of the method 200 performed by the pulmonary access device 14 (see FIGS. 24H-24J).

Figure 29E:
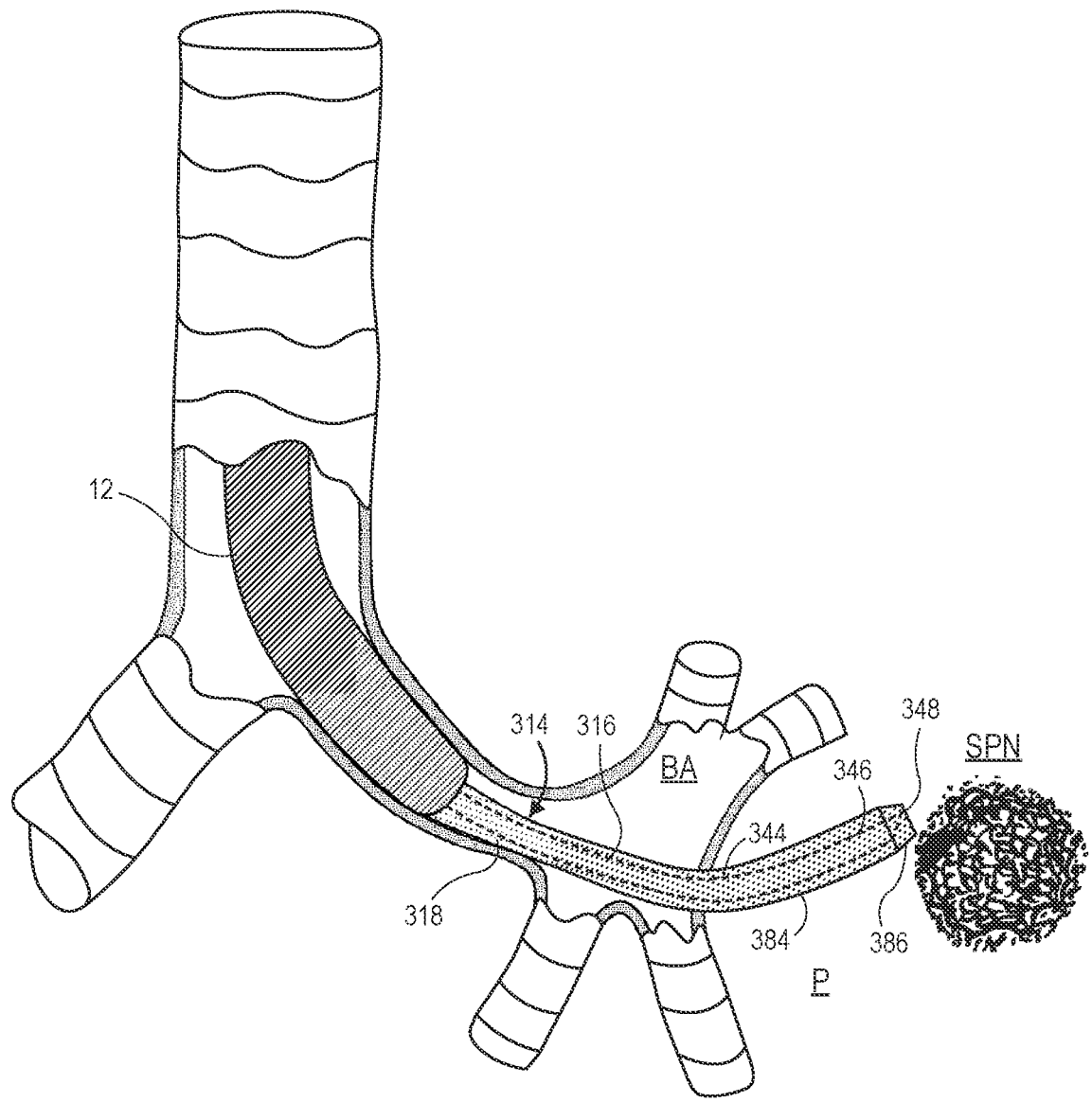

Next, while the distal tip 348 of the steerable needle 316 is located at the selected site of the SPN, and the access sheath 318 is released from the handle body 370 of the handle assembly 368 by decoupling the connectors 394, 396 (step 418). While the distal shaft section 346 of the elongated shaft 340 is actively deflected, the malleable distal sheath section 384 of the access sheath 318 is distally advanced over the bendable shaft section 344 of the steerable needle 316 until the distal tip 386 of the access sheath 318 is coincident with the distal tip 348 of the steerable needle 316, such that the malleable distal sheath section 384 assumes a curve of the bendable shaft section 344 of the steerable needle 316 (step 420), as illustrated in FIG. 29E.

Figure 29F:
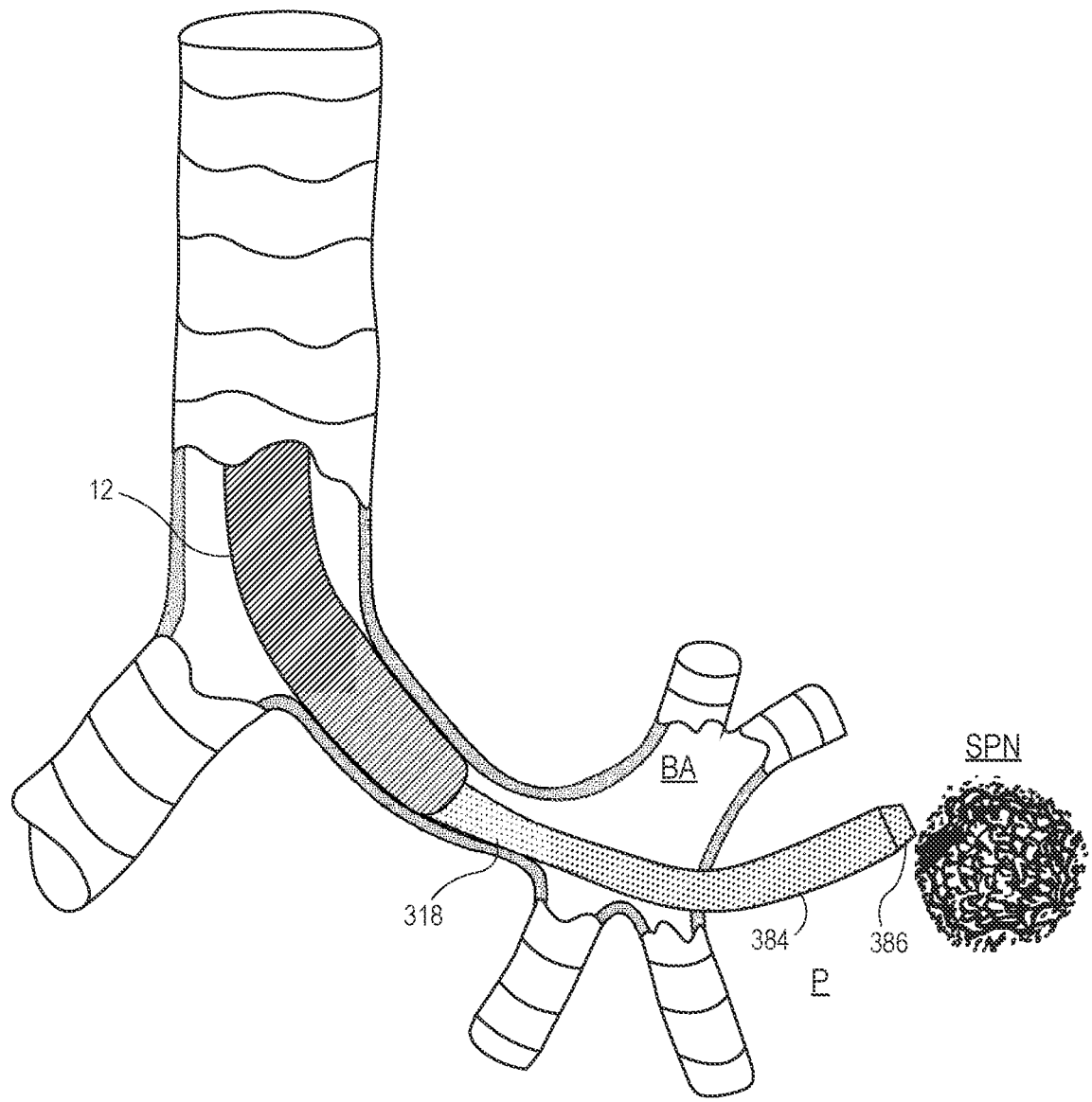
Figure 29G:
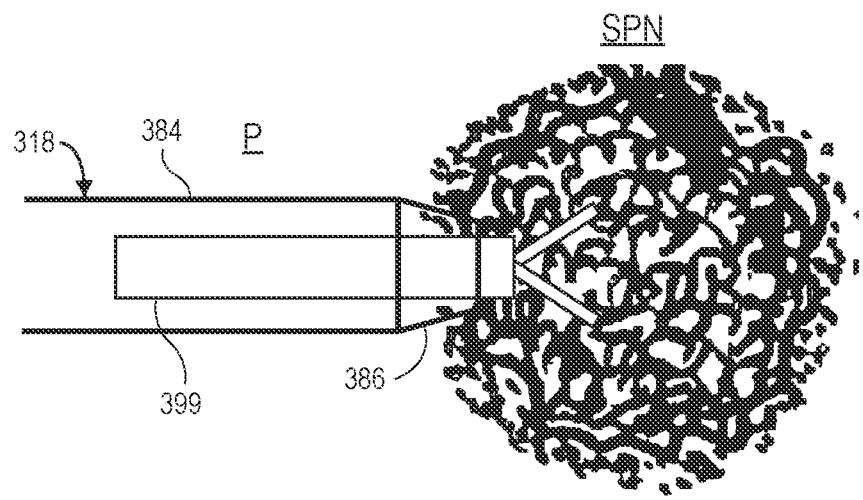
Figure 29H:
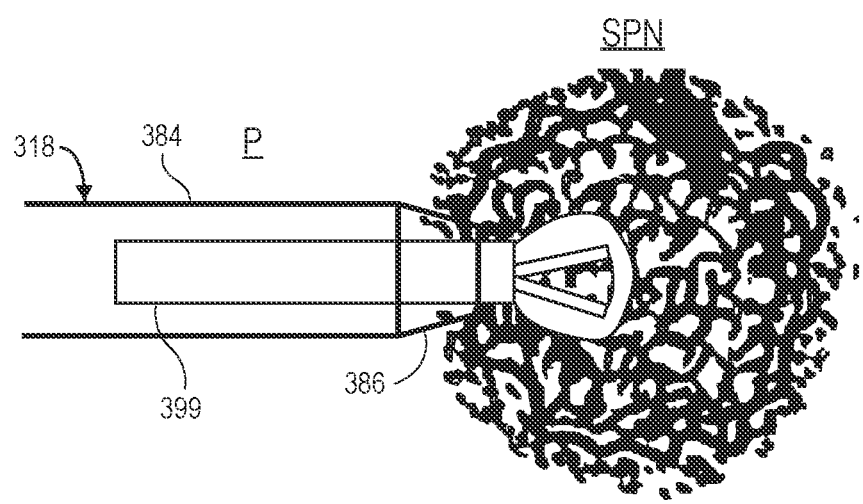

Next, the steerable needle 318 is completely removed from the working channel 388 of the access sheath 318 (step 422), as illustrated in FIG. 29F. Significantly, due to its inherent rigidity, the malleable distal sheath section 384 retains the assumed curve of the bendable shaft section 344 when the steerable needle 318 is removed from the access sheath 318. Next, a visualization device (not shown) (e.g., an Endobronchial Ultrasound (EBUS) device manufactured by Olympus) is introduced through the working channel 388 of the access sheath 318 (step 424) and operated to confirm proper placement of the distal tip 386 of the access sheath 318 at the selected site of the SPN (step 426). One proper placement is confirmed, the visualization device is completely removed from the working channel 388 of the access sheath 318 (step 428), and a separate biopsy device 399 (e.g., biopsy forceps) is introduced within the working channel 388 of the access sheath 318 (shown in FIG. 25) until the operative end of the biopsy device 399 is at the selected site of the SPN (step 430), as illustrated in FIG. 29G. The biopsy device 399 is then operated in a conventional manner to take a biopsy sample from the SPN (step 432), as illustrated in FIG. 29H. The biopsy device 399 is then completely removed from the working channel 388 of the access sheath 318 (step 434), and the biopsy sample is obtained from the biopsy device 399 (step 436). The access sheath 318 is completely removed from the working channel 22 of the bronchoscope 12 (e.g., via the access port 25 the bronchoscope 12) (step 438), and steps 402-438 repeated to take another biopsy sample from a different site of the SPN.

Although the method of using the transbronchial pulmonary biopsy system 310 has been described as taking biopsy samples from an SPN located in the parenchyma of a lung, it should be appreciated that the transbronchial pulmonary biopsy system 310 can be used to take biopsy samples from an SPN that is in the airway in the periphery of the lung as well.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

The invention claimed is:
1. A pulmonary access device, comprising:
an elongated shaft having a proximal shaft section, a bendable shaft section configured for being deflected into a curve, a distal shaft section, and a distal tip;
an elongated sheath having a proximal sheath section, a malleable distal sheath section, and a working channel, the working channel configured for slidably receiving the elongated shaft; and
a handle assembly including a handle body, a proximal end of the elongated shaft being affixed to the handle body, a proximal end of the elongated sheath being removably affixed to the handle body;
wherein the malleable distal sheath section configured for being distally advanced over the bendable shaft section, such that the malleable distal sheath section assumes the curve of the bendable shaft section; and
wherein the elongated shaft is configured for being removed from the working channel of the elongated shaft, and the malleable distal sheath section is configured for retaining the assumed curve of the bendable shaft section after the elongated shaft is removed from the working channel of the elongated sheath.

2. The pulmonary access device of claim 1, wherein the bendable shaft section distally extends from the malleable distal sheath section when the handle body is affixed to the proximal end of the elongated sheath.

3. The pulmonary access device of claim 1, wherein the handle assembly further comprises a deflection control actuator affixed to the handle body, the deflection control actuator operably connected to the elongated shaft to bend the bendable shaft section.

4. The pulmonary access device of claim 1, wherein the proximal end of the elongated sheath and the handle body have complementary connectors configured for mating the elongated sheath and handle body together.

5. The pulmonary access device of claim 4, wherein the connectors are luer connectors.

6. The pulmonary access device of claim 1, wherein the elongated shaft further has a working channel, the pulmonary access device further comprising:
a profiled stylet configured for being disposed in the working channel of the elongated shaft, the profiled stylet having a proximal stylet section with a first lateral stiffness profile, an intermediate stylet section having a second lateral stiffness profile less than the first lateral stiffness profile, and a distal stylet section, wherein, when the profiled stylet is disposed in the working channel of the elongated shaft, the intermediate stylet section axially aligns with the bendable shaft section; and
a pull wire affixed to the distal shaft section, such that, when the pull wire is tensioned, the bendable shaft section bends, thereby deflecting the distal shaft section relative to the proximal shaft section.

7. A pulmonary biopsy system, comprising:
the pulmonary access device of claim 1; and
a bronchoscope having a working channel in which the pulmonary access device is disposed.

8. The pulmonary biopsy system of claim 7, further comprising a biopsy device and a stylet, the stylet and the biopsy device configured for being interchangeably disposed in the working channel of the pulmonary access device.

\* \* \* \* \*